United States Patent
Luk et al.

(10) Patent No.: US 11,357,786 B2
(45) Date of Patent: Jun. 14, 2022

(54) SYNTHETIC DISUGAR HYDROCARBONS AS NATURAL ANALOGS TO CONTROL MICROBIAL BEHAVIORS

(71) Applicants: Yan-Yeung Luk, Jamesville, NY (US); Guirong Wang, Syracuse, NY (US)

(72) Inventors: Yan-Yeung Luk, Jamesville, NY (US); Guirong Wang, Syracuse, NY (US)

(73) Assignees: Syracuse University, Syracuse, NY (US); The Research Foundation for the State University of New York, Syracuse, NY (US)

( * ) Notice: Subject to any disclaimer, the term of this patent is extended or adjusted under 35 U.S.C. 154(b) by 0 days.

(21) Appl. No.: 17/061,670

(22) Filed: Oct. 2, 2020

(65) Prior Publication Data

US 2021/0023108 A1    Jan. 28, 2021

Related U.S. Application Data

(60) Continuation of application No. 16/423,543, filed on May 28, 2019, now abandoned, which is a division of application No. 15/300,990, filed as application No. PCT/US2015/024234 on Apr. 3, 2015, now abandoned.

(60) Provisional application No. 61/974,812, filed on Apr. 3, 2014.

(51) Int. Cl.
*A61K 31/7028* (2006.01)
*A61K 9/00* (2006.01)
*A61K 45/06* (2006.01)
*A61K 31/724* (2006.01)

(52) U.S. Cl.
CPC ........ *A61K 31/7028* (2013.01); *A61K 9/0078* (2013.01); *A61K 31/724* (2013.01); *A61K 45/06* (2013.01); *Y02A 50/30* (2018.01)

(58) Field of Classification Search
CPC .... A61K 31/7028; A61K 9/0078; A61P 31/04
See application file for complete search history.

(56) References Cited

PUBLICATIONS

Stoops et al., In vivo, 2010, 24, p. 687-694. (Year: 2010).*
Smith et al., Thorax, 1984, 39, p. 369-375. (Year: 1984).*
Sermet-Gaudelus et al., Pediatr. Drugs, 2002; 4(7), p. 455-467. (Year: 2002).*

* cited by examiner

*Primary Examiner* — Jonathan S Lau
(74) *Attorney, Agent, or Firm* — Bond Schoeneck and King PLLC; David Nocilly

(57) ABSTRACT

Synthetic disaccharide hydrocarbons (DSHs) that reactive bacterials swarming motility and inhibit bacterial adhesion and biofilm formation. A library of DSHs were tested in several experiment for the impact on various *Pseudomonas aeruginosa* populations and compared against existing compounds to determine efficacy and utility. Certain DSHs were also to determine the ability to clear bacteria in a mouse pneumonia model.

7 Claims, 47 Drawing Sheets

Figure 9. Surface attached PAO1 biofilm remaining within the wells of microtiter plate after biofilm was allowed to develop for 24 hours with or without various agents. Concentration of [13: SFαC]

Infection + Saline    Infection + DM

Disugar isobutyl ether

Different stereochemistries iBEβM iBEβC iBEαC

I : GalNAcβ(1→4)Galβ-C$_{12}$    II : GalNAcα(1→4)Galβ-C$_{12}$

III : GlcNAcβ(1→4)Galβ-C$_{12}$    IV : GlcNAcβ(1→4)Galβ-C$_{12}$-O-Bn

V: GlcNAcβ(1→4)Galβ-SF

VI: GlcNAcβ(1→4)Galβ-SF

VII: GlcNAcα(1→4)Galβ –$C_{12}$

VIII : Mixture of GlcNβ(1→4)Galβ-$C_{12}$ GlcNα(1→4)Galβ-$C_{12}$ mole ratio 7:3

SYNTHETIC DISUGAR HYDROCARBONS AS NATURAL ANALOGS TO CONTROL MICROBIAL BEHAVIORS

CROSS-REFERENCE TO RELATED APPLICATIONS

The present application is a divisional of U.S. application Ser. No. 15/300,990, filed on Sep. 30, 2016, which was a national stage application of PCT/US15/24234, filed on Apr. 3, 2015, which claimed priority to U.S. Provisional Application No. 61/974,812, filed on Apr. 3, 2014.

STATEMENT REGARDING FEDERALLY SPONSORED RESEARCH OR DEVELOPMENT

This invention was made with government support under Grant No. IIP-1242505 awarded by the National Science Foundation, and Grant No. CMMI-0845686 awarded by the National Science Foundation. The government has certain rights in the invention.

BACKGROUND OF THE INVENTION

1. Field of the Invention

The present invention relates to the control of bacterial behavior and, more particularly, to the use of synthetic disaccharide hydrocarbons on the swarming motility of bacteria.

2. Description of the Related Art

Microbes secrete chemicals for a wide range of functions. These chemicals include agents that signal population density to each other and induce a collective behavior, molecules that build structured film in which the microbes reside, virulence factors that are toxic to a host cell or other species, agents that enables the swarming motility of a collection of members of the microbes. Controlling these behaviors without killing the microbes has the potential of developing drugs against infectious diseases without invoking drug resistances, and enables both chemical and bacteria-based waste cleanup for environmental bioremediation The emerging increases in antibiotic resistant bacteria call for fundamentally new approaches in treating wide ranges of infectious and new diseases. The discovery of quorum sensing in bacteria leading to biofilm formation and recognizing the detrimental effects that biofilm formation poses has made the exploration of non-microbicidal anti-biofilm approaches an important area of research. To this end, important work has been done in inhibiting the quorum sensing among the bacteria to reduce the biofilm formation. Another approach focuses on the hypothesis that bacterial adhesion is a major step causing various diseases, thus inhibiting the adhesion of microbes or developing vaccines using the microbial adhesins may be a potential therapeutics for infectious diseases. However, this anti-adhesion strategy has not yet reached an ultimate success of drug development, probably because multiple adhesins are employed by the microbe for adhesion and attachment of polymer secreted by the microbes can also facilitate the hosting of microbes that may also lead to the formation of biofilms.

*Pseudomonas aeruginosa* is an opportunistic pathogen that causes severe infections under a wide range of immunocompromised situations. Many bacterial activities are gene-regulated. Swarming motility of *P. aeruginosa* on a soft agar gel requires the production of a natural disaccharide derivative, rhamnolipid, that is also gene controlled and is produced by a few other bacterial species. Rhamnolipids control at least three different behaviors of *P. aeruginosa*. First, it is necessary for making structured biofilms with channels and pores. Second, it facilitates the partial dispersion of mature biofilms when overproduced. Third, its production is necessary for enabling the swarming motility of *P. aeruginosa*. Deleting the gene rhlA that controls the synthesis of rhamnolipids results in a non-swarming mutant. With all these biological activities, the protein receptor(s), as well as its existence, for rhamnolipid has not yet been identified. Furthermore, the natural ligand for mediating the adhesion of *P. aeruginosa* on epithelial cells of lungs in cystic fibrosis patients is believed to be a disaccharide derivative, GalNAcβ(1→4)Galβ moiety, on the asialo-GM1 glycolipid. Synthetic molecules that tether different methylated GalNAcβ(1→4)Galβ on different aliphatic chains have shown to be potent anti-adhesion agents for *P. aeruginosa*, and that the receptor appears to be a pili protein. Structural variation and mimics of the disaccharide glucosamine (different stereochemistry and the presence of NAc group) has not been extensively evaluated for inhibiting the adhesion of *P. aeruginosa*.

One of the most prevalent bacterial activities for diseases is biofilm formation, which is also gene regulated, resulting in a dynamic surface-based multicellular organism. The film-hosting microbes can exhibit 1000 fold higher resistance to antibiotics than the planktonic microbes. Complete eradication of biofilms has been a daunting challenge as these films can exhibit resistance to many chemical agents. Interestingly, while the initial step of biofilm formation are believed to involve microbial adhesion on host surfaces (or on adsorbed polymer secreted by the microbes), relatively few studies have been explored using anti-adhesion agents to inhibit or disperse biofilm formation.

Together, the swarming activities and the ligand-mediated adhesion suggest that disaccharide molecule are potential ligands for one or more receptors that control the signaling processes including swarming motility, adhesion, and biofilm formation and dispersion.

These molecules may be useful for treating infectious diseases, such as these associated with cystic fibrosis. Cystic fibrosis (CF) is the most common autosomal recessive condition present in the Caucasian population, accounting for one in 2500 births. It is a multi-system, progressive disorder characterized by abnormal ion transport leading to viscid secretions affecting the pancreas and the respiratory, gastrointestinal and reproductive systems. The major cause of morbidity and mortality is the respiratory component of the condition. Dysfunction of the cystic fibrosis transmembrane conductance regulator in the CF airway epithelium causes abnormal ion transport which in turn leads to depleted airway surface liquid volume, mucus dehydration, decreased mucus transport and mucus plugging of the airways providing an environment for bacterial infection. This process sets up a cycle of infection and inflammation leading to airway damage and progressive loss of respiratory function. In 1938, 70% of babies with CF died within the first year of life. More recent data suggests that median survival has increased to between 37 and 41 years of age as a result of improvements in conventional therapy. Nebulized treatment has been a key element of these therapies, but at the cost of increased burden of care for people with CF and their families.

BRIEF SUMMARY OF THE INVENTION

The present invention comprises a class of disugar hydrocarbons that simulate and overpower the function of a class of natural molecules, rhamnolipids, secreted by *Pseudomonas aeruginosa*. This class of disugar hydrocarbons exhibits control over multiple microbial behaviors. They promote the swarming motility of *Pseudomonas aeruginosa* at low concentration, but inhibit the swarming motility at high concentrations. This capability of dual-functions dominates the effect from the naturally existing rhamnolipids, and is vastly useful for controlling infectious diseases. This class of molecules also exhibits another important function of controlling the biofilm formed by bacteria. They inhibit the formation of a biofilm by a wide range of microbes (*E. coli, Pseudomonas aeruginosa*, and *Candida albicans*) with a higher potency than that by rhamnolipids. Most importantly, disugar hydrocarbons disperse already formed biofilms whereas natural rhamnolipids extracted from bacteria do not. Because microbial biofilms are the sources of 80% infectious diseases, and because preformed biofilms are particularly difficult to remove, this class of di sugar hydrocarbons has applications in for drug development and formulation.

The present invention also comprises the non-microbicidal control of bacterial behaviors. Various synthetic disaccharide hydrocarbons were used to explore reactivating the swarming motility of a nonswarming mutant of *Pseudomonas aeruginosa* (rhlA), and the ability of the compounds to inhibit bacterial adhesion and biofilm formation by the wild type *P. aeruginosa*. Several of the disaccharide-hydrocarbons reactivated the swarming of rhlA mutant to its full capacity as compared to the wild type *P. aeruginosa*; and the extent of reactivation was highly sensitive to the structural details of the disaccharide-hydrocarbons. While these disaccharide-hydrocarbons were not microbicidal at relatively high concentrations (170 µM) disaccharides with bulky hydrocarbon groups inhibited bacterial adhesion, exhibited biofilm inhibition and dispersion with an $IC_{50}$ of 22.5 µM and a $DC_{50}$ of 31 µM, respectively. Because the swarming motility of rhlA mutant is abolished due to its lack of production of the natural ligand rhamnolipid, the synthetic disaccharide-hydrocarbons may share a common receptor as rhamnolipid. In addition, as bacterial adhesions can also be facilitated by ligand-receptor interactions, the results suggest a new approach of controlling bacterial adhesion, biofilm formation and swarming motilities by a common set of disaccharide-based molecules that targets one or more protein receptors.

The present invention also comprises a chemical library of disaccharide hydrocarbons (DSHs) that were made by systematically changing the glycone as well as a glycone part of the DSH and then investigating the effect that these structural changes have on swarming motilities of PA and its non-swarming mutant strain. The compounds were also tested to determine the anti-biofilm activities of these non-microbicidal agents.

The present invention also involves the effects of Dodecyl Maltoside (DM) on the bacterial clearance and lung inflammation in mouse *P. aeruginosa* pneumonia. DM treatment significantly decreased CFU number in the lung compared to the control and improved the lung inflammation.

The present invention additionally includes a series of synthetic disaccharide hydrocarbons (DSHs) that activates the swarming motility at low concentration but inhibit swarming at high concentration over a wide range of saccharide stereochemistries and aliphatic structures. DSHs with a bulky aliphatic chain (3,7,11-trimethyl-dodecane) exhibited a dominating effect over natural rhamnolipids extract on both activating and inhibiting the swarming motility of *Pseudomonas aeruginosa*. Active DSHs inhibited biofilm formation with a plateau of maximal inhibition as the concentration was increased. The DSHs with a cellobiose head and a saturated farnesol tail, saturated farnesol-β-cellobioside, exhibited higher biofilm inhibition with an $IC_{50}$ of ~9.9 µM than the maximal biofilm inhibition of rhamnolipids extract. More importantly, active DSHs dispersed 1-day old biofilm whereas, rhamnolipids extract did not exhibit any notable dispersion. Together these results demonstrate that the active DSHs dominate natural rhamnolipids at collective behaviors of swarming and biofilm formation in *Pseudomonas aeruginosa*.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 3:
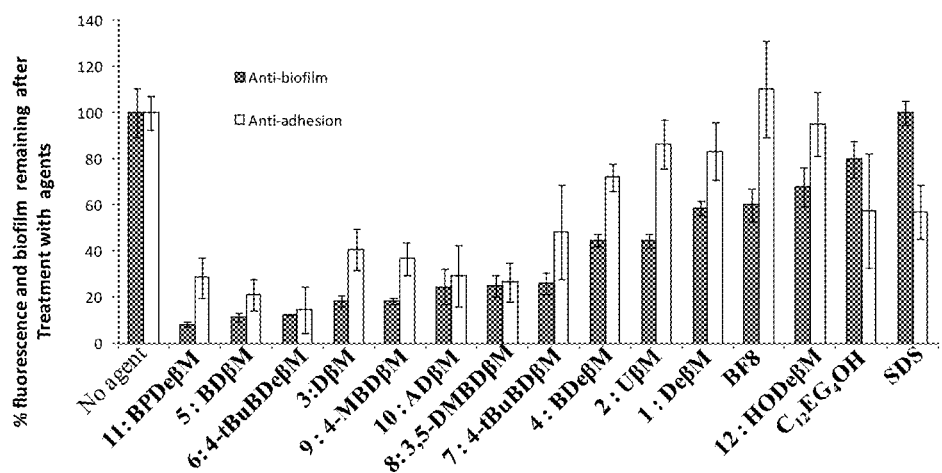
Figure 4:
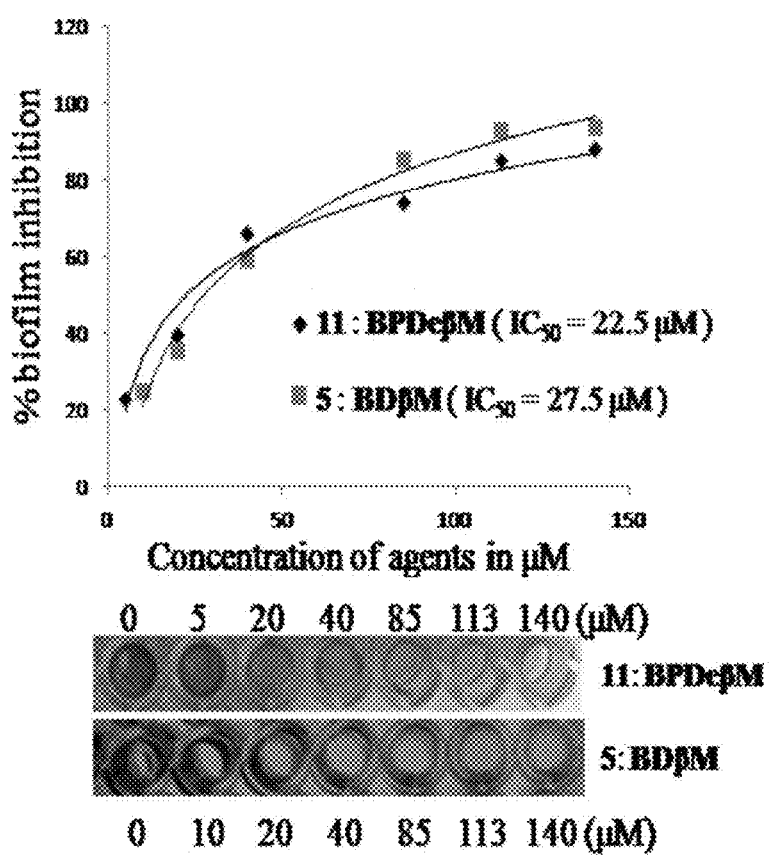
Figure 5:
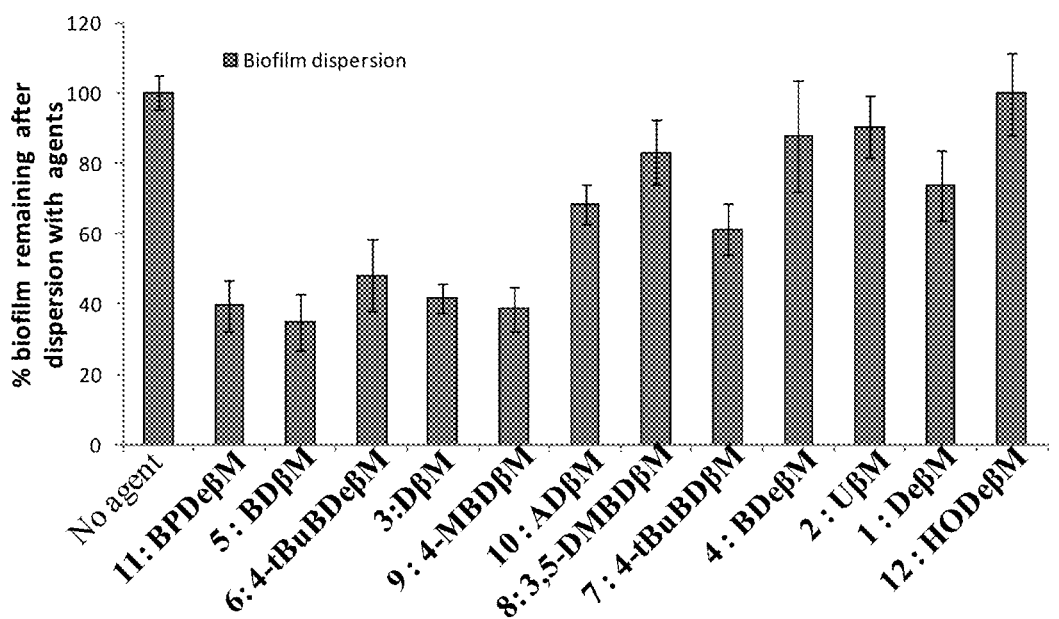
Figure 6:
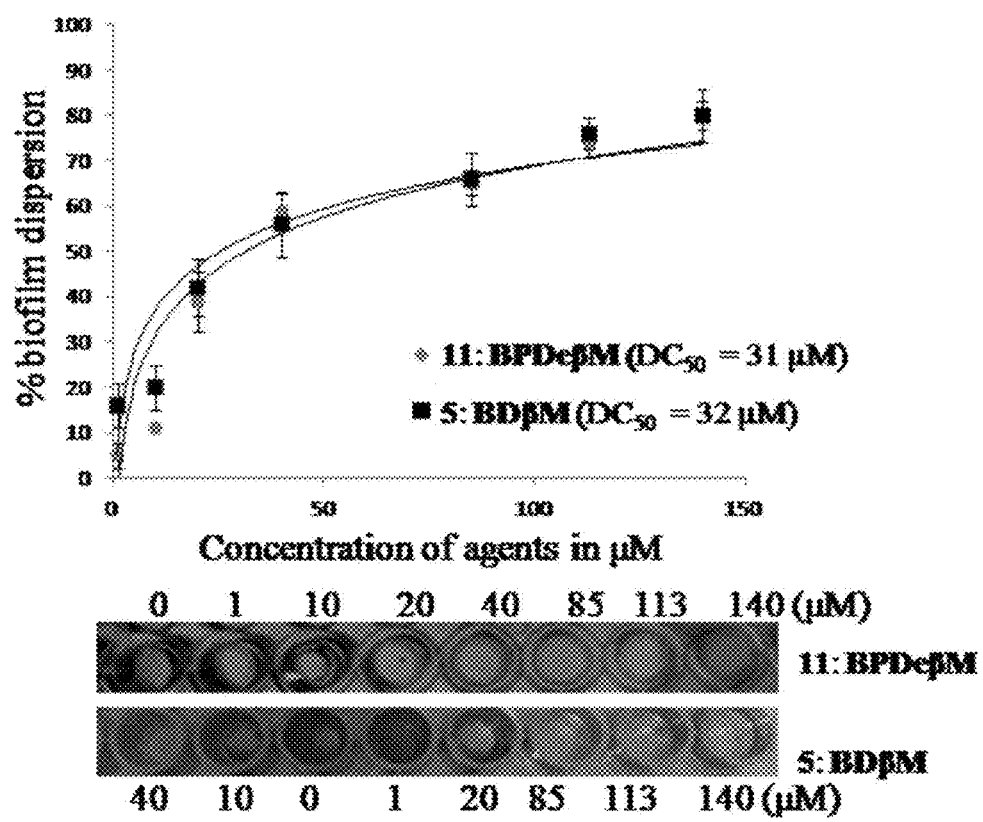
Figure 7:
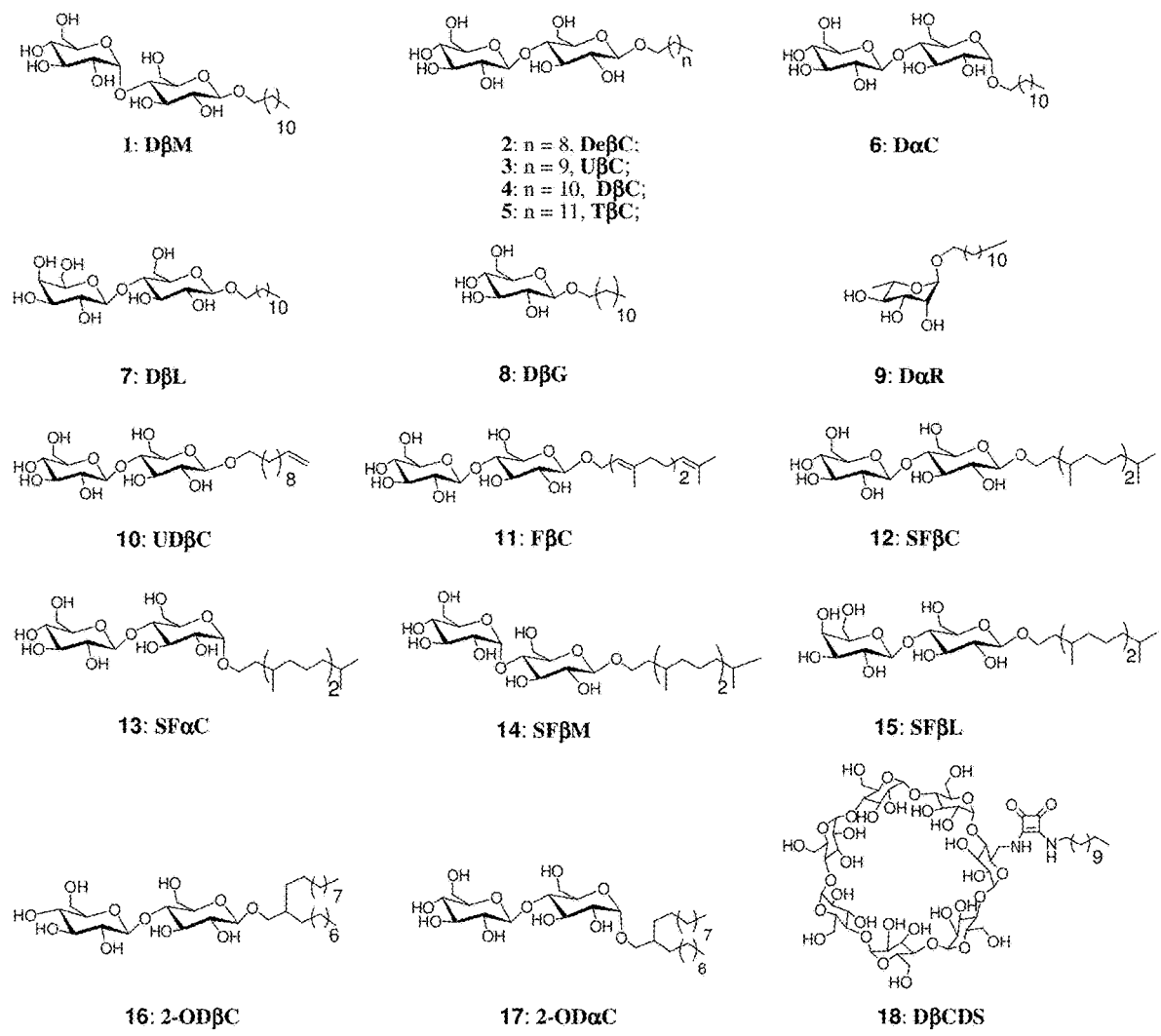
Figure 8:
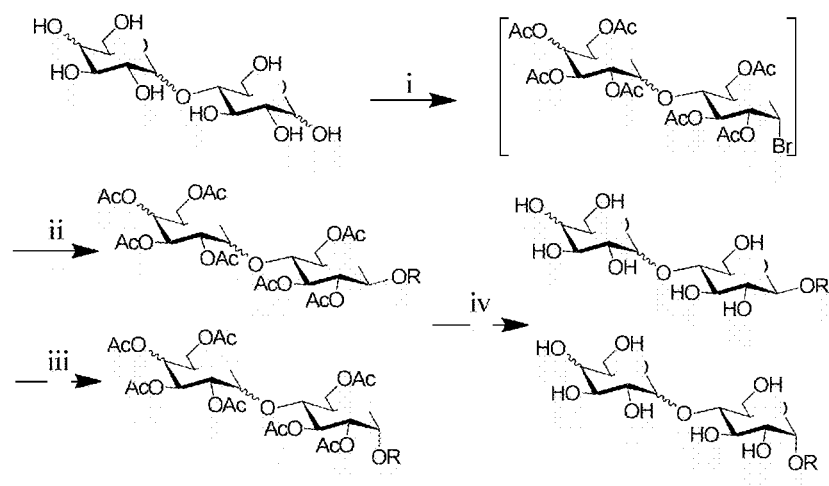
Figure 9:
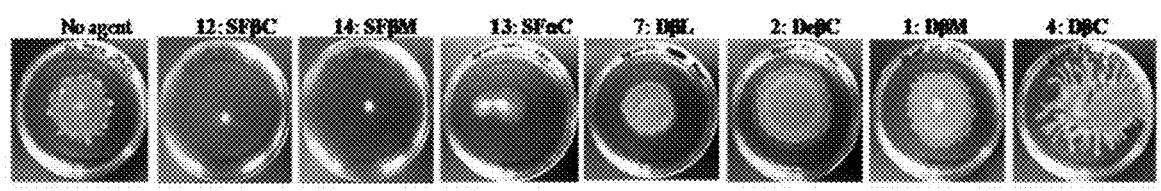
Figure 10:
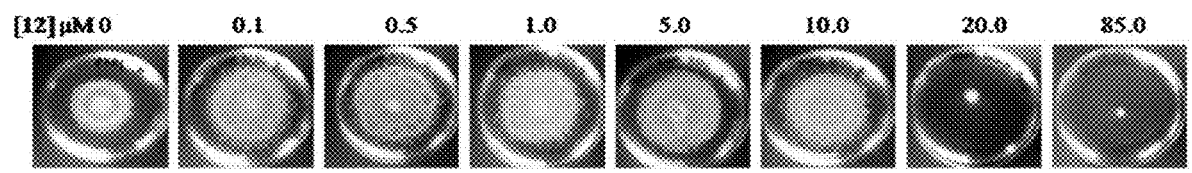
Figure 11:
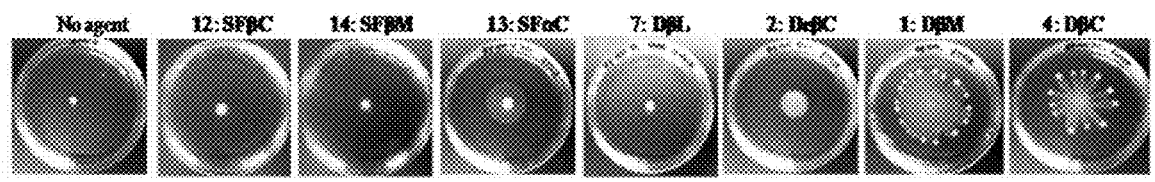
Figure 12:
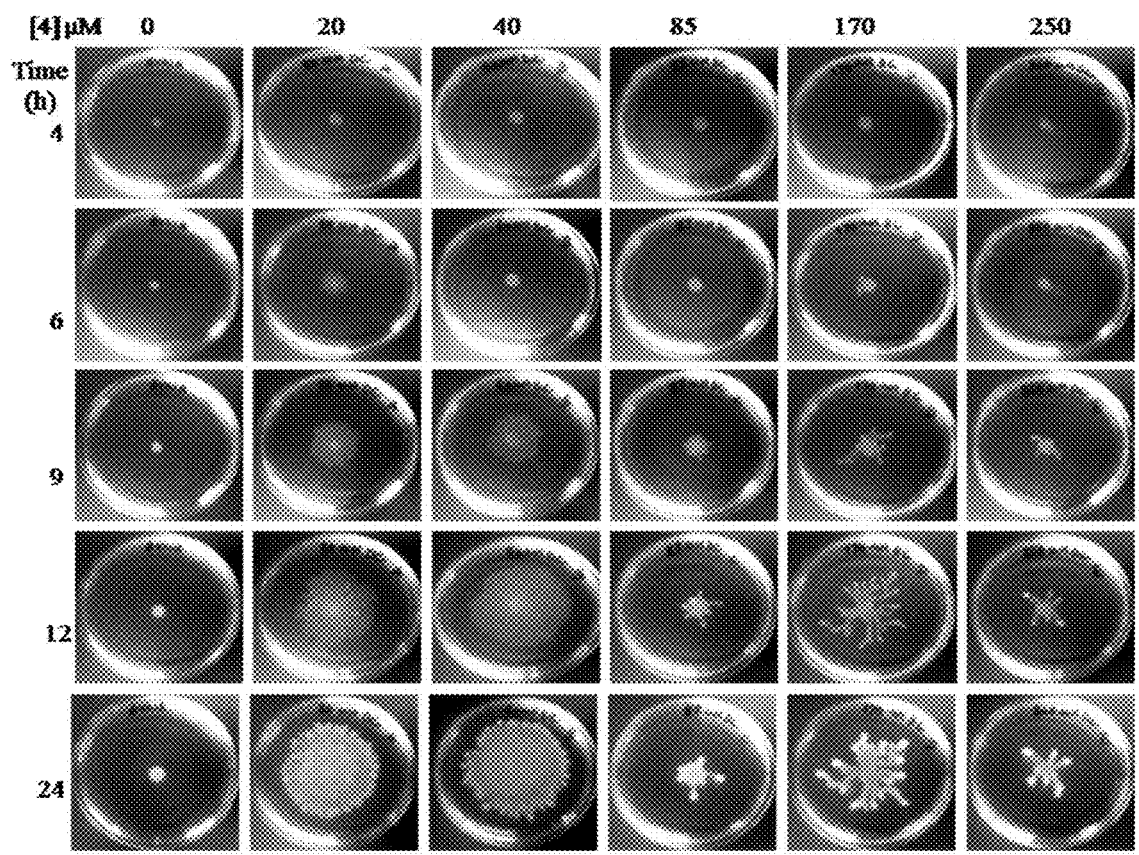
Figure 13:
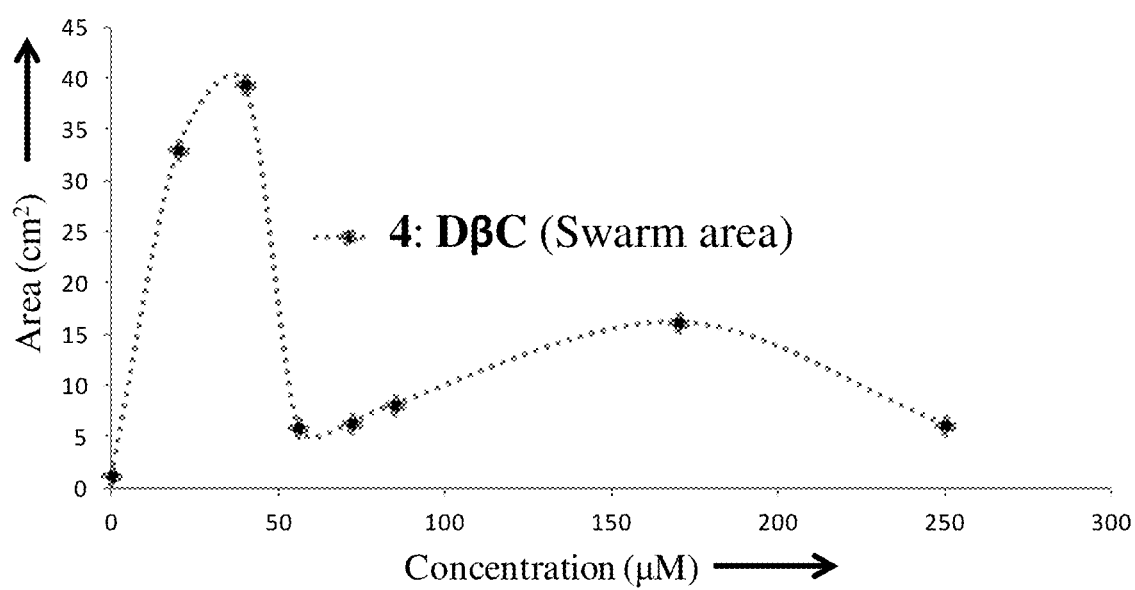
Figure 14:
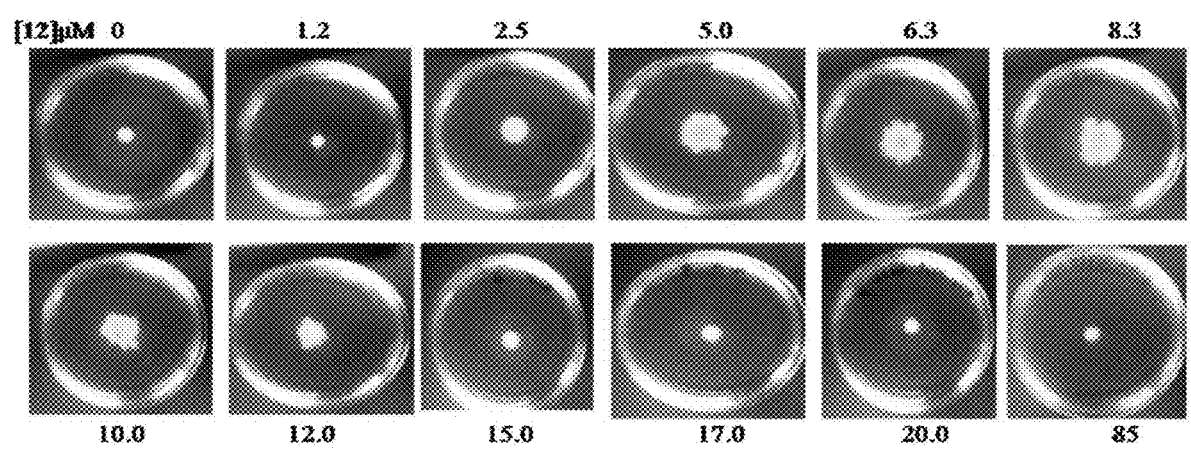
Figure 15:
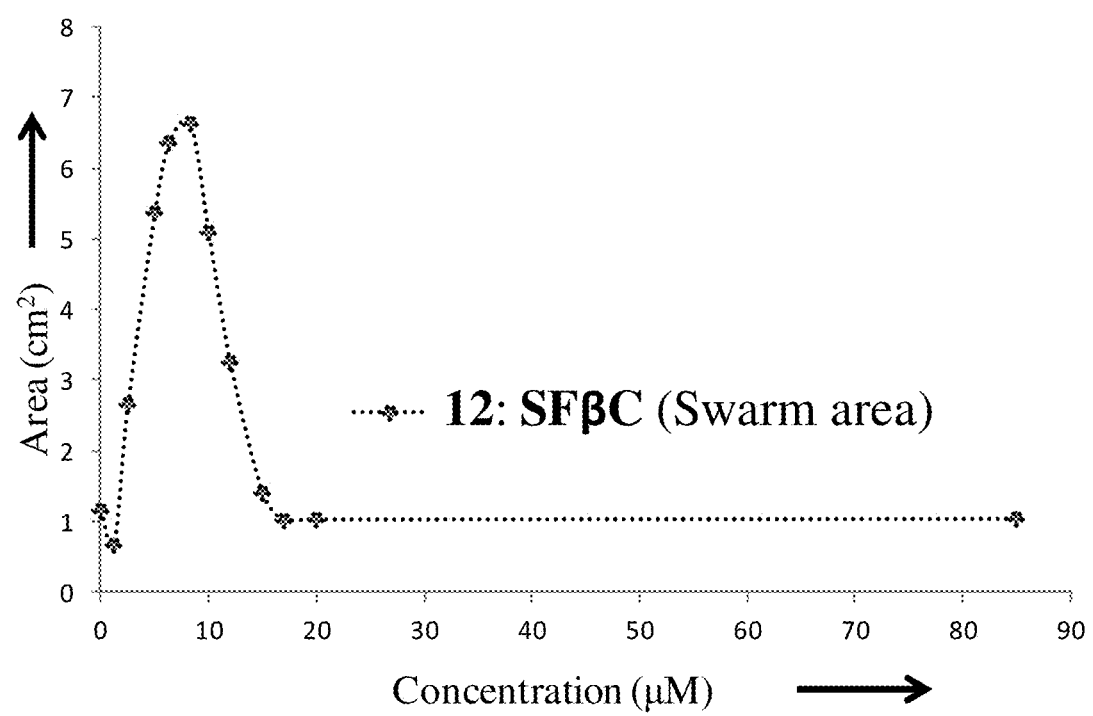
Figure 16:
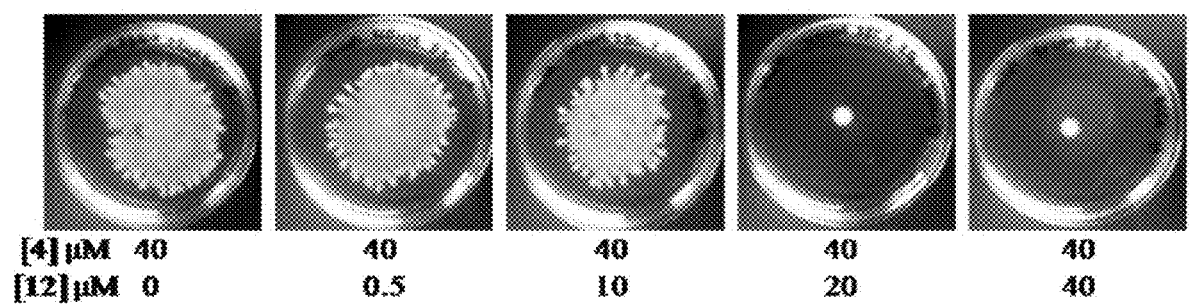
Figure 17:
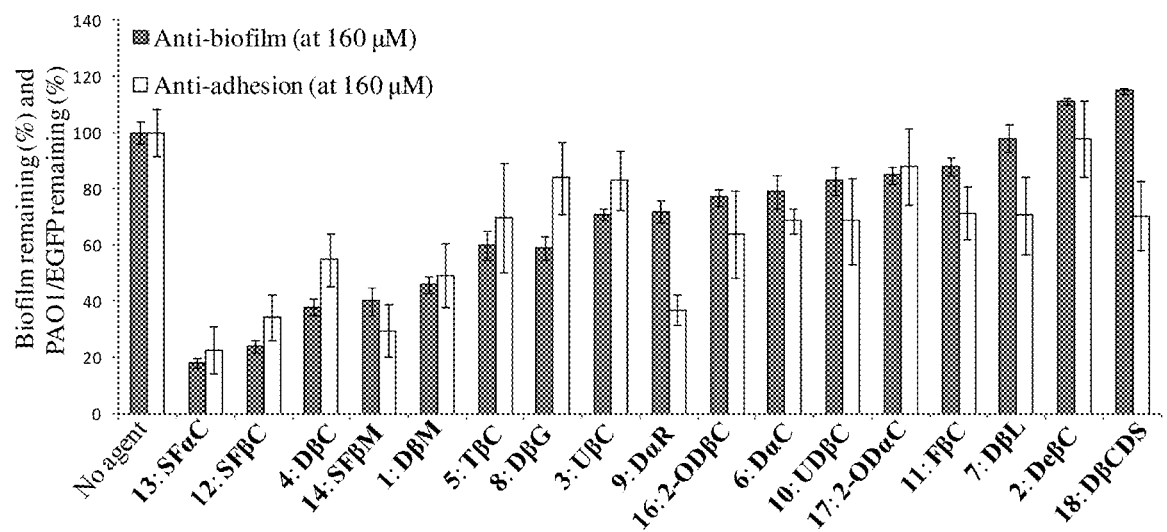
Figure 18:
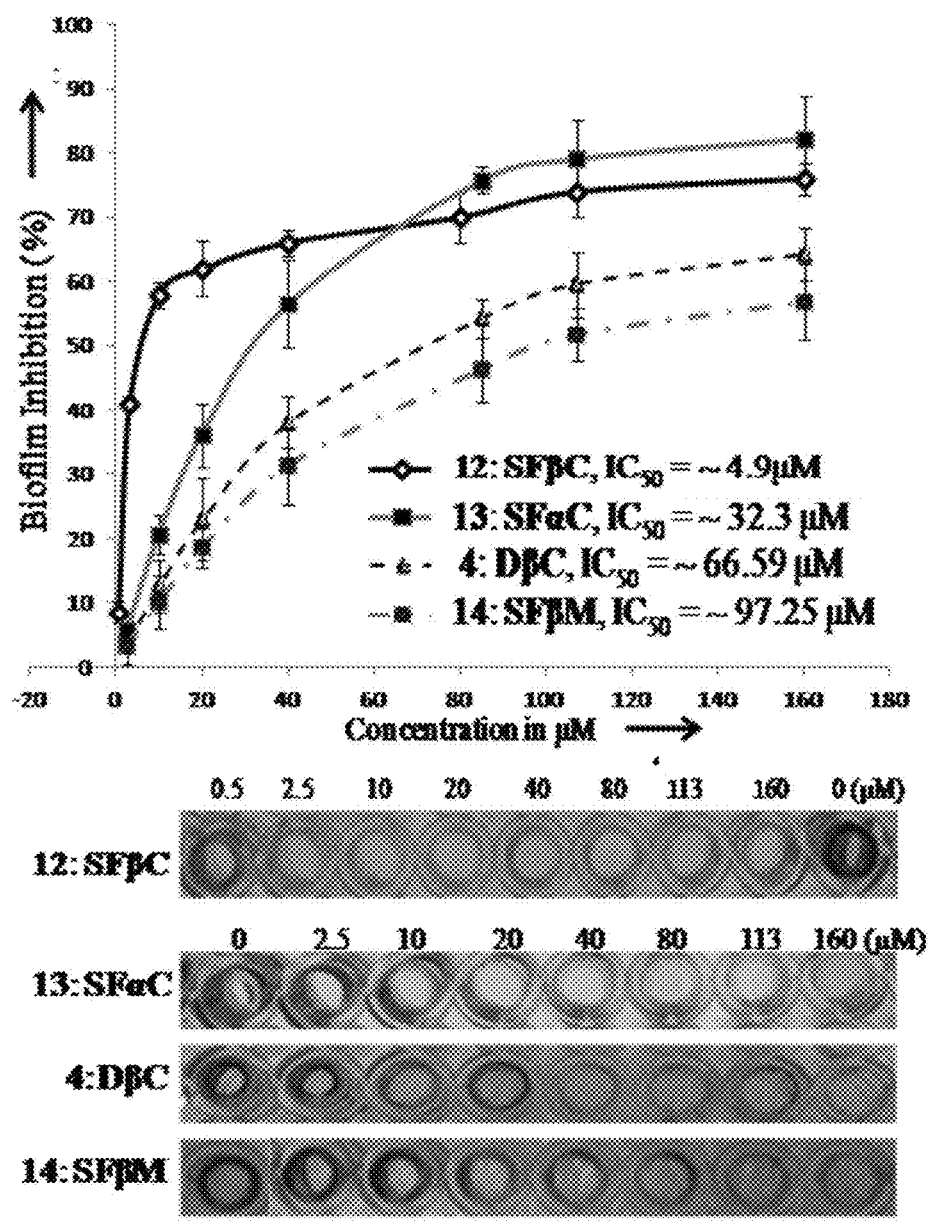
Figure 19:
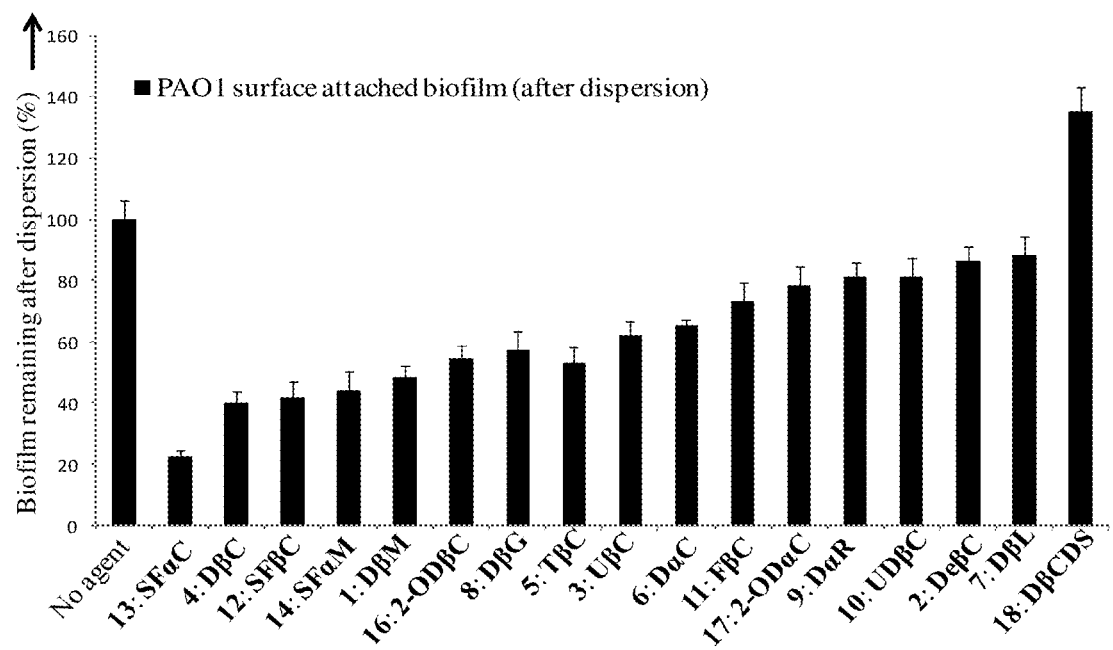
Figure 20:
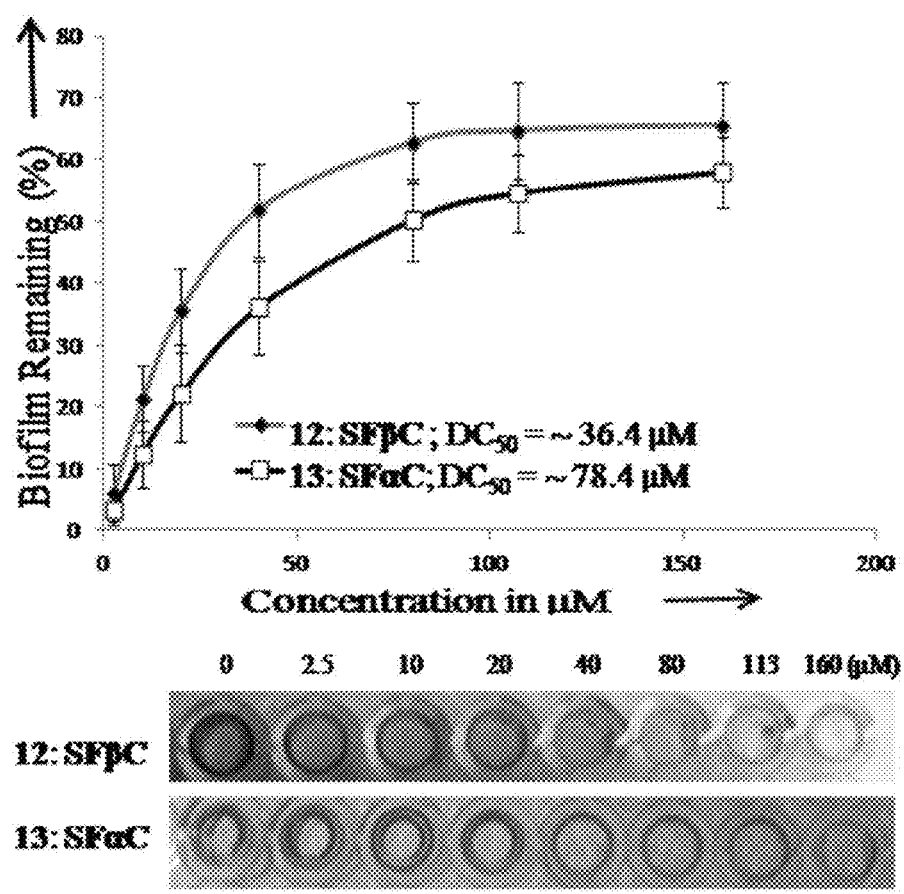
Figure 21:
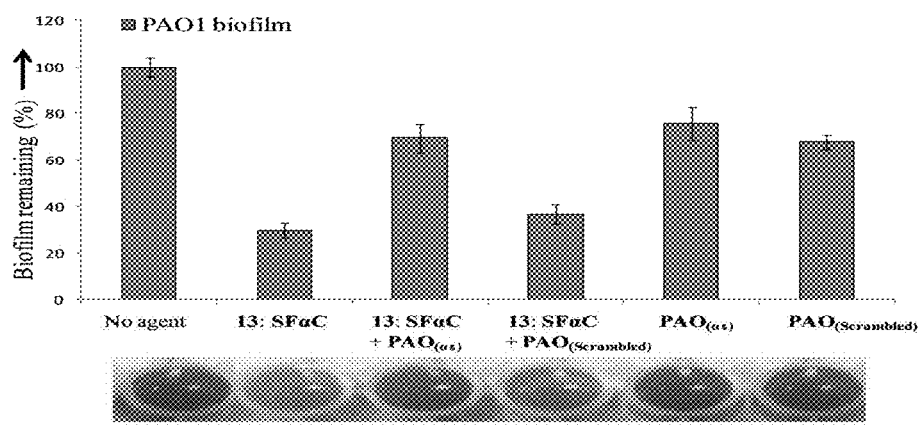
Figure 22:
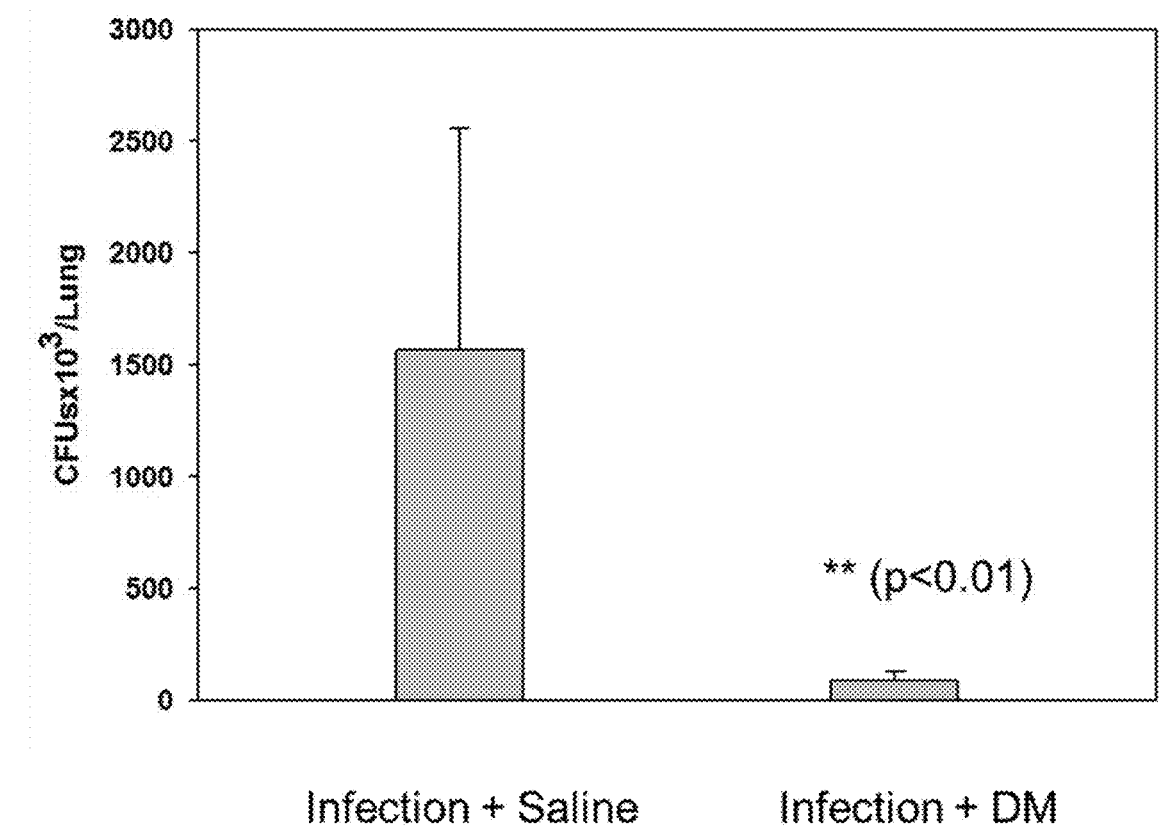

FIG. 3 is a graph of the inhibition of biofilm and adhesion by selected maltose derivatives, generic surfactants (SDS, $C_{12}EG_4OH$) at 110 µM (anti-biofilm) and 85 µM (anti-adhesion) and known anti-biofilm agent BF8 at 110 µM (anti-biofilm) and 100 µM (anti-adhesion) measured using CV dye based and fluorescence assays respectively, where the error bar is standard error of the mean from 6 replicates;

FIG. 4 is a graph of the dose response curve and biofilm inhibition $IC_{50}$ values for compounds 11: BPDeβM and 5: BDβM using CV dye based biofilm inhibition assay, where the error bar is standard error of the mean from 6 replicates;

FIG. 5 is a graph of the dispersion of PAO1 biofilm with different maltose derivatives at 110 µM as quantified by CV dye based assay, where the error bar is standard error of the mean from 6 replicates;

FIG. 6 is a graph of the dose response curve and biofilm dispersion $DC_{50}$ values for compounds 11: BPDeβM and 5: BDβM using crystal violet dye based biofilm inhibition assay, where the error bar is standard error of the mean from 6 replicates;

FIG. 7 is a series of chemical diagrams of disaccharide hydrocarbons and β-cyclodextrin derivatized hydrocarbon;

FIG. 8 is a schematic showing the general synthetic scheme for disaccharide hydrocarbons (DSHs); i) AcBr/AcOH, rt or 60° C., ~1 h; ii) ROH, $FeCl_3$ or $Hg(CN)_2$, MeCN, rt, ~1 h; iii) ROH, $FeCl_3$, $MeNO_2$, rt, ~1 h; iv) MeONa/MeOH, ~12 h, $H^+$ amberlite resin, Neutralize, (pH 6.5);

FIG. 9 is a series of images of swarm (~0.5% agar) plates inoculated with PAO1 after ~24 hours with (at 110 µM) and without agents (DSHs);

FIG. 10 is a series of images of swarm (~0.5% agar) plates with increasing concentration of 12: SFβC. Images taken 24 h after inoculation with PAO1;

FIG. 11 is a series of images of swarm (~0.5% agar) plates inoculated with non-swarming PA mutant, rhlA after ~24 hours with (at 110 µM) and without agents (DSHs);

FIG. 12 is a series of images of swarm (~0.5% agar) plates containing increasing concentration of 4: DβC at different times after inoculation with non-swarming PA mutant rhlA;

FIG. 13 is a graph of rhlA swarm area (after 24 h) on soft agar (~0.5%) versus concentration of 4: DβC;

FIG. 14 is a series of images of swarm (~0.5% agar) plates with increasing concentration of 12: SFβC with images taken 24 h after inoculation with non-swarming PA mutant rhlA;

FIG. 15 is a graph of rhlA swarm area (after 24 h) on soft agar (~0.5%) versus concentration of 12: SFβC FIG. 16 is a series of images of swarm (~0.5% agar) plates containing constant concentration of 4: DβC but increasing concentration of 12: SFβC after 12 h of inoculation with non-swarming PA mutant rhlA;

FIG. 17 is a graph of the percent surface attached PAO1 biofilm remaining within the wells of microtiter plate after biofilm was allowed to develop for 24 hours with or without various agents. Bacterial culture media: Luria-Bertani (LB). Percent PAO1/EGFP adhered on polystyrene surface. Resultant concentration of each agent within wells ~160 μM;

FIG. 18 is a graph of the dose-response curve along with a series of images of microtiter plates after CV-dye based inhibition assay;

FIG. 19 is a graph of percent surface attached PAO1 biofilm remaining within the wells of microtiter plate after biofilm was allowed to develop for 24 hours without any agents and then treated with various agents for another 24 hours. Resultant concentration of each agent within wells ~160 μM;

FIG. 20 is a graph of a dose-response curve and images of microtiter plates after CV-dye based dispersion assay;

FIG. 21 is a graph of surface attached PAO1 biofilm remaining within the wells of the microtiter plate after biofilm was allowed to develop for 24 hours with or without the agents along with images showing the concentration of agents in the wells; 13: SFαC=85 μM; PAO$_{(ox)}$=85 μM; PAO$_{(scrambled)}$=85 μM;

FIG. 22 is a graph of the effect of Dodecyl Maltoside (DM) on the bacterial clearance in mouse *P. aeruginosa* pneumonia.

Figure 23:
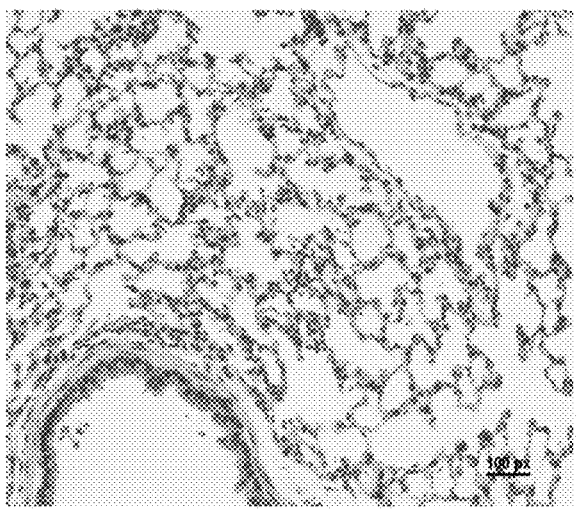
Figure 23:
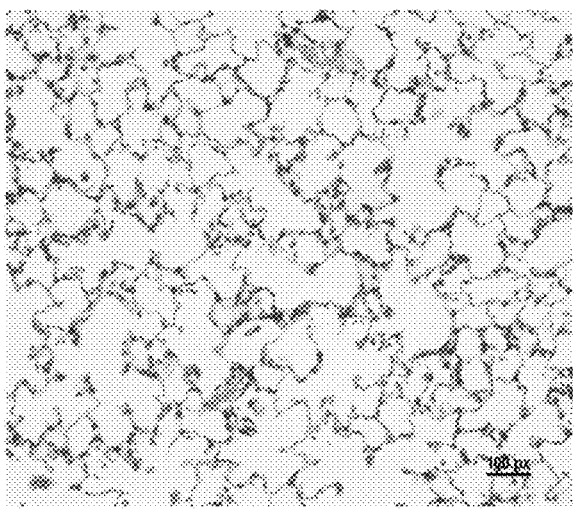

FIG. 23 is a series of micrographs of the histological analysis of representative hematoxylin and eosin-stained lung tissue sections from *P. aeruginosa* pneumonia model.

Figure 24A:
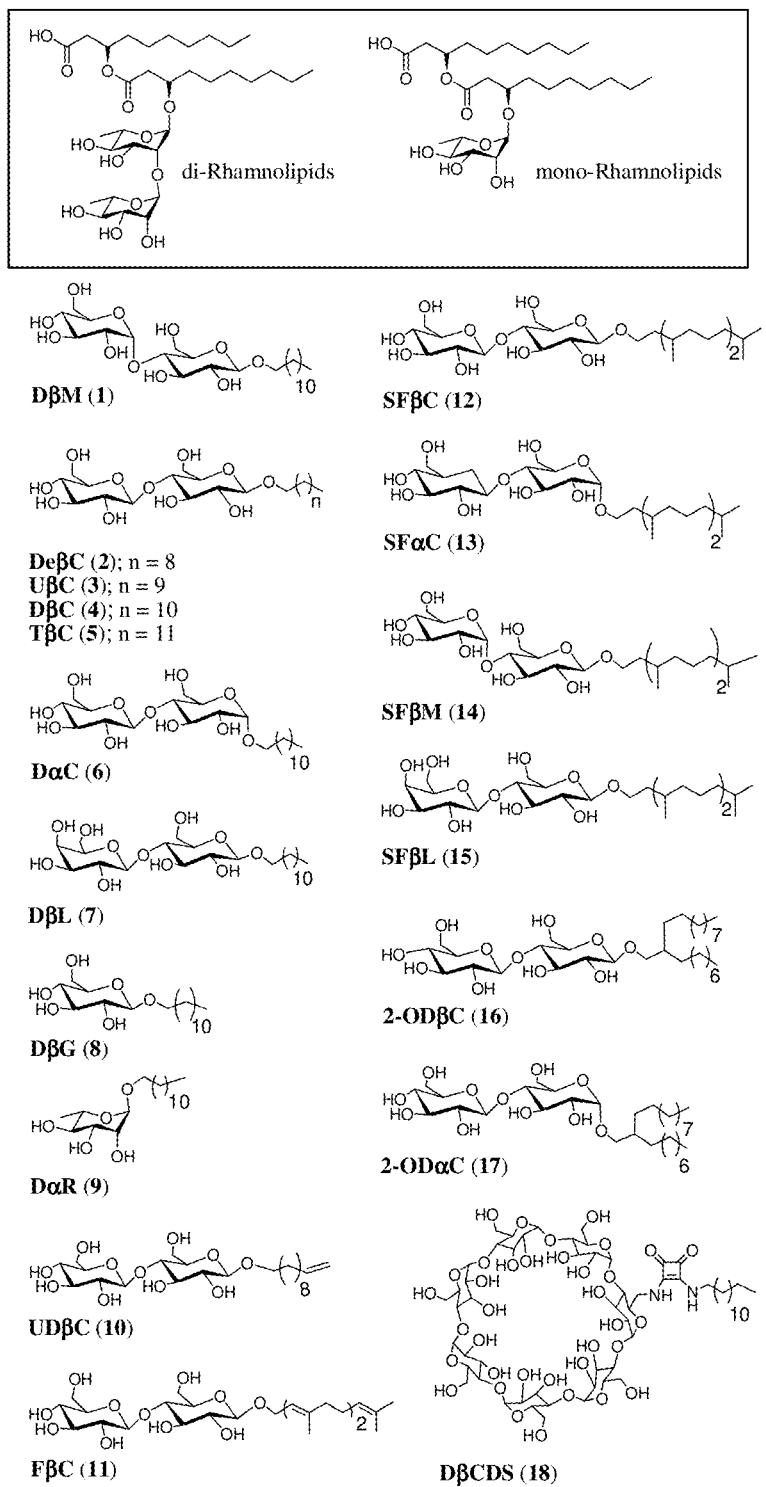
Figure 24B:
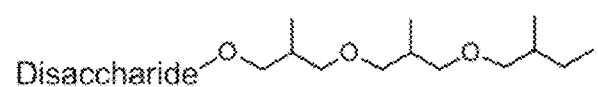
Figure 24B:
Figure 24B:
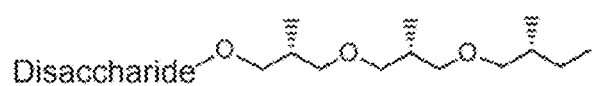
Figure 24B:
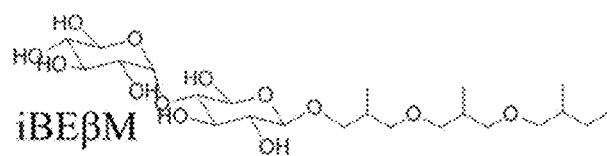
Figure 24B:
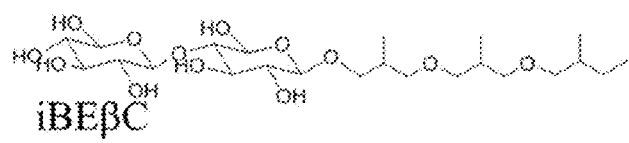
Figure 24B:
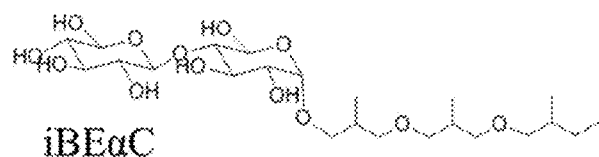
Figure 25:
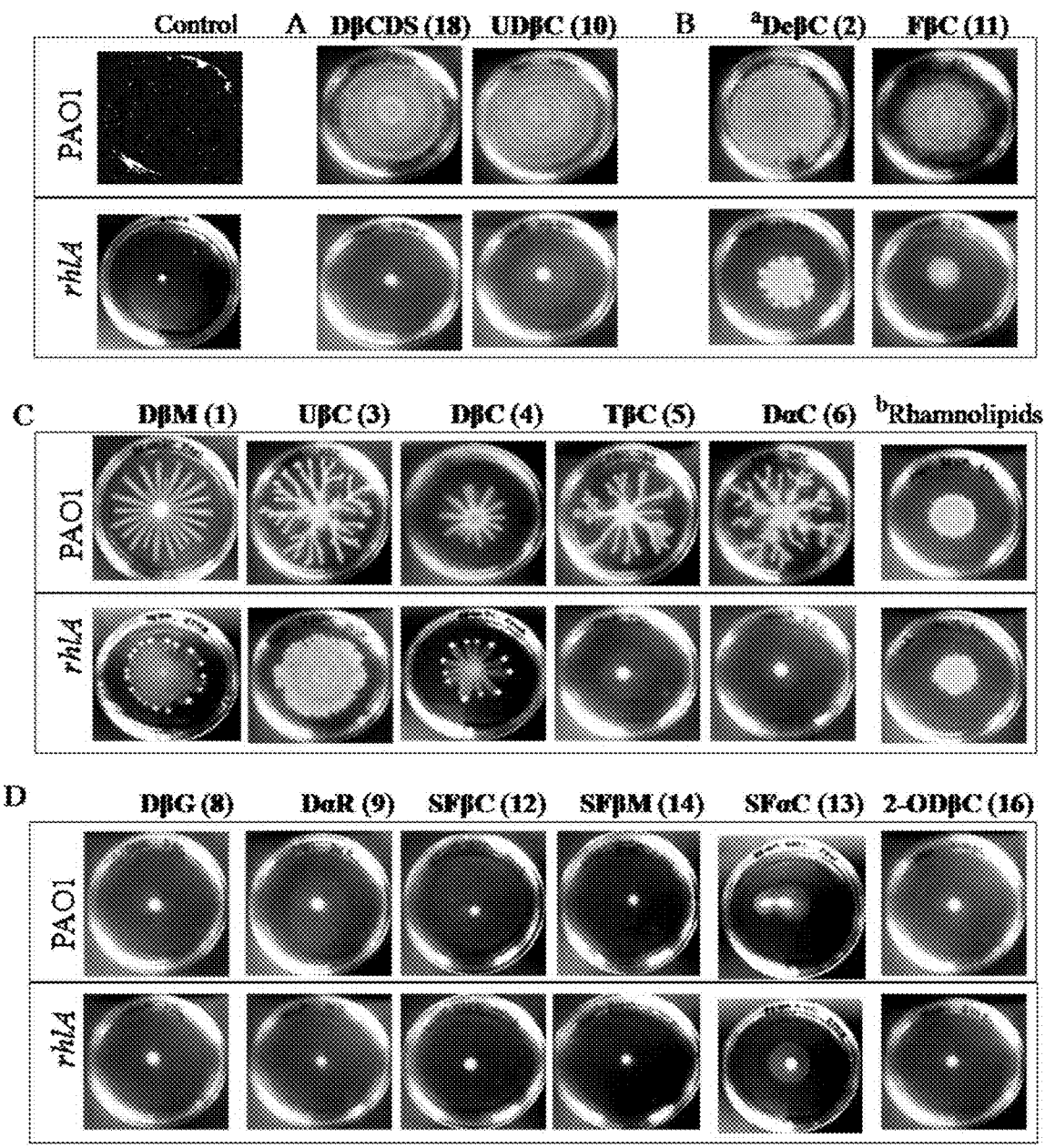

FIGS. 24A and 24B are a series of schematics of structures of synthetic saccharide-based hydrocarbons that include maltose, cellobiose, lactose, rhamnose, and β-cyclodextrin-based stereochemistries; and hydrocarbons derived from farnesol molecules, and "saturated" farnesols, and the structure of di-rhamnolipid and mono-rhamnolipid is also shown;

FIG. 25 is a series of images of swarming motility of wild type PAO1 and rhlA mutant on soft agar plates (~0.5% agar, M8 media) supplemented with ~85 μM DSHs. Images were taken 24 h after inoculation with bacteria. $^{a}$Concentration of DeβC (2) was 160 μM; $^{b}$Rhamnolipids concentration ~30 μM for PAO1 and ~10 μM for rhlA.

Figure 26:
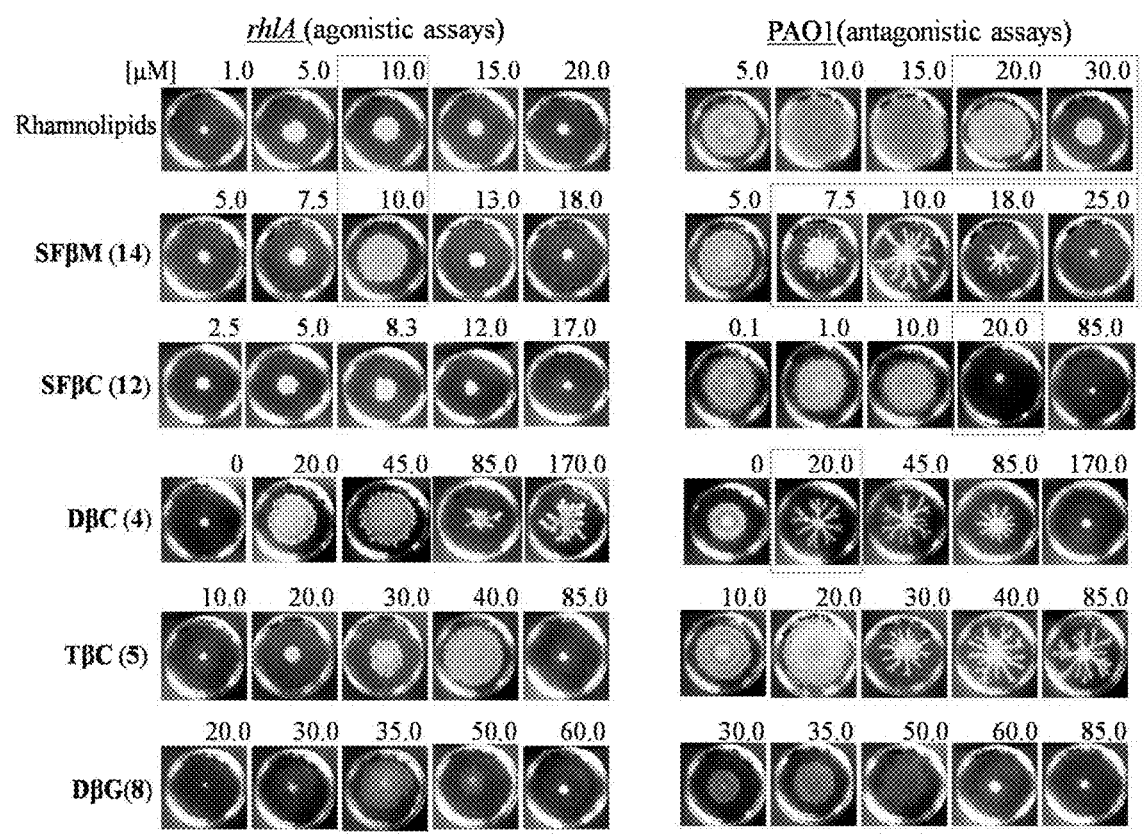
Figure 27:
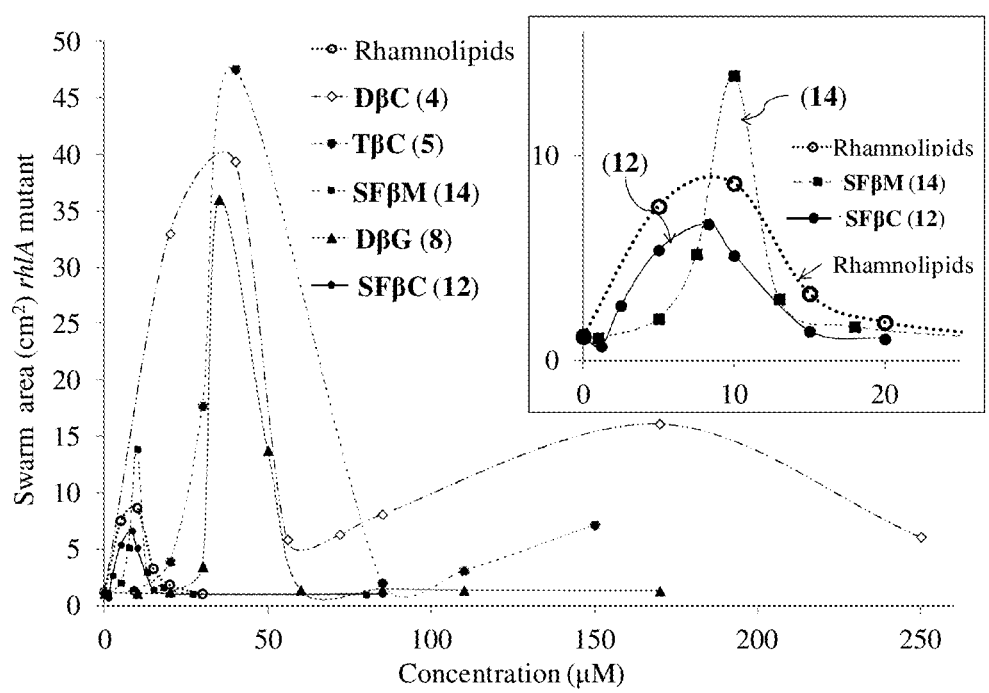
Figure 28:
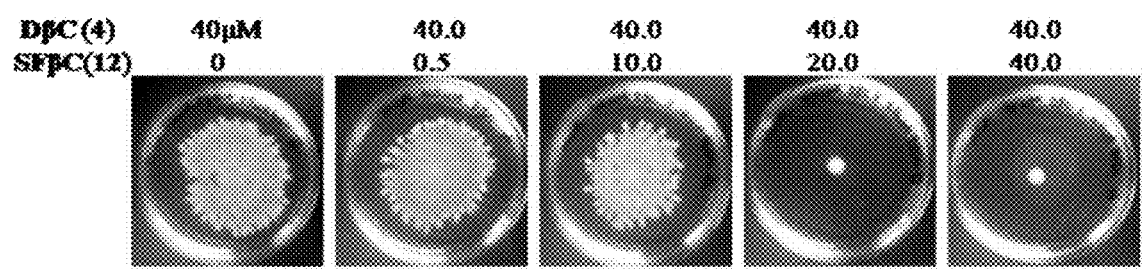
Figure 29:
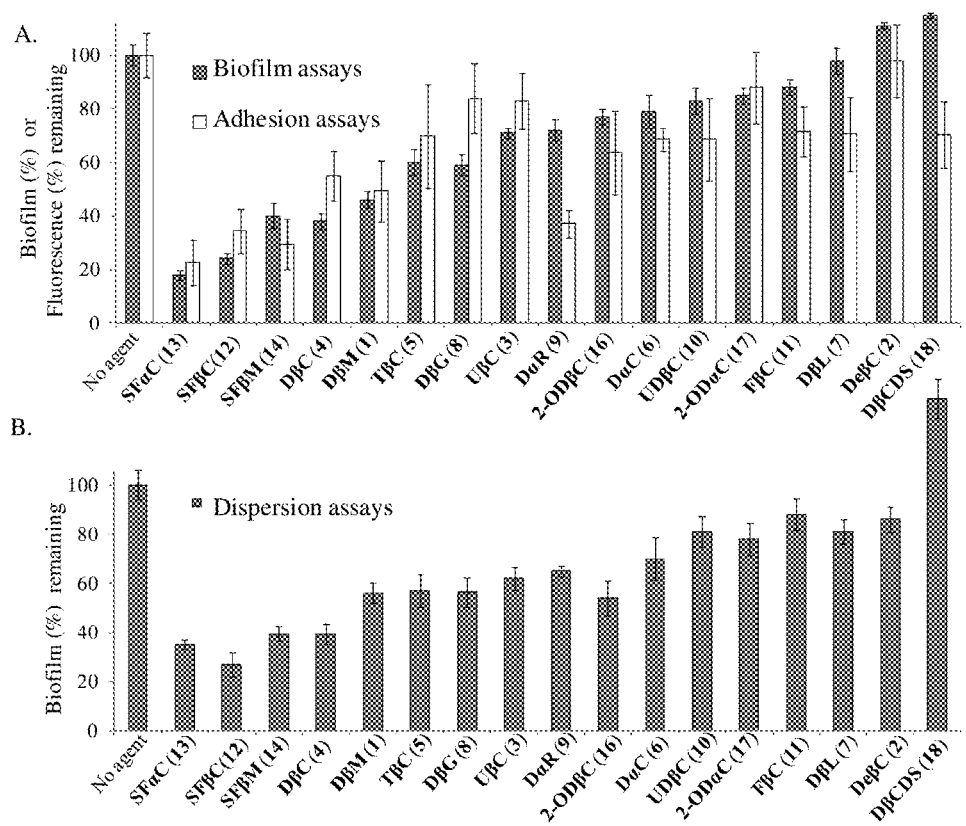
Figure 30:
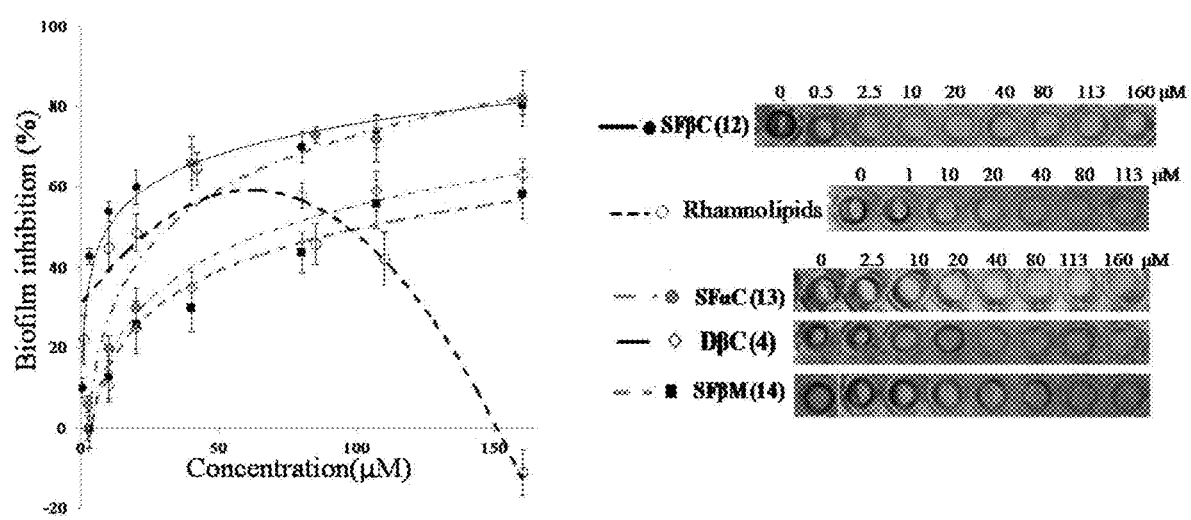
Figure 31:
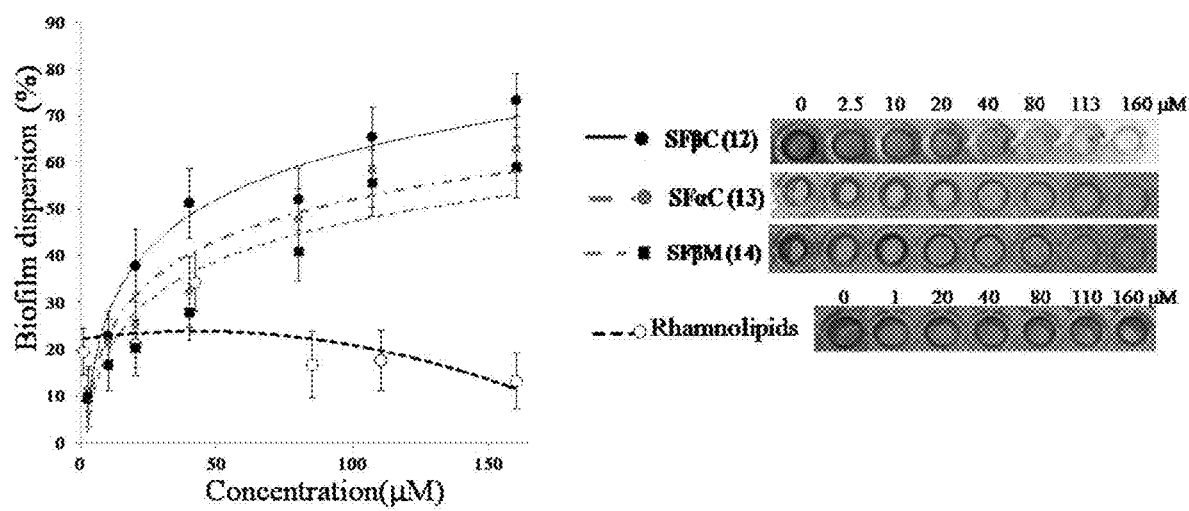
Figure 32:
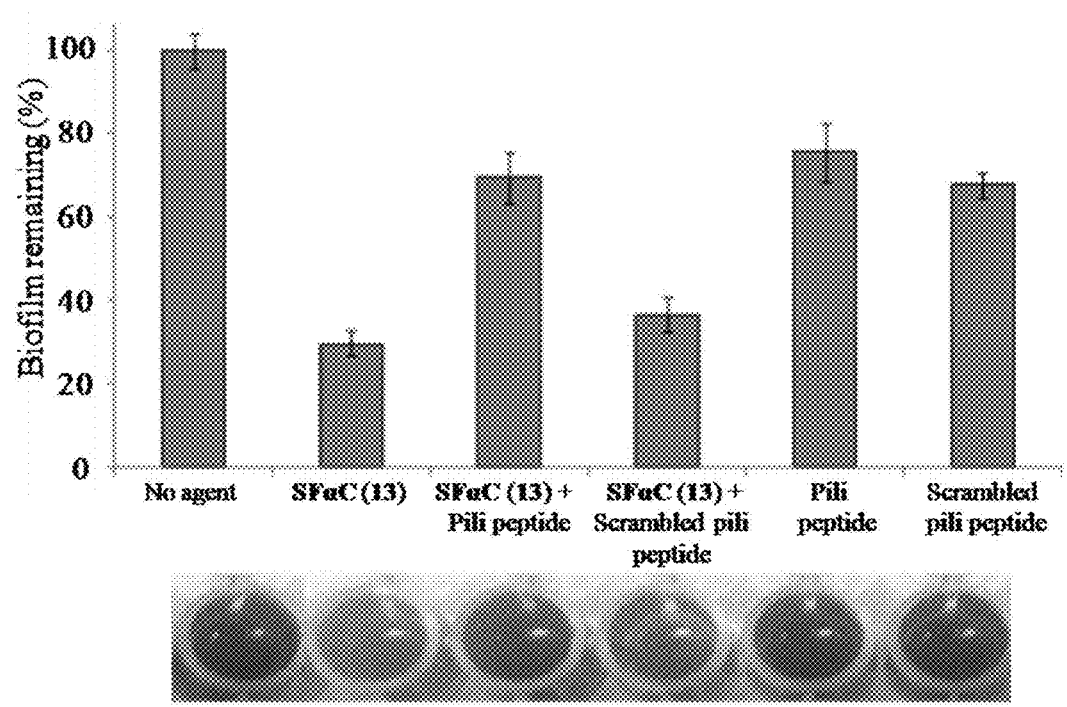
Figure 33:
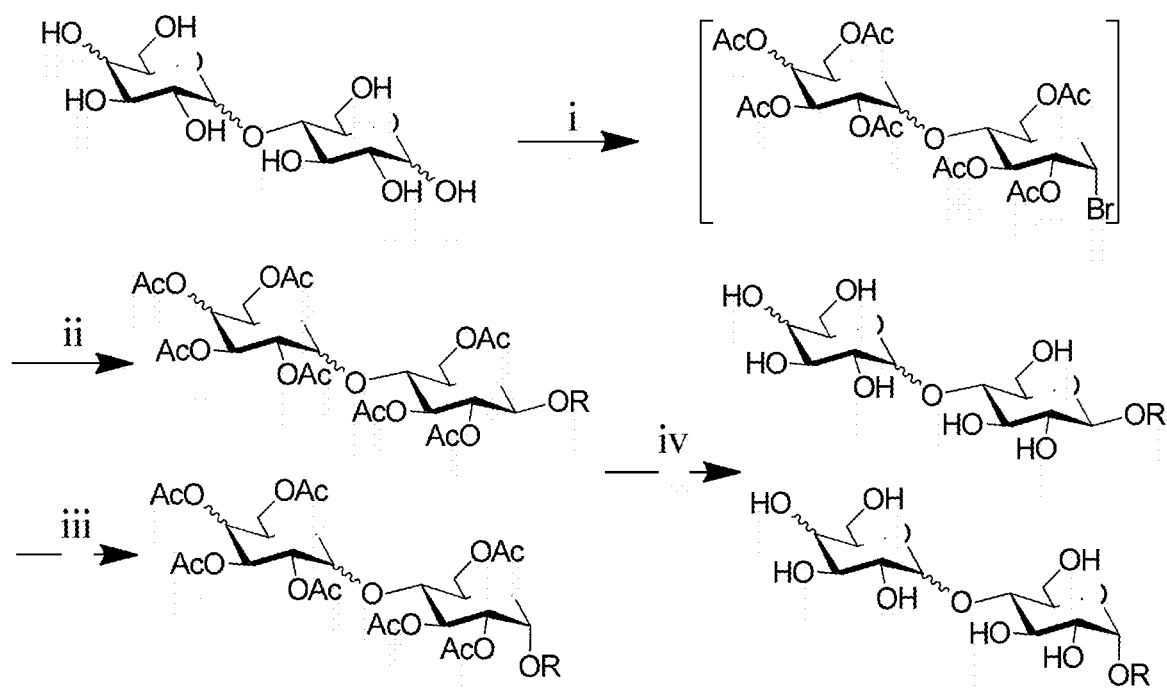
Figure 34:
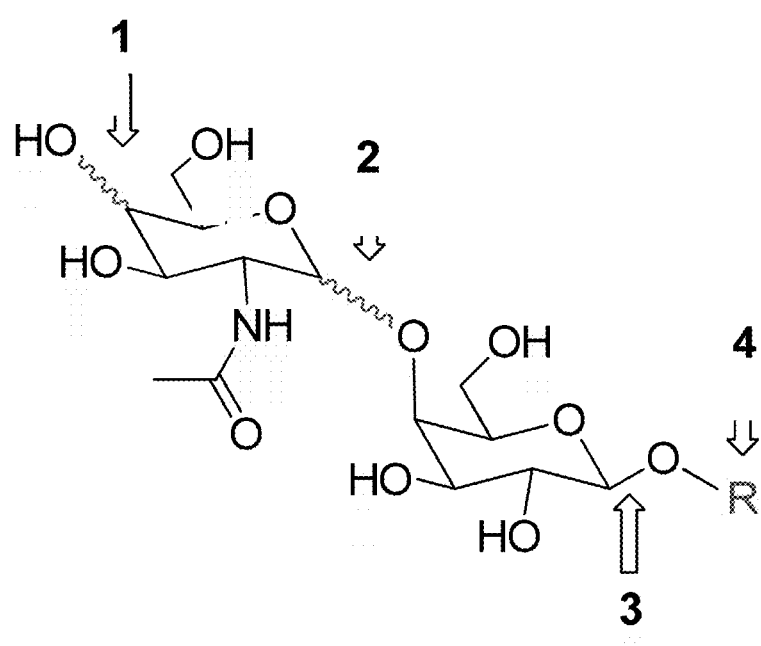
Figure 35A:
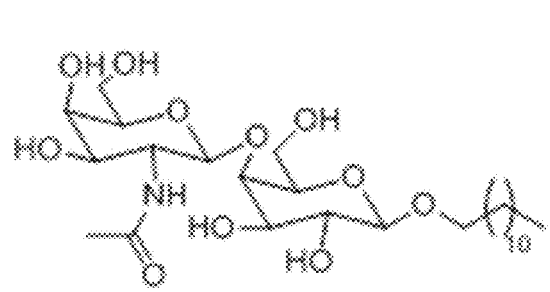
Figure 35A:
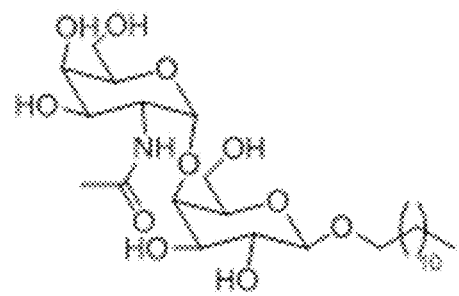
Figure 35A:
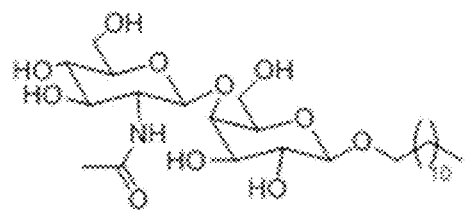
Figure 35A:
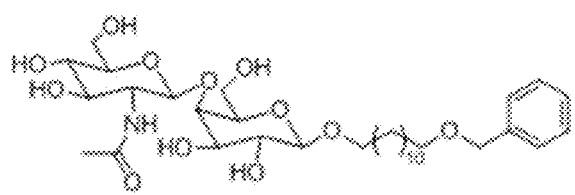
Figure 35B:
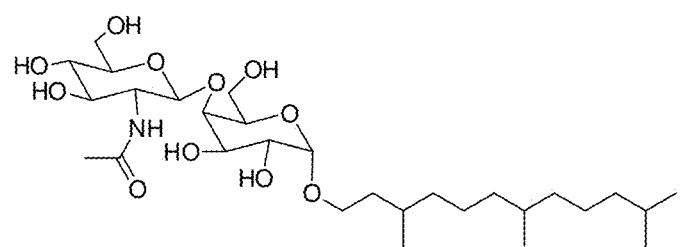
Figure 35B:
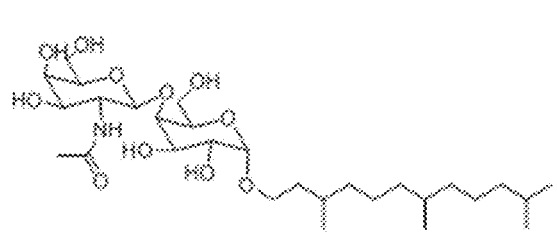
Figure 35B:
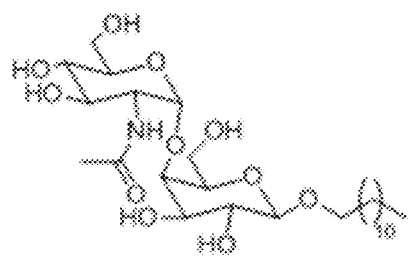
Figure 35B:
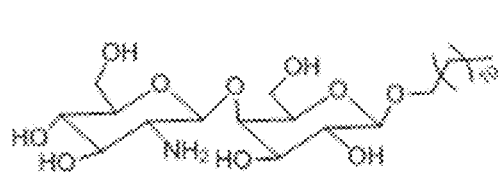
Figure 35B:
Figure 36:
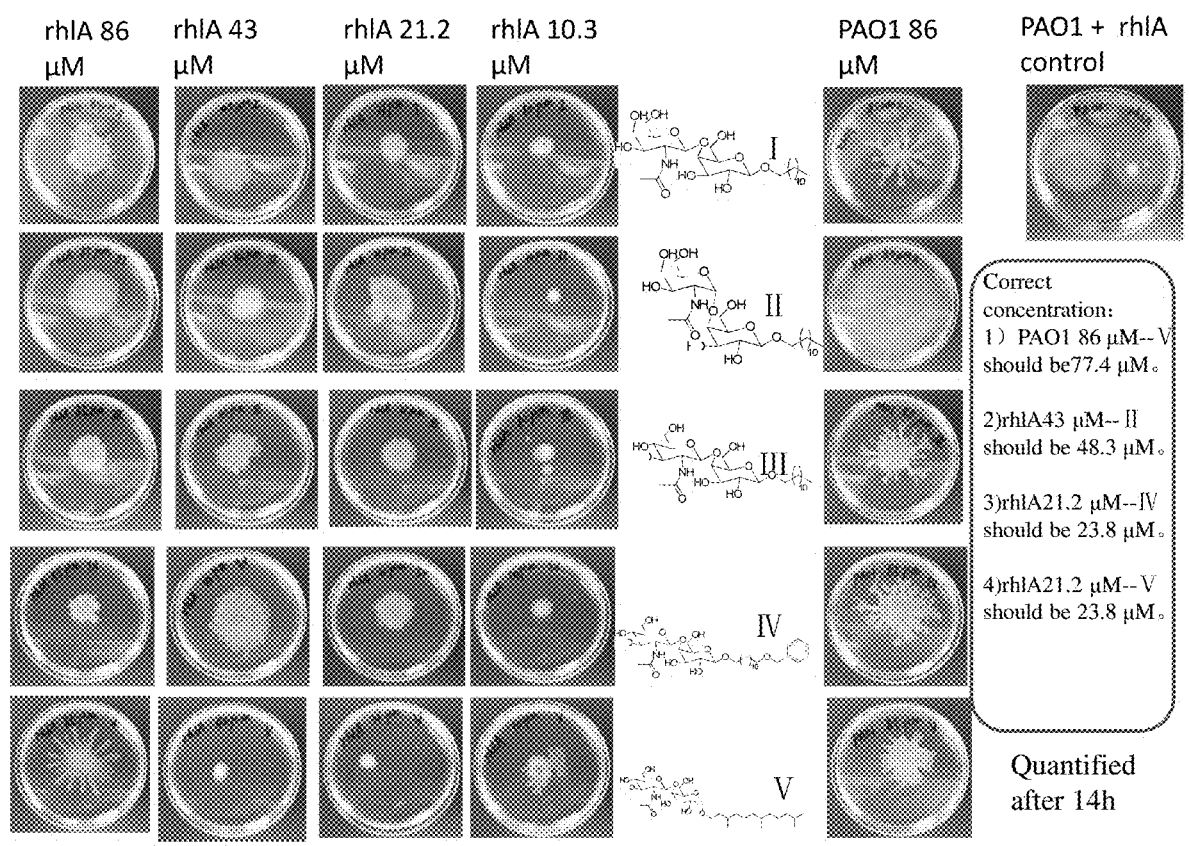
Figure 37:
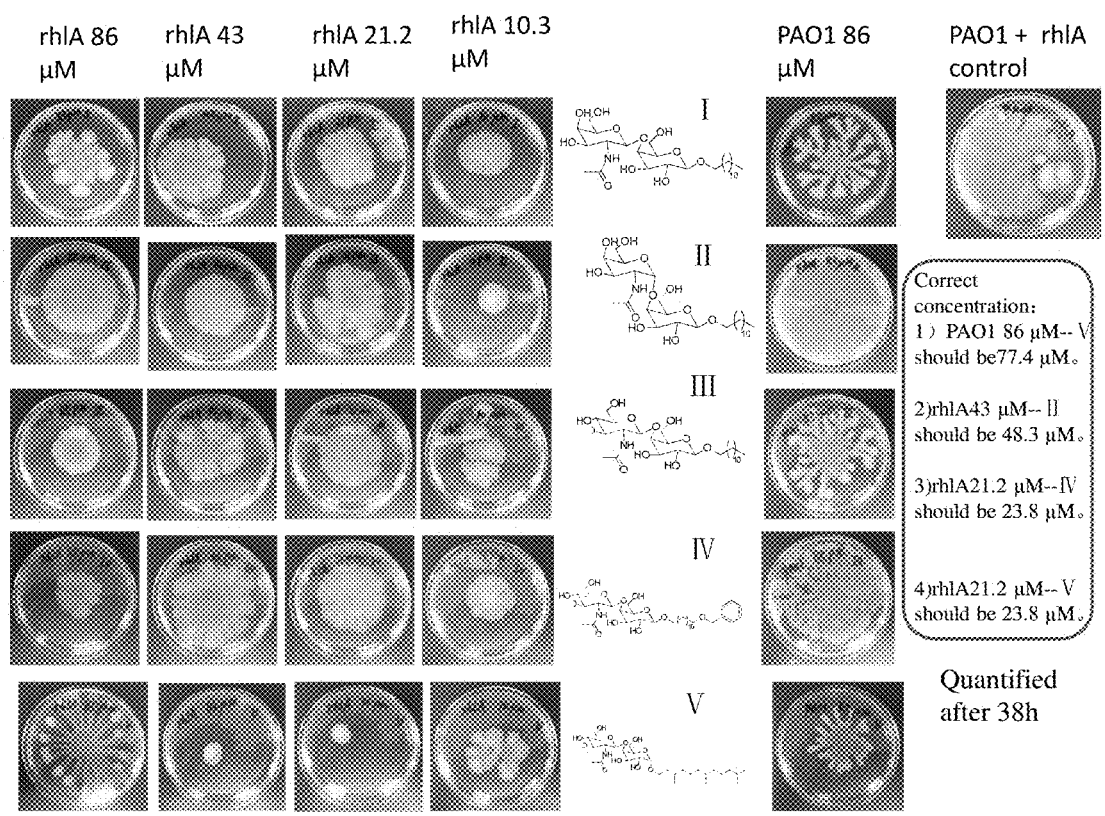
Figure 38:
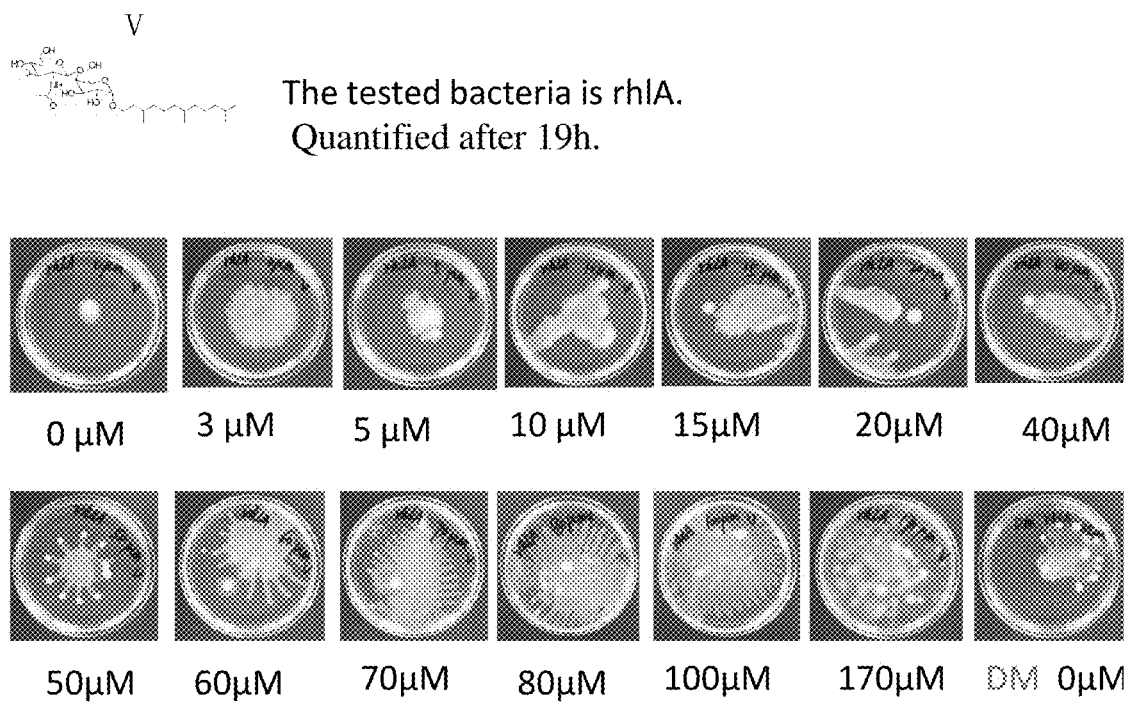
Figure 39:
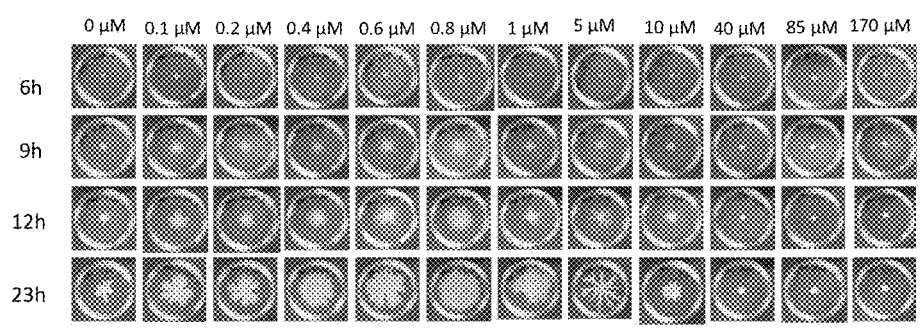
Figure 40:
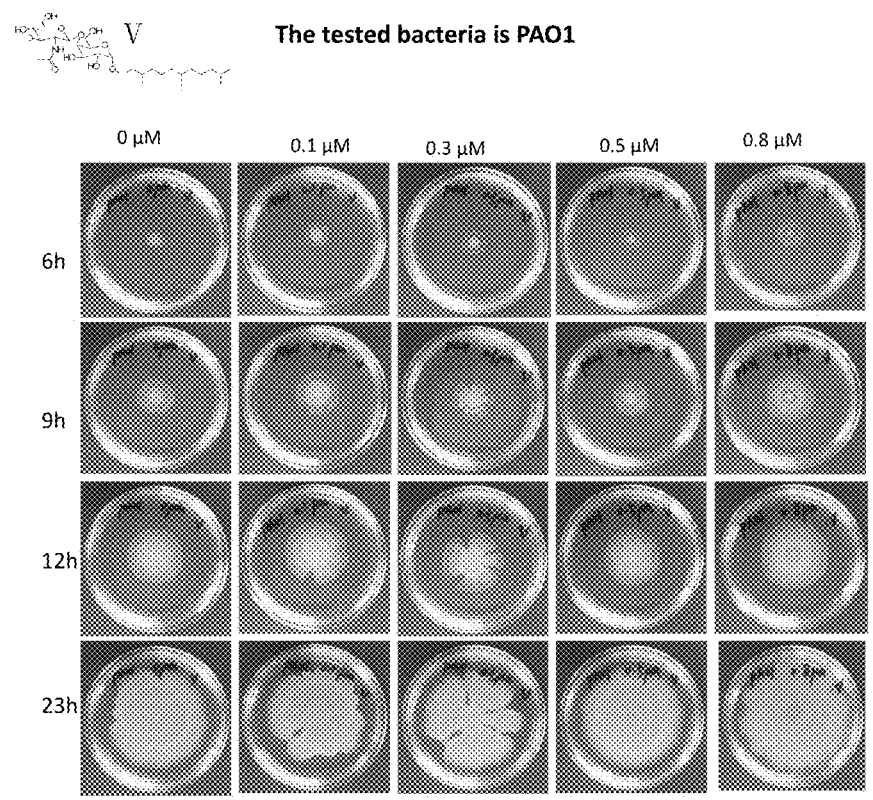
Figure 41:
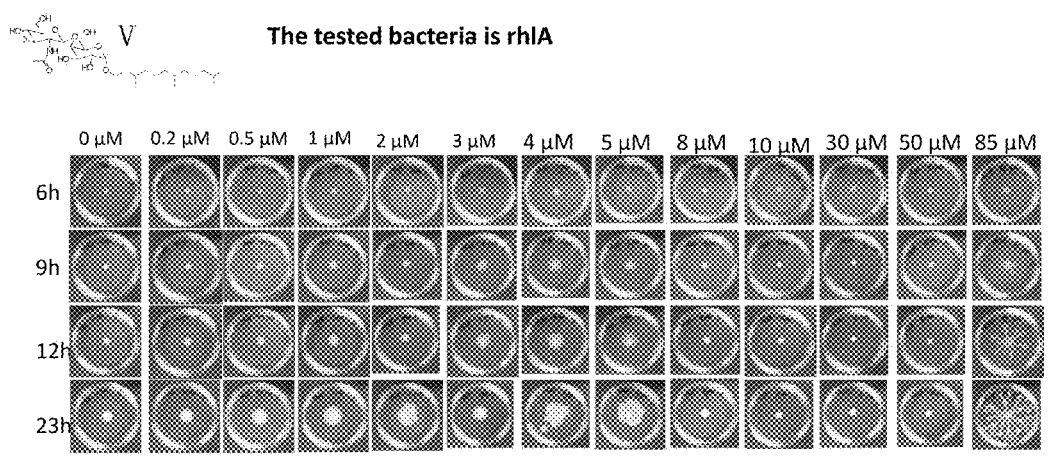
Figure 42:
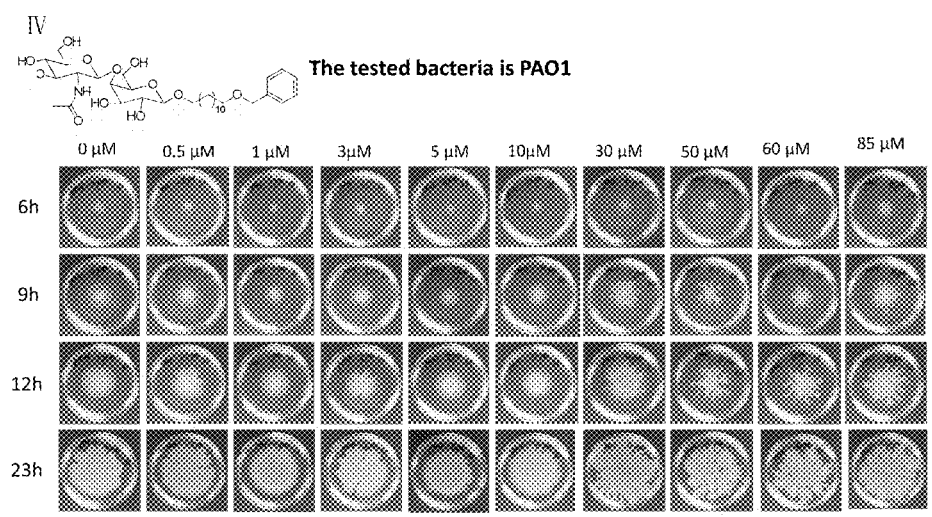
Figure 43:
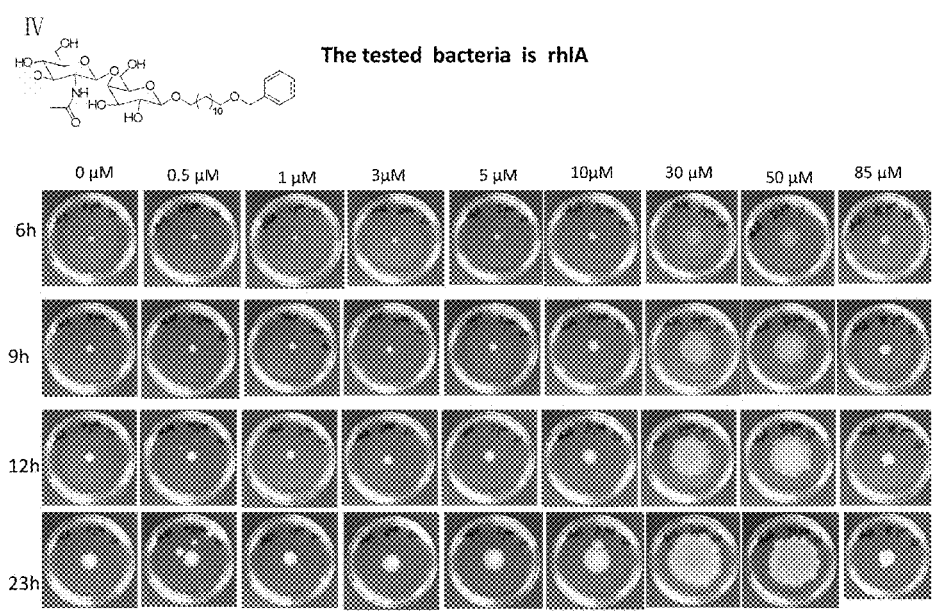
Figure 44:
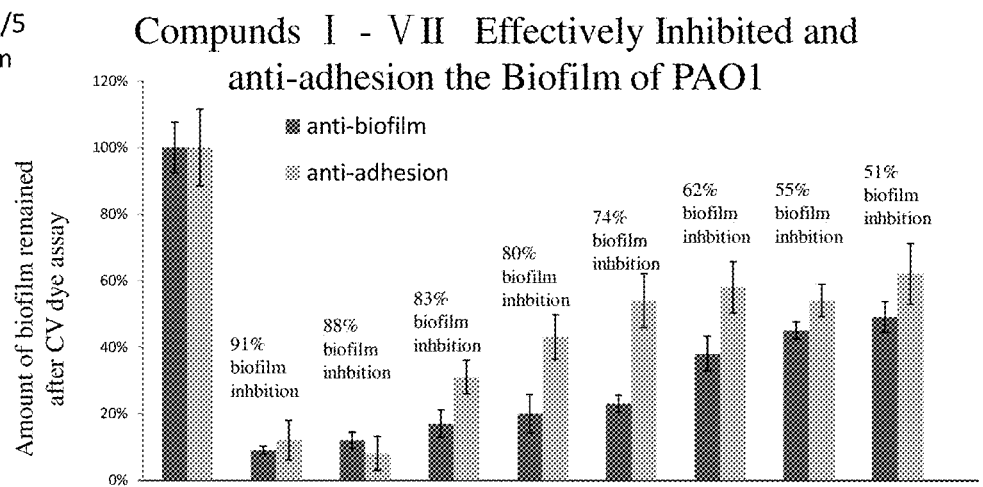
Figure 44:
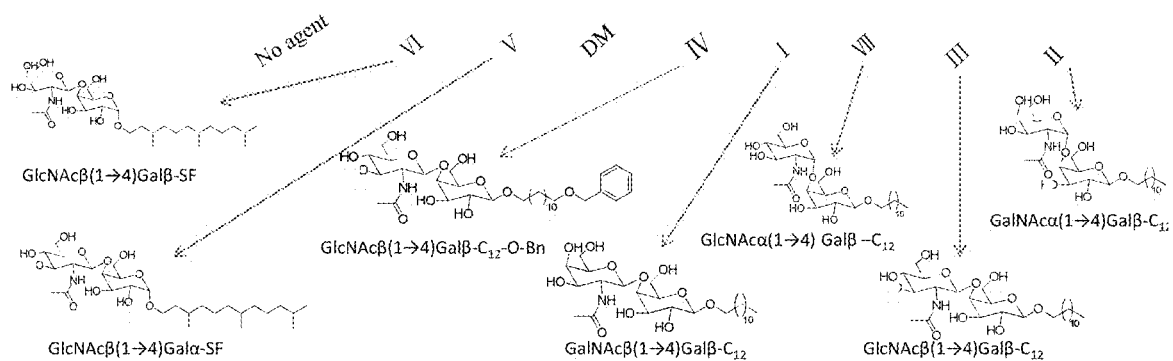
Figure 45:
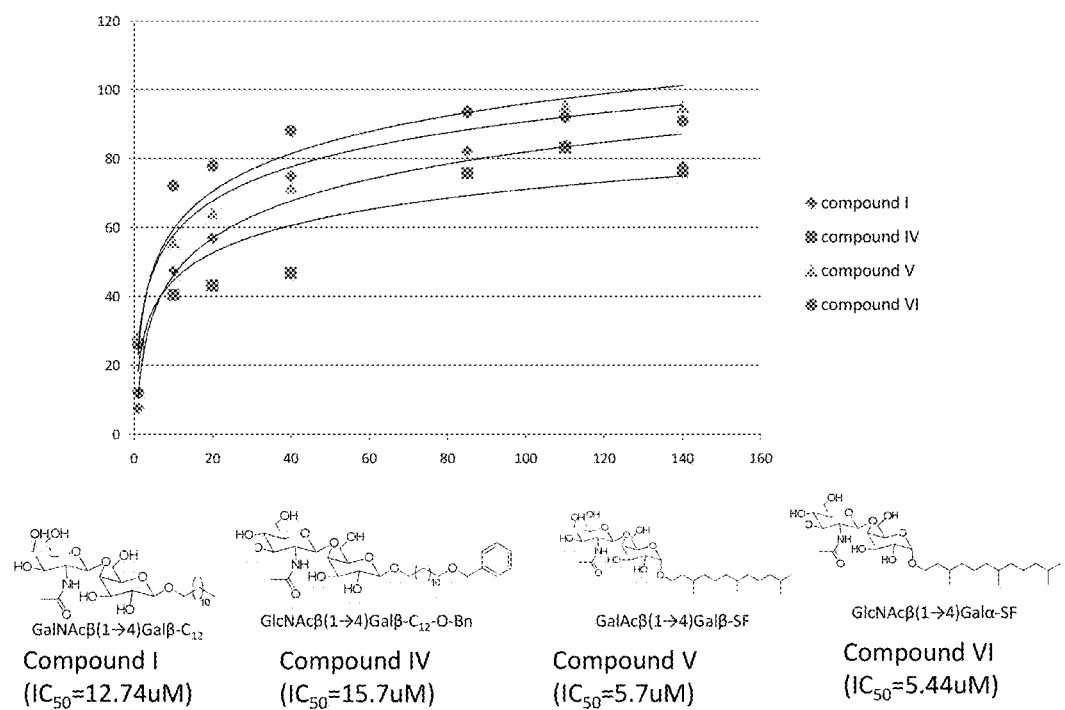

FIG. 26 is series images of swarm (~0.5% agar) plates containing increasing concentrations of DSH inoculated with rhlA mutant (left) and PAO1 (right). The concentrations in μM are indicated above the images, and the identity of the DSHs is shown to the left. Molecules that exhibited dominance over rhamnolipids at inhibiting or activating swarming motilities are highlighted;

FIG. 27 is a plot of the swarm area (after 24 h) of swarming patterns of rhlA mutant versus concentration of rhamnolipids, DβC (4), TβC (5), SFβM (14), DβG (8) and SFβC (12) on soft agar gel (~0.5% agar). Insert, expanded plot region; y-axis (0-16 cm$^2$) and x-axis (0-25 μM);

FIG. 28 is a series of images of nonswarming *P. aeruginosa* mutant, rhlA after 24 h of inoculation on soft agar (~0.5% agar) plates containing 40 μM of DβC (4), and various concentration of SFβC (12);

FIG. 29 is a graph of (A) Percent surface attached PAO1 biofilm remaining in the wells of microtiter plate after biofilm was allowed to develop for 24 hours with or without 160 μM DSHs (filled bars). Percent PAO1/EGFP adhered on polystyrene surface (unfilled bars). (B) Percent surface attached PAO1 biofilm remaining within the wells of microtiter plate after 24 h old biofilm was treated with 160 μM DSHs for another 24 hours (dispersion of 1-day old biofilm). Bacterial culture media: Luria-Bertani (LB);

FIG. 30 is a graph of dose-response curves along with images of microtiter plates after CV-dye based inhibition assay;

FIG. 31 is a graph of dose-response curves along with images of microtiter plates after CV-dye based dispersion assay;

FIG. 32 is a graph of crystal violet (CV) stained PAO1 biofilm within the wells of the microtiter plate after biofilm was allowed to develop for 24 hours in LB-media without any agents and in LB-media that is supplemented with SFαC (13) ~85 μM; SFαC (13) ~85 μM+Pili peptide ~85 μM; SFαC (13) ~85 μM+Scrambled pili peptide ~85 μM; Pili peptide ~85 μM; Scrambled pili peptide ~85 μM;

FIG. 33 is a schematic of the synthesis of disugar based polyol-derivatized hydrocarbons (PDHs); i) AcBr/AcOH, rt or 60° C., ~1 h; ii) ROH, FeCl$_3$ or Hg(CN)$_2$, MeCN, rt, ~1 h; iii) ROH, FeCl$_3$, MeNO$_2$, rt, ~1 h; iv) MeONa/MeOH, ~12 h, H$^+$ amberlite resin, Neutralize, (pH ~6.5);

FIG. 34 is a schematic of a general structure of certain compounds according to the present invention;

FIGS. 35A and 35B are schematics of the specific structure of certain compounds according to the present invention;

FIG. 36 is a series of images of tests performed on certain compounds according to the present invention;

FIG. 37 is a series of images of tests performed on certain compounds according to the present invention;

FIG. 38 is a series of images of tests performed on certain compounds according to the present invention;

FIG. 39 is a series of images of tests performed on certain compounds according to the present invention;

FIG. 40 is a series of images of tests performed on certain compounds according to the present invention;

FIG. 41 is a series of images of tests performed on certain compounds according to the present invention;

FIG. 42 is a series of images of tests performed on certain compounds according to the present invention;

FIG. 43 is a series of images of tests performed on certain compounds according to the present invention;

FIG. 44 is a chart of the results of tests performed on certain compounds according to the present invention; and FIG. 45 is a graph of the results of tests performed on certain compounds according to the present invention.

DETAILED DESCRIPTION OF THE INVENTION

Referring to the Figures, the present invention comprises a class of disugar hydrocarbons that exhibits control over multiple microbial behaviors. As seen in the following examples, the compounds promote the swarming motility of *Pseudomonas aeruginosa* at low concentration, but inhibit the swarming motility at high concentrations. This capability of dual-functions dominates the effect from the naturally existing rhamnolipids, and is vastly useful for controlling infectious diseases. The present class of molecules according to the present invention also exhibits control over biofilm formation by bacteria and inhibit the formation of a biofilm in a wide range of microbes (*E. coli, Pseudomonas aeruginosa*, and *Candida albicans*) with a higher potency than that of rhamnolipids.

EXAMPLE 1

Swarming motility of *P. aeruginosa* is controlled by multiple genes by screening studies, and, in a laboratory setting, requires soft gels and presumably low surface tensions. For *P. aeruginosa*, mutant rhlA that does not produce rhamnolipid results in nonswarming bacteria. Externally added rhamnolipid reactivates the swarming motility of rhlA mutant. Rhamnolipid is a biosurfactant consisting of a disugar hydrophilic head group and two aliphatic chains.

Figure 1:
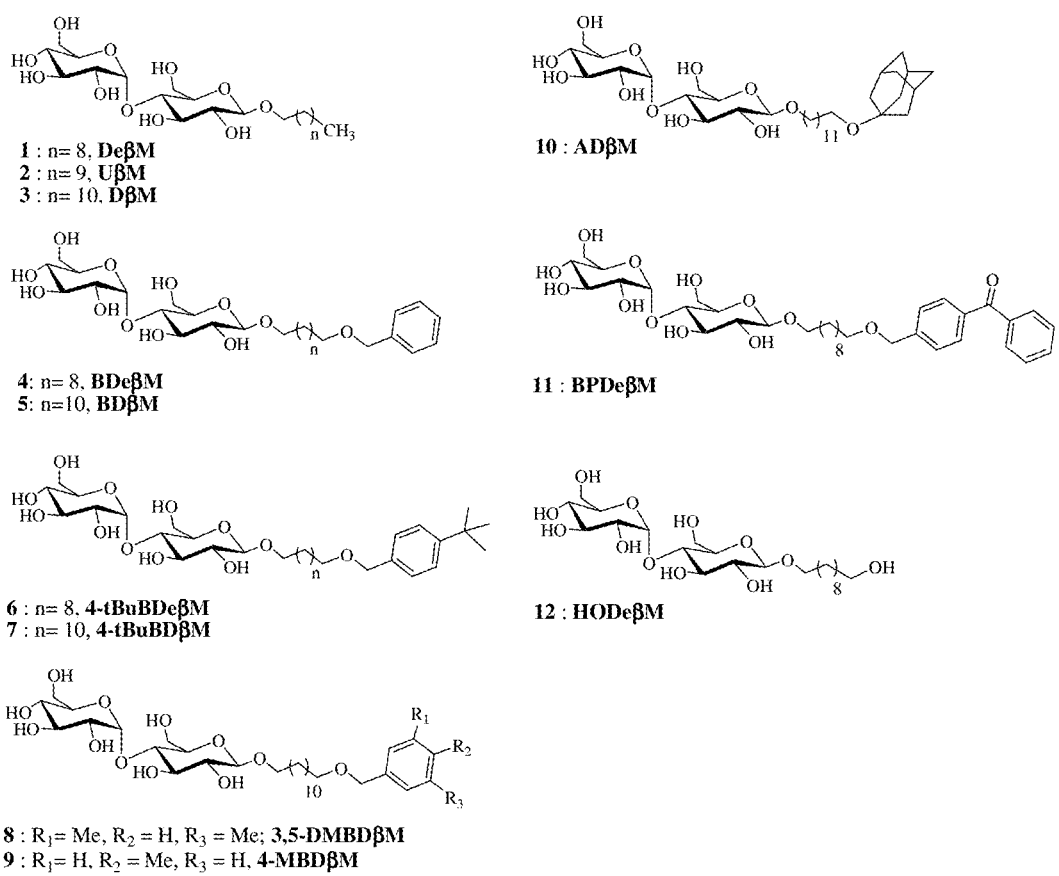
FIG. 1 is a series of chemical diagrams of maltose derived hydrocarbons.

To evaluate the importance of the disugar head group and the surface activities separately, the effect on different types of generic surfactants was screened including: anionic surfactant sodium dodecyl sulfate (SDS), cationic surfactant dodecyl trimethyl ammonium chloride (DTAC) and nonionic surfactant tetra (ethylene glycol) monododecyl ether (C12EG4OH), and a series of disaccharide hydrocarbons (maltose derivatives), as seen in FIG. 1, on the swarming motility of rhlA mutant. The disaccharide hydrocarbons include a maltose stereochemistry (Glcα(1→4)Glcβ) bearing different hydrocarbon tails.

To investigate the effect of aliphatic chain length, maltose derivatives having 10 (decyl β-matoside; DeβM) and 11 (undecyl β-maltoside; UβM) carbons in the aliphatic chains were studied. To investigate the effect of terminal hydrocarbon bulkiness, the following were synthesized: benzyl decyl β-maltoside (BDeβM) and benzyl dodecyl β-maltoside (BDβM), 4-tertiary butyl benzyl decyl β-maltoside (4-tBuBDeβM) and 4-tertiary butyl benzyl dodecyl β-maltoside (4-tBuBDβM), 3,5-dimethyl benzyl dodecyl β-maltoside (3,5-DMBDβM) and 4-methyl benzyl dodecyl β-maltoside (4-MBDβM), and benzophenonyl decyl β-maltoside (BPDOM). To study if nonaromatic bulky substituents can also be effective, adamantane dodecyl β-maltoside (ADβM) was synthesized. To study to what degree a polar head group is needed or tolerated, 12-hydroxy decyl β-maltose (12-HODeβM) was synthesized.

Figure 2:
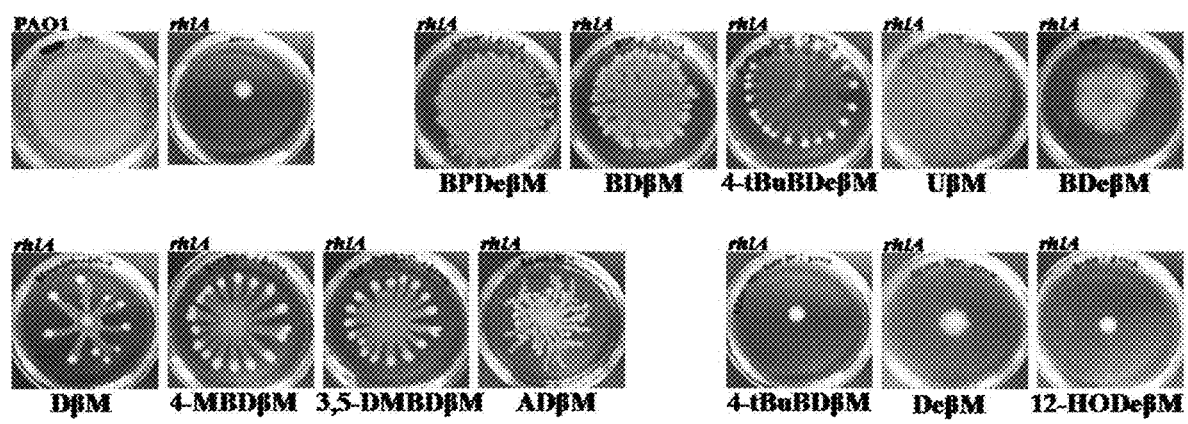
FIG. 2 is a series of images of nonswarming *P. aeruginosa* mutant rhlA that was inoculated on M8 swarm agar (0.5% agar) plates and homogeneously mixed with maltose derivatives to a resultant concentration of 85 µM with pictures were taken 24 h after the inoculation of bacteria on the plates.

Reactivation of swarming motility of the nonswarming mutant by specific maltose derivatives All three generic surfactants, SDS, DTAC, C12EG4OH, did not promote or reactivate the swarming motility of rhlA mutant (see the Supporting Information). Nine of the twelve maltose derivatives reactivated the swarming motility of rhlA mutant to a great extent, and with different degrees and shapes of tendril formation, as seen in FIG. 2. The swarming motility of *P. aeruginosa* is unique that it can form a pattern of tendrils that are not seen in the swarming behavior of other bacteria. In a laboratory setup, when the bacteria are inoculated at the center of the soft agar plate (0.5% agar), tendrils gives a floral pattern and occasionally further resembles a fractal pattern. For the effect of the twelve maltose derivatives on the swarming motility of nonswarming rhl mutants, the molecules were categorized into three groups, swarming-activating with and without well-defined tendril, and swarming nonactivating, as seen in FIG. 2.

On the soft agar plate (0.5% agar) with 85 μM of maltose derivatives, BPDeβM, BDβM, 4-tBuBDeβM, UβM, BDeβM caused rhlA mutant to exhibit swarming motility with without well-defined tendrils but having small protrusions at the periphery of the swarming circle. Among this group, all but BDeβM exhibited a swarming ring size that was comparable to that of the swarming ring by wild-type PAO1. The maltose derivatives DβM, 4-MBDβM, 3,5-DMBDβM, ADβM caused long, straight and well-defined tendrils and with an overall swarming circle that is similar in size as that by the wild-type PAO1. Among this group of maltose derivative, ADβM caused narrow tendrils with frequent turns give a pattern similar to the formation of fractals. The last group of maltose derivatives, 4-tBuBDβM, DeβM, HODeβM, did not exhibit any significant activation of swarming of rhlA mutant The mechanism of tendril formation is a challenging topic, and has been studied by several groups. One proposal involves a mechanism by which the dirhamnolipid is an attractant, whereas mono-rhamnolipid and 3-(3-hydroxyalkanoyloxy) alkanoic acids (HAA) may function as wetting agents and repellants, respectively, during swarming of *P. aeruginosa*. The results and finding here are consistent with the existence of a protein receptor for rhamnolipid. Furthermore, as externally added rhamnolipid in the soft gel also reactivates the swarming motilities of the rhlA mutant, the nine maltose derivatives that also reactivated the swarming motility of rhlA mutant may be ligands that share a common protein receptor with rhamnolipid.

Rhamnolipid is necessary for *P. aeruginosa* to form channeled biofilm at early stages, and interestingly, also for dispersion of mature biofilm when over produced. These findings prompted an examination of the effect of the disaccharide derivatives on biofilm formation and dispersion, as well as an examination to see if there is a possible correlation between activation of swarming motility and biofilm control (dispersion and inhibition). Prior studies showed that pilus is likely responsible for adhesion of *P. aeruginosa* on biotic as well as abiotic surfaces such as polystyrene. Using solid phase binding assays, it has been showed that disaccharide, GalNAcβ(1→4)Galβ, hydrocarbons bind to pili protein of *P. aeruginosa*. These results suggest that GalNAcβ(1→4)Galβ hydrocarbons are potent inhibitors for the adhesion of *P. aeruginosa*. Although the maltose derivatives have a different stereochemistry and structure than GalNAcβ(1→4)Galβ, the anti-adhesion activity of the maltose derivatives on polystyrene was examined because the early stage of biofilm formation involves bacterial adhesion.

A crystal violet (CV) assay was used to measure the amount of PAO1 biofilm formed after 24 h of bacterial inoculation. The fluorescence of green fluorescent proteins (GFP) expressed by PAO1-GFP was measured to directly quantify bacterial adhesion on polystyrene black 96 well plates with and without maltose derivatives after 2 h of bacterial inoculation. To evaluate the potential of maltose derivatives as both anti-biofilm and anti-adhesion agents, they were compared to a brominated furanone (BF8) known to inhibit biofilm formation, and two generic surfactants, sodium dodecyl sulfate (SDS) and tetra (ethylene glycol) monododecyl ether (C12EG4OH). At 110 μM, 5 out of 12 maltose derivatives inhibited more than 80% of PAO1 biofilm. These maltose derivatives include BPDeβM, BDβM, 4-tBuBDeβM, DβM, and 4-MBDβM. Six maltose derivatives, ADβM, 3,5-DMBDβM, 4-tBuBDβM, BDeβM, UβM, DeβM, inhibited between 40 to 60% of PAO1 biofilm, while, 12-HODeβM showed insignificant amount of inhibition, about 30% (as seen in FIG. 3). These results indicate that the anti-biofilm activity is highly sensitive to the structural details of the maltose derivatives, including both the aliphatic chain length and the substituent structure. Increasing the aliphatic chain length from 10 (DeβM) or 11 (UβM) units to 12 units (DβM) increased the inhibition from about 50% to 70%. Incorporating a benzophenone group to a maltose derivative with ten-carbon aliphatic chain increased the inhibition from 50% (BDeβM) to 90% (BPDeβM). In general, increasing the bulkiness of the substituents (BPDeβM, BDβM, 4-tBuBDeβM) increased the inhibition of PAO1 biofilm. These anti-biofilm activities of selective maltose derivatives were also verified by fluorescence static biofilm assay. P. aeruginosa strain PAO1-EGFP that constitutively producing green fluorescent protein was allowed to form biofilm on sterile steel coupons. Maltose derivatives treated biofilms showed weaker fluorescent signal than the control of untreated steel coupons. These results indicate less bacteria and biofilm formation (see the Supporting Information), and is consistent with the results obtained by crystal violet assays.

The inhibition of adhesion (anti-adhesion) of P. aeruginosa by maltose derivatives were studied on polystyrene microtiter plates. The anti-adhesion activities showed an overall similar trend as the anti-biofilm activities with respect to the structures of the maltose derivatives. However, an exact correspondence was not obtained as seen in FIG. 3. Maltose derivatives, BPDeβM, BDβM and 4-tBuBDeβM exhibited high activities for both inhibition of adhesion and biofilm formation, but BPDOM is the most active anti-biofilm agent whereas 4-tBuBDeβM is the most active anti-adhesion agent. Comparing to the amount of adhesion of PAO1-EGFP, 4-tBuBDeβM and BDβM inhibited more than 80% of PAO1 adhesion at 85 μM. Four maltose derivatives inhibited between 30 to 70% of PAO1-EGFP adhesion, which included BPDeβM, DβM, 4-tBuBDβM, BDeβM. Hydroxyl decyl β-maltose (12-HODeβM) showed insignificant inhibition of PAO1-EGFP adhesion, about 7% (see FIG. 3).

Examining the dose dependence of maltose derivatives on biofilm inhibition revealed that 11: BPDOM exhibited an $IC_{50}$ of 22.5 μM; and 5: BDβM, 27.5 μM, as seen in FIG. 4. The anti-biofilm activities obtained from crystal-violet (CV) dye based assays were comparable for both M9+ and LB media, but not so for media without sodium chloride (see the Supporting Information). It is important to note that BF8 showed no inhibition on PAO1 adhesion, while exhibiting about 35% inhibition of biofilm formation. Generic surfactants SDS and C12EG4OH did not show any noticeable biofilm inhibition, but exhibited about 40% inhibition of PAO1 adhesion, as seen in FIG. 3. We note that some of the potent maltose derivatives for P. aeruginosa were further tested for inhibition of E. coli biofilm. Mannose derivatives BPDeβM, BDβM, 4-tBuBDeβM and 4-tBuBDβM at 85 μM inhibited 70 to 75% of E. coli biofilm.

Chemical dispersion of already formed biofilm is often more relevant to medical application, and more challenging than biofilm inhibition assays, for which the agents are introduced at the onset of an experiment. We screened the ability of maltose derivatives at 110 μM to disperse 24 h old biofilm. A similar trend between the anti-biofilm and dispersion activities was obtained for all twelve maltose derivatives with BPDeβM and BDβM being the most potent agents (FIG. 5). Examining the biofilm dispersion dose dependence of BPDeβM and BDβM revealed the half-maximal dispersion ($DC_{50}$) values were 31 μM and 32 μM, respectively (FIG. 6). The $IC_{50}$ and these $DC_{50}$ values of maltose derivatives are comparable to quorum sensing-based small molecule biofilm inhibitors and dispersers, but the mechanism of the anti-biofilm activities of these maltose derivatives are likely not by directly disrupting the quorum sensing of bacteria.

The maltose derivatives do not inhibit bacterial growth at concentration (170 μM) higher than those studied for biofilm inhibition and dispersion. The active maltose derivatives are also more potent than a brominated furanone (BF8) previously studied by us at inhibiting biofilm formation. Furthermore, BF8 does not inhibit the adhesion of bacteria. Together, the dual action of anti-adhesion and anti-biofilm activities of these non-microbicidal disaccharide hydrocarbons may offer potentials for further therapeutic agent development.

The structural sensitivity of these maltose derivatives at reactivating the swarming motility of rhlA mutant supported the existence of one or more protein receptors for these disaccharide hydrocarbons. In addition to this structural selectivity for activating the swarming motilities, two observations also suggest that the anti-biofilm activity is not due to a simple washing effect because of the surface activity of the molecules. First, the effective concentration such as $IC_{50}$ and $DC_{50}$ of biofilm inhibition and dispersion is significantly lower than the critical micelle concentration of a typical maltoside (cmc of DβM is 170 μM). Second, all other generic surfactants examined in this study, including SDS, C12EG4OH and DTAC, did not show any anti-biofilm activities (either inhibition or dispersion). Inhibiting the bacterial adhesion alone is not likely the sole attribute to the anti-biofilm activities because the already adhered bacteria and formed biofilm can be effectively dispersed by the same maltose derivatives. On the same note, the reactivation of the swarming motility of rhlA mutant by disaccharide hydrocarbons is also likely driven by ligand-receptor interactions rather than merely lowering the surface tension of the soft gel. None of the generic surfactants reactivated the swarming motility rhlA mutant while C12EG4OH actually has a higher surface activity then known disaccharide-derivatives.

The ability of the maltoside derivatives to antagonize the two quorum sensing circuits las and/or rhl of P. aeruginosa was investigated by using two reporter strains (PAO1/plasI-LVAgfp, PAO1/prhlI-LVAgfp). These reporter strains produce natural AHL signals, and binding of such signal molecules to the Lux-type receptor proteins (LasI and LasR) activates the expression of green fluorescent protein (GFP) encoded by the plasmid. Our results (see the Supporting Information) indicated that maltose derivatives did not compete with the natural signal to cause a decrease in fluorescent signal. Further, the ability of the maltose derivatives to agonize the quorum sensing circuit in P. aeruginosa in the absence of natural AHLs was studied with a double knockout strain (PAO-JP2 (plasI-LVAgfp) and PAO-JP2 (prhlI-LVAgfP) that do not produce AHLs. The maltose derivatives did not show any significant increase in the fluorescent signals (see the Supporting Information), indicating that they did not agonize the quorum sensing receptors.

Many receptors exist for saccharide derivatives on bacterial surfaces. Among these protein receptors, three systems may be related to the anti-biofilm activities by the maltose derivatives. First, the vast biological activities of rhamnolipids (building of porous biofilm, dispersion of mature biofilm and enabling of swarming motility) suggest that one (or more) receptor exists, and the identity of which has not been discovered but maybe strongly associated with the protein SadB (surface attachment-defective gene product). Second, when P. aeruginosa swarm on the soft agar gel, it appears to differentiate into at least two phenotypes, the hyperactive swarming bacteria at the tip of the swarming tendril and the less mobile bacteria at the center of the swarming ring and on the stem of tendrils. Among genes screened by Deziel and coworkers, gltK is highly up-regulated in the bacteria at the tendril tip but not for bacteria at the swarming center. 19 Gene gltK of *P. aeruginosa* encodes an inner membrane component of the ATP-binding cassette (ABC) transporter system for transporting glucose. Interestingly, the gltK gene product in *P. aeruginosa* is a member of the family of MalK proteins, which transport maltose in *E. coli*. Third, 90% of the adhesion of *P. aeruginosa* is likely caused by the pili proteins, and that pili protein is responsible for the recognization of *P. aeruginosa* to the GalNAcβ(1→4)Galβ moieties found on human host cells. These pili proteins are also implicated to be responsible for adhesion on polystyrene. Together with the results that the disaccharide hydrocarbons inhibited the adhesion of *P. aeruginosa* on polystyrene, the maltose derivatives may target pili proteins that recognize GalNAcβ(1→4)Galβ on mammalian cells. In addition, the maltose derivatives activate the swarming motility of the nonswarming mutant a biological function also exhibited by rhamnolipid. Thus, these disaccharide derivatives may also target the receptor(s) of rhamnolipids. Whether the ligands GalNAcβ(1→4)Galβ on mammalian cells and rhamnolipids share a common receptor on bacteria is not certain, but maltose derivatives could be promiscuous in binding multiple receptors, or that rhamnolipid is the ligand for pili protein as well. Both swarming reactivation and anti-biofilm activities are highly sensitive to the structural details of the maltose derivatives, but there is no strict correlation between the two biofunctions. For example, for the three maltose derivatives that do not reactivate swarming of rhlA mutant, two of them of are sluggish biofilm inhibitors (HODeβM and DeβM gave 32% and 41% biofilm inhibition at 110 μM), but one of them is a strong biofilm inhibitor (4-tBuBDβM gave 74% biofilm inhibition at 110 μM). However, the level of receptor expression is likely different during biofilm formation and bacterial swarming, and thus a rigorous determination of correlation is still ongoing.

Furthermore, the swarm-nonactiviting 4-tBuBDβM differs from swarming-activating 4-tBuBDeβM and BDβM by only two methylene units in the aliphatic chains and a tert-butyl group, respectively. Because of this structural sensitivity, these results may also suggest an allosteric effect on the receptor upon binding, which leads to different agonistic or antagonistic effect on the further cell signaling events. The effect of disaccharide stereochemistry and further exploration of different bulky hydrocarbon structures on biofilm and swarming motility is an ongoing subject of our study.

The strong biological functions (reactivation of swarming motility, anti-adhesion and anti-biofilm activities) of this class of maltose derivatives, and the sensitive dependence of these bioactivities to the molecular structures suggest that one or more protein receptors may exist, for which small molecule binding causes a strong inhibition and dispersion effect on the biofilm and other bacterial behavior. As biofilm formation and swarming motilities are quite common for microbes, similar receptors for disaccharide derivatives likely exist in different types of bacteria. Thus, we believe that targeting these receptors form the basis of an effective approach to control the biofilm formation and related diseases.

EXAMPLE 2

The present invention also encompasses a chemical library of disaccharide hydrocarbons (DSHs) that were developed by systematically changing the glycone as well as aglycone part of the DSH (FIG. 7) and then investigated to determine the effect that these structural changes have on swarming motilities of PA and its non-swarming mutant strain. The library was further tested for anti-biofilm activities. The efficacy of DSHs to inhibit biofilm formation in PAO1 was reduced when these agents were pretreated with a solution of synthetic pili peptide (PAO$_{128-144}$)ox.

In order to understand the relationship between structural detail and activities, a library of DSHs was synthesized as seen in FIG. 7. The basic synthetic variations employed involved first changing the glycone and then the aglycone part of DSHs. Glycone variations included synthesizing 12 carbon chain DSHs with cellobiose; Glcβ(1→4)Glcβ (Dodecyl-β-cellobioside; 4: DβC), lactose; Galβ(1→4)Glcβ (Dodecyl-β-lactoside; 7: DβL), rhamnose; rha (Dodecyl-α-rhamnoside; 9: DαR) and β-cyclodextrin; βCD (Dodecyl-βCD-squarate; 18: DβCDS) stereochemistries. Two commercially available DSH with 12 carbon chain bearing maltose Glcα(1→4)Glcβ (Dodecyl-β-maltoside; 1: DβM) and glucose; Glc (Dodecyl-β-glucoside; 8: DβG) stereochemistries were also used for structural comparison. Next, systematic variations to aglycone hydrocarbon chain were done. Keeping sugar stereochemistry as cellobiose, DSHs were synthesized having 10 (Decyl-β-cellobioside; 2: DeβC), 11 (Undecyl-β-cellobioside; 3: UβC), 13 (Tridecyl-β-cellobioside; 5: TβC) hydrocarbon chain. Effect of terminal unsaturation was investigated by synthesizing 11 carbon cellobiose based DSH having terminal unsaturation (Undecylene-β-cellobioside; 10: UDβC). Effect of α/β anomers on activity was investigated by synthesizing DSH having cellobiose stereochemistry but with 12 carbon chain at α-position (Dodecyl-α-cellobioside; 6: DαC). Effect of hydrocarbon bulkiness on DSHs activity was next studied by synthesizing agents with saturated farnesyl tail (possessing short methyl branches) with three different disaccharide stereochemistries; cellobiose (Saturated farnesyl-β-cellobioside; 12: SFβC and its α-anomer (Saturated farnesyl-α-cellobioside; 13: SFαC), maltose (Saturated farnesyl-β-maltoside; 14: SFβM and lactose (Saturated farnesyl-β-cellobioside; 15: SFβL). Effect of chain unsaturation on agent activity was investigated by synthesizing cellobiose-derived farnesyl (Farnesyl-β-cellobioside; 11: FβC). The effect of chain bulkiness on activity was further investigated by synthesizing two DSHs with double-branched tail (overall lipid-like structure) (2-octyl-dodecyl-β-cellobioside; 16: 2-ODβC and its α-anomer (2-octyl-dodecyl-α-cellobioside; 17: 2-ODαC).

Synthesis of mono-sugar and disugar based hydrocarbons with systematic variation in hydrocarbon chain length and structure were synthesized by slightly modifying a reported procedure as seen in FIG. 8. Briefly, unprotected sugar was simultaneously acylated and brominated (at anomeric carbon) using a binary mixture of AcBr/AcOH to obtain aceto-bromo sugar. The aceto-bromo sugars were then glycosidated at anomeric position using either FeCl$_3$ or Hg(CN)$_2$ as catalysts. For obtaining β-anomer as the major glycosidation product, MeCN was used as the solvent, while MeNO$_2$ primarily gave α-anomer. The resolution of α/β anomers was done using column chromatography (β-anomer usually eluted first). The glycosidated products were deprotected under basic conditions using methanolic sodium methoxide solution followed by neutralization to a pH 6.5 (using H+ amberlite resins) (Zemplen deacetylation).

Synthesis of di-(difluro-phenoxy) squarate (18 A) and β-cyclodextrin amine (18c: βCD-NH$_2$) were done according to a known procedure. Dodecyl-βCD-squarate (18: DβCDS)

was synthesized according to FIG. 8. Briefly, nucleophilic substitution by dodecyl amine of one phenoxy substituent on squarate was done in THF at −78° C. for 12 hours followed by substitution of second phenoxy substituent by βCD-NH$_2$ in water/DMF/acetone ternary solvent mixture over a period of 4 days to yield 18: DβCDS.

All synthesized polyol-derivatized hydrocarbons were soluble in water at 160 μM (concentration at which these agents were tested for anti-biofilm activity) (except 17: 2-ODαC), whose stock solutions were prepared in a solvent mixture of water/EtOH). In general DSH with galactose stereochemistry had poor water solubility; (15: SFβL) was not soluble in either water or in water/EtOH mixture). All synthesized disaccharide hydrocarbons (DSHs) were non-toxic to the growth of Pseudomonas aeruginosa at 160 μM.

Control of swarming motility of wild type and nonswarming mutants of P. aeruginosa Multicellularity in bacteria manifests through other highly organized surface associated behaviors such as swarming motility. Swarming phenomenon has been observed in both Gram-negative as well as Gram-positive bacteria. Under laboratory setting, swarming motility is usually studied on a solid medium containing 0.5-0.7% agar (soft agar). When a small amount of bacterial culture is spotted on the soft agar surface, it is essential that a certain minimum cell density is achieved in order for swarming to happen. Bacterial quorum sensing hence is not just critical for biofilm formation but is also closely related to swarming process. It is argued that, that triggering a switch to swarming mode would require a coordinated merger of many chemical and physical cues in the bacteria. In combination, such physio-chemical changes are capable of inducing morphological changes that are necessary for swarming. Therefore, pathways associated for swarming induction often share same cross-roads with biofilm formation circuitry. Both biofilm formation and swarming are multicellular bacterial behaviors that contribute to the survival of the microbes in environment and in-vivo, therefore are important life-styles necessary for maintaining virulence. Therefore, agents that affect biofilm formation in a particular bacterial species could potentially affect the swarming process in that bacterium too.

The swarming bacterial cells are generally associated with having multiple flagella on their surface. While in bacteria like Pseudomonas aeruginosa, in addition to two-polar flagellum the presence of Type IV pili as well as the production of a biosurfactant, rhamnolipid is critical for promotion of swarming. The role of rhamnolpid in Pseudomonas aeruginosa is not limited to promotion of swarming (probably by reducing surface tension) but they are also implicated in forming water channels with in biofilms and maintaining mushroom shaped structures. In addition, rhamnolipid can disperse mature biofilm by mediating detachment and over production of rhamnolipids results in impaired biofilm formation. Because of the important roles that rhamnolipids play in assisting Pseudomonas aeruginosa multi-cellular behaviors, the exploration of its putative receptor on the bacterial surface is under constant study.

Biosynthesis of rhamnolipids involves genes that are under the control of quorum sensing regulators RhlR and LasR. Synthesis of 3-(3-hydroxyalkanoyloxy) alkanoic acids (HAA) precursors is brought about by rhlA gene, following which rhlB encodes for the enzyme (rhamnosyltransferase) that catalyzes the addition of rhamnosyl moiety to HAA. Eventually, RhlC catalyzes the addition of a second rhamnose moiety to generate di-rhamnolipid. Together, HAA, mono-rhamnolipids and di-rhamnolipids are known to facilitate the swarming of Pseudomonas aeruginosa on soft-agar to form solar-flair like and/or denritic/tendril swarm patterns. While the exact mechanism of how Pseudomonas aeruginosa form tendrils is still under investigation, some aspect of di-rhamnolipids and its precursors have been brought to light. Namely, di-rhamnolipids are known to attract swarm cells, whereas HAA are known to be swarm cell repellants. Mono-rhamnolipids is known to merely serve as a surface wetting agent.

Like rhamnolipids and its precursors, HAA and mono-rhamnolipids (together called as rhamnolipids hence forth), DSH are also amphiphilic molecules and we were interested to know whether these efficient anti-biofilm agents could also undertake functions naturally carried by rhamnolipids. Pseudomonas aeruginosa strain PAO1 normally swarms on a soft agar surface to give a dendritic swarm pattern. Soft-agar (~0.5%) plates supplemented with 7 different DSH (12: SFβC; 14: SFβM; 13: SFαC; 7: DβL; 2: DeβC; 1: DβM; 4: DβC) at 110 μM were inoculated with PAO1 (OD600~0.5). Images of the swarm agar plates 24 hours after inoculation are shown in FIG. 9. When compared to swarm agar plate with no agent, 7: DβL; 2: DβC and 1: DβM did not significantly affect the swarm pattern, although 4: DβC induced more tendril formation. Importantly, DSHs that were powerful anti-biofilm and anti-adhesive agents (12: SFβC; 14: SFβM and 13: SFαC) completely inhibited the swarming of wt PAO1. These results indicate that that 12: SFβC; 14: SFβM and 13: SFαC could be displacing rhamnolipids from its natural receptor.

N-(3-oxohexanoyl)-3-aminodihydro-2(3H)-furanone (AHL) has been identified as a bacterial signaling molecule where naturally isolated as well as synthetic AHLs stimulated light production in Photobacterium fischeri and the amount of light produced increased over the range 0.003-3 μg/mL and then decreased at higher concentrations (especially for synthetic AHL). On comparing the effect of 12: SFβC on swarming of PAO1, it is evident that higher concentration of 12: SFβC (>20 μM) exhibit inhibition of PAO1 swarming. However lower concentration of SFβC (<10 μM) exhibit slight promotion of PAO1 swarming as seen Figure. This activity reversal as the concentration increases is consistent with disaccharide hydrocarbons SFβC being a cell signaling molecule.

Some polyol-derivatized hydrocarbons reactivate swarming in nonswarming PA mutant (rhlA) Transposon mutation involving gene rhlA generates a PAO1 mutant which lacks in the biosynthesis of di-rhamnolipids, mono-rhamnolipids and HAA hence as a consequence, this mutant (rhlA) is non-swarming. The swarming reactivation of non-swarming mutant rhlA by DSHs was tested (12: SFβC; 14: SFβM; 13: SFαC; 7: DβL; 2: DβC; 1: DβM; 4: DβC). Agents were solubilized homogenously into the melted agar (~0.5%) to a resultant concentration of 110 μM and then the agar was cooled to form a semi-solid. Non-swarming mutant rhlA (OD600~0.5) was then inoculated. After 24 hours, as seen in FIG. 11, 1: DβM; and 4: DβC fully restored the swarming of rhlA with 4: DβC forming fine tendrils. However, 12: SFβC, 14: SFβM, 13: SFαC 7: DPI, and 2: DeβC were incapable of reactivating the swarming in non-swarming mutant rhlA. While, the swarming results of rhlA indicates that some DSHs like 1: DβM; and 4: DβC are fully capable of mimicking the function of rhamnolipids, the theory of swarm attractants and repellants alone cannot explain the mechanism of tendril formation here (as there is no production of any HAA).

As 4: DβC was capable of reactivating the swarming in non-swarming mutant rhlA, we did a concentration and time dependant study to observe the progression of swarming. Concentration as low as 20 µM were sufficient to reactivate non-swarming mutant rhlA to swarm (FIGS. 12 and 13). Interestingly, on increasing the concentration from 40 W to 85 W, there was a decrease in the swarming reactivation ability of 4: DβC.

The signaling molecule like behavior of 12: SFβC was also noticed in its ability to reactivate swarming of rhlA only between the concentration range of 5-12 W (FIGS. 14 and 15). With rhlA mutant also, there was no reactivation at higher concentrations of 12: SFβC.

SFβC is at least twice as strong a ligand than 4: DβC for the swarming receptor At 110 µM 12: SFbC inhabits the swarming of wt PAO1 (as seen in FIG. 9) whereas 4: DbC promotes tendril formation at the same concentration. Also, at same concentration, 12: SFbC does not reactivate the swarming of rhlA mutant (as seen in FIG. 11) whereas 4: DbC fully restores swarming with fine tendrils. Mechanistic understanding to consider here is whether 12: SFbC binds swarming receptor better than other DSHs by co-administration of two DSHs, SFbC (inhibits PAO1 swarming) and DbC (promotes PAO1 swarming). If SFbC binds stronger than DbC to swarming receptor, then there will be inhibition of DbC reactivated swarming. If not, 4: DbC reactivated swarming will still be active. Co-administration SFβC (as low as 20 µM) suppresses the reactivation of rhlA swarming by DβC (40 µM) (FIG. 16), suggesting that 12: SFbC is at least twice a stronger binding ligand than 4: DbC.

The ability of DSHs was tested to inhibit *Pseudomonas aeruginosa* adhesion, biofilm and to disperse pre-formed biofilm. To quantify the amount of PAO1/EGFP attached on the surface of micro titer plates with or without the synthesized DSHs, fluorescence emitted by green fluorescent proteins (GFP) was quantified (see supporting info for details). Crystal violet (CV) based static biofilm assay (see supporting info) was used to screen the anti-biofilm potencies of all synthesized agents. Both surface attached (SA) (FIG. 17) and total (SA+air-liquid interface) biofilm of *P. aeruginosa* was quantified. Although, only the SA biofilm is reported here, the total biofilm quantified (not reported) also had similar potency trend for various DSHs. CV assays were also used to quantify the amount of *P. aeruginosa* biofilm remaining after dispersion experiments (FIG. 19). Initially, all agents were screen for anti-biofilm activities (both inhibition and dispersion) at 160 µM. Agents that showed >50% inhibition or dispersion were used further in a dose-response manner to calculate the $IC_{50}$ (inhibition) or $DC_{50}$ (dispersion). All reported biofilm inhibition results are an average of 4 identical wells. Each experiment has been repeated at least three times, each time giving similar results (repeat results not shown).

A test of detecting the amount of bacteria adhered on polystyrene surfaces within 2 hours of inoculation was developed. Based on the anti-adhesive assay, DSHs having bulky aliphatic tails were strong anti-adhesive agents that prevented *Pseudomonas aeruginosa* from adhering onto poly-styrene surface as seen in FIG. 17. Agents with farnesyl or twelve carbon aliphatic chains and bearing either cellobiose or maltose head group prevented 60-80% of bacterial adhesion.

Stereochemistry of disaccharide is important for the anti-biofilm activity. Monosaccharide (glucose; 8: DβG and mono-rhamnoside; 8: DαR) based hydrocarbons having twelve carbon aliphatic chain had poor anti-biofilm activity. However disaccharide hydrocarbons having a twelve carbon chain and a disaccharide stereochemistry (maltose, Glcα(1á4)Glcβ; 1: DβM) reduced the biofilm content by 50% (as seen FIG. 16). Synthesized cyclic oligosaccharide (18: DβCDS) was not only incapable of exhibiting any biofilm inhibition but also increased the biofilm content. Therefore, while DSHs with 1 sugar head group were poor anti-biofilm agents, DSH with oligosaccharide head group was even worse. However, DSHs with disaccharide head group exhibited decent anti-biofilm activity.

Anti-biofilm potencies of three different DSHs each bearing a twelve carbon aliphatic chain with either lactose (Galβ(1→4)Glc, 7: DβL (poor solubility in water), cellobiose (Glcβ(1→4)Glc, 4: DβC) or maltose (Glcα(1→4)Glc) based disaccharide head group revealed that Glcβ(1→4)Glc stereochemistry out-performed other stereochemistries (as seen in FIG. 16). While lactose stereochemistry severely compromised the anti-biofilm activity, cellobiose stereochemistry exhibited 60% biofilm inhibition. In general, cellobiose hydrocarbons compared better than those of maltose hydrocarbon.

Chain length of the hydrocarbon is important for biofilm inhibition. Aglycone moiety of DSH was then systematically altered keeping cellobiose based sugar head group stereochemistry constant. Firstly, DSHs with aliphatic chain (β-anomer) length having 10 (2: DeβC), 11 (3: DβC), 12 (4: DβC) and 13 (5: TβC) carbons were compared. DSH with 10 carbon chain resulted in complete loss of anti-biofilm activity while 12 carbon chain seemed optimum. This reliance of activity on aliphatic chain length is reminiscent of another biochemical phenomenon exhibited by many gram-negative as well as gram positive bacteria, qurom sensing. Different bacterial species are able to distinguish their own chemical signal from that of others by recognizing the difference in the length of acyl side chain of acyl-homoserine lactone (AHL) auto inducers (chemical signals). The AHL signals are recognized by specific AHL-responsive receptor proteins known as "R" proteins such as LuxR or LasR.

This recognition is primarily based on the ability of "R" proteins to distinguish one AHL from another based on the length of the acyl side chain. The optimization of DSH with C12 aliphatic chain to give maximum anti-biofilm activity is therefore an indication of a ligand-receptor phenomenon.

At 160 µM, both 12: SFβC and 13: SFαC were powerful inhibitors (up to 80%) of *P. aeruginosa* biofilm (FIG. 17). The low $IC_{50}$ values of 12: SFβC (4.9 µM) and 13: SFαC (~32.3 µM) (see FIG. 18) are comparable to some of the powerful synthetic agents that have been reported to non-microbicidally inhibit *P. aeruginosa* biofilm. In an attempt to further optimize anti-biofilm activity, maltose and lactose based saturated farnesyl was synthesized (14: SFβM and 15: SFβL respectively). Although, only slightly less potent at ~160 µM, 14: SFβM had a much lower $IC_{50}$ (~97.2 µM) (FIG. 18). Synthetic lactose analog exhibited poor solubility in water and hence was not tested for anti-biofilm activity. The ability of DSHs, SFβC, SFαC, DβC, DβC and DβL to inhibit PA biofilm formation on steel coupons was tested. At 160 µM of DSHs, CLSM micrographs reflect the similar trend of biofilm inhibition activities obtained from CV-dye based assay.

Polyol-derivatized hydrocarbons with the alkyl chain having lipid-like structure are not potent anti-biofilm agents. With the intent to further increase the bulkiness of the aliphatic chain, we synthesized two mono-branched DSH anomers having lipid-like structure (16: 2-ODβC and 17: 2-ODαC). Unlike DSHs having methyl branched saturated aliphatic chain (saturated farnesyl DSHs), aliphatic chain giving a lipid-like structure were ineffective at biofilm inhibition as seen in FIG. 17.

Unsaturated in the aliphatic chains reduced the anti-biofilm activity of the polyol-derivatized hydrocarbons. DSH having a farnesyl aliphatic chain (11: FβC) was synthesized, only to generate a structure with poor anti-biofilm activity as seen in FIG. 17. Similarly, DSH having an aliphatic chain with terminal unsaturation (10: UDβC) had lesser potency than DSH with completely saturated aliphatic chain (3: UβC) as seen in FIG. 17.

DSH's possession of anti-biofilm activity was determined by virtue of these agents interfering with bacterial cell-to-cell communication which is under las and rhl control. One of the recent approach for a nonmicrobicidal control of biofilm aims to develop agents that disrupt bacterial cell-to-cell communication by acting as mimics to the natural molecules (autoinducer) that bind lasI and rhlI proteins, which are encoded by las and rhl gene. The binding of these mimics with lasR and rhlR proteins either activates or represses the expression of lasI or rhlI.[6] In gene reporter assay, the expression of lasI and rhlI proteins is quantified by measuring expression of green fluorescent protein (GFP) fused to lasI and rhlI genes.[5] Two reporter strains of Pseudomonas aeruginosa (PAO1/plasI_LVAgfp and PAO1/prhlI_LVAgfp) express green fluorescence protein on activation of las or rhl quorum sensing system. The activation or repression of las or rhl quorum sensing system in PA was tested by various DSHs. For both las and rhl quorum sensing systems, addition of DSHs (12: SFβC and 13: SFαC) had no significant change in the fluorescence.

Apart from preventing biofilm formation, the efficacy of an anti-biofilm agent is further enhanced if it can also disperse preformed biofilm. Such agents are versatile because they effectively target different biofilm developmental stages. The ability of DSHs to disperse pre-formed (1 day old) biofilm was tested. The general trend of dispersion ability was consistent with inhibition power as seen in FIG. 19. $DC_{50}$ values (~36.4 µM for 12: SFβC and ~78.4 µM for 13: SFαC) are indicative of powerful dispersion activity as seen in FIG. 20.

*P. aeruginosa* are reported to bind human mucosal cells via tip of the pilus and can having binding to biotic and abiotic surfaces that is mediated by pili. Minimum binding sequence of pili peptide for PAO strain is the 17 AA at C-terminus PAO(128-144)ox [Ac-A-C—K-S-T-Q-D-P-M-F-T-P-K-G-C-D-N—OH] where cysteines 129 and 142 form a disulfide bond, forming a looped peptide. These pili specifically recognize disaacharide GalNAc-Gal. Increasing the hydrophobicity by lengthening the alkyl chain attached at 1-position increased the binding between carbohydrate and pili peptide. The pili peptide PAO(128-144)ox was synthesized by FMOC synthesis. A scrambled pili peptide was also synthesized by changing the cysteines 129 and 142 by alanines, PAO(C129A/C142) S [Ac-A-A-K-S-T-Q-D-P-M-F-T-P-K-G-A-D-N—OH]. When 13: SFαC was pretreated with a solution of PAO(128-144)ox it exhibited no inhibition of PA biofilm. However, pretreatment with PAO (C129A/C142)_S did not compromise the efficacy of the agent as seen in FIG. 21. DSHs are possibly preventing the initial attachment of PA on abiotic surface, and pili-peptide may compete with DSHs for the receptors on PA, and hence reducing the efficacy of DSHs.

EXAMPLE 3

The effects of dodecyl maltoside was tested on the bacterial clearance in a mouse pneumonia model. SP-A and SP-D double knockout (SP-A/D KO) mice with C57BL/6 background were used for this study. Original SP-A/D KO mice were provided by Dr. Samuel Hawgood of The University of California San Francisco, and these mice had been backcrossed at least ten generations against a C57BL/6 background. Mice used in this study were bred in the animal core facility at SUNY Upstate Medical University under pathogen-free conditions. All animal experiments were conducted in accordance with the Institutional Animal Care and Use Committee guidelines of SUNY Upstate Medical University and the National Institutes of Health guidelines on the use of laboratory animals.

*Pseudomonas aeruginosa* strain PAO1-BAA-47 (wild type) from frozen stocks were streaked onto LB agar plates and incubated at 37° C. for 24 hours, and a single colony was picked up and transferred to a flask contains 20 mL of LB Broth and incubated at 37° C. for 13 hours with shaking at 250 rpm. The optical density at 600 nm ($OD_{600}$) was measured and it is usually about 2.1 by this time. The bacterial cells were recovered by centrifugation, resuspended in saline and diluted to an optical density of 0.6 at $OD_{600}$. One mL of this solution was estimated to contain $2 \times 10^9$ CFU. The solution was diluted 20 times with saline for use. Based on our preliminary data, a 50 µl (containing $5 \times 10^6$ CFU) of the diluted bacterial solution was used to inject each mouse intratracheally.

A total of 12 male and 16 female SP-A/D KO mice (8-12 weeks old) were used for all experiments. Three independent experiments were performed using age and gender matched mice. The tracheal delivery of [$50_1 1.1$ ($5 \times 10^6$ CFU)/mouse] was accomplished by anesthetizing mice with $30_1 1.1$ of the mixture of ketamine:xylazine (100 mg/kg:10 mg/kg), making a small incision above the trachea and directly injecting the bacterial suspension inside the trachea. After 24 hours the incision was reopened under anesthesia and 50 µl solution containing 170 µM of Dodecyl Maltoside (DM) was injected into the trachea of the treatment group and 50 µl saline was injected into the trachea of the control group. After 24 more hours all mice were sacrificed.

Randomly selected mice from each group were prepared for quantitative bacteriology. The left half of the lung of each mouse was removed aseptically and homogenized in 1 ml of sterile 0.9% saline and 100 µl of appropriately serial diluted lung homogenates sample were plated on LB agar, incubated at 37° C. for 24 hours, and inspected for *P. aeruginosa* colonies.

After anesthetizing mice with ketamine:xylazine 100 mg/10 mg, a large abdominal incision was made and the intestine was turned to the left side the inferior vena cava and Aorta were cut using iris scissors and leave the animal was left to bleed and then various tissues were harvested from the mice including lung, liver, spleen, kidney and intestine. Tissues were wrapped in a labeled aluminum foil, snap frozen in liquid nitrogen and kept in −80° C.

Randomly selected lungs were slowly inflated with 1 ml of formalin and then completely immersed in formalin. Specimens were embedded in paraffin and 5 µm sections cut. Slides were stained using hematoxylin and eosin for standard light microscopic analysis.

Experimental data were analyzed by SigmaStat 3.5 software (Systat Software, Inc., San Jose, Calif.) and presented as means±standard error. Two-group comparisons were performed using Student's t test. A P value of <0.05 was considered to be statistically significant. The results showed that DM treatment significantly decreased CFU number in the lung compared to the control, as seen in FIG. 22 and improved the lung inflammation, as seen in FIG. 23.

EXAMPLE 4

In another study, a series of disaccharide hydrocarbons (DSHs) with different sugar stereochemistries and aliphatic chain structures were synthesized and tested for the capability of controlling multiple bacterial behaviors, including inhibiting and activating the swarming motility of bacteria, inhibition of bacterial adhesion, and inhibition and dispersion of bacterial biofilm formation. Different structural elements and their degree of importance have been identified for this class of molecules for dominating natural rhamnolipids at controlling the swarming motility of wild type Pseudomonas aeruginosa (PAO1) and a nonswarming mutant rhlA, and inhibiting biofilm formation. In addition, these molecules exhibit an activity reversal on activating the swarming motility of nonswarming mutant rhlA, by which a low concentration range of DSHs reactivates the swarming motility, but a high concentration range inhibits the swarming motility. The effect of causing two different phenotypes of bacteria at the same time was also explored.

Many biological recognition events such as cell-to-cell interactions, bacterial, fungal and viral infections of human host cells are mediated through carbohydrate-protein interactions. While the identity as well as the existence of the receptors for rhamnolipids remains elusive, flagella proteins of P. aeruginosa can bind to the sugar moieties of mucin29 and asialo-GM130, and pilin can bind to bind D-GalNac-β (1→4)D-Gal-β disaccharide moiety. Proteins LecA and LecB of PA, on the other hand, are known to be more specific for galactose and fucose, respectively.

A series of synthetic carbohydrate hydrocarbons with different disaccharide stereochemistry, along with two monosaccharides and one large cyclic hepta-saccharide moiety, were screened (FIG. 24A). The disaccharide hydrocarbons include maltose (Glcα (1→4)Glcβ)-based molecules including, dodecyl-β-maltoside (DβM), 1; saturated farnesyl-β-maltoside (SFβM), 14; and cellobiose (Glcβ(1→4)Glcβ)-based molecules including, dodecyl-β-cellobioside (DβC), 4; decyl-β-cellobioside (DβC), 2; undecyl-β-cellobioside (UβC), 3; tridecyl-β-cellobioside (TβC), 5; dodecyl-α-cellobioside (DαC), 6; undecylenyl-β-cellobioside (UDβC), 10; farnesyl-β-cellobioside (FβC), 11; saturated famesyl-β-cellobioside (SFβC), 12; saturated farnesyl-α-cellobioside (SFαC), 13; 2-octyl-dodecyl-β-cellobioside (2-ODβC), 16; 2-octyl-dodecyl-α-cellobioside (2-ODαC), 17; and lactose (Galβ(1→4)Glcβ) including, dodecyl-β-lactoside (DβL), 7; saturated famesyl-β-lactoside (SFβL), 15. In addition to changing the lengths of the aliphatic chains, bulky hydrocarbons with different degree of unsaturation (11) and methyl branches (12, 13, 14, 15) are included. These bulky hydrocarbons are derived from farnesol and hydrogenated farnesol (3,7,11-trimethyl-dodecane). The monosaccharide hydrocarbons include dodecyl-β-glucoside (DβG), 8 and dodecyl-α-rhamnoside (DαR), 9. To examine the effect of a large oligo-saccharide group, dodecyl-β-cyclodextrin (DβCDS), 18, was included.

DSH are nontoxic to planktonic bacterial growth. The toxicity of DSHs against bacterial growth in culture media was examined. At a relatively high concentration, 160 µM, none of molecules showed inhibition to the growth of planktonic Pseudomonas aeruginosa in LB broth. Being nonmicrobicidal, these agents have the potential to change or control bacterial behavior without invoking drug resistance. 35-38 We note that, however, DSH (11) inhibited bacterial (PAO1) growth on a soft agar (~0.5%) plate that was used for swarming assay (see below).

Using nonswarming mutant to screen for swarming agonists and wild type P. aeruginosa for swarming antagonists. The transposon mutant, rhlA (genotype, rhlA-E08:ISphoA/hah)39 of P. aeruginosa (PAO1), that impairs the gene that is responsible for synthesizing rhamnolipids is completely incapable of a swarming motility. 40 By the reintroducing rhamnolipids into the soft agar gel, in which rhlA mutant was inoculated, the mutant swarms again with a radial pattern similar to the wild type PA14. This result suggests that the rhamnolipids is either a ligand required for activating the swarming motility or simply a surfactant that facilitates the swarming motility. Recent work indicate that other generic surfactants such as sodium dodecyl sulfate (SDS), tetraethylene glycol mono dodecyl ether (C12EG4OH) do not reactivate the swarming motility, and small changes in disaccharide hydrocarbon structures can lead to large differences in the degree of reactivation of the swarming motility of rhlA. These results suggest that the rhamnolipids are likely a class of biological ligands that bind and trigger one or more receptors that enables swarming motility. Based on this inference, a rhlA mutant was used in a swarming experiment to screen the saccharide-hydrocarbons for agonists that can reactivate the swarming motility of rhlA. Such reactivation suggests that the active agonist may share the same active site or a remote allosteric site of the same receptor.

In contrast, the wild type P. aeruginosa produces the rhamnolipids and is capable of swarming on soft agar gel (~0.5% agar). 19 Using wild type PAO1 in a swarming experiment facilitated an antagonist assay, by which the presence and binding of saccharide hydrocarbons causing an antagonism of the receptor protein will be revealed by the inhibition of the swarming motility. We note that saccharide hydrocarbons may also promote the swarming motility, but such promotions are less unambiguous than the inhibition for wild type PAO1. Such promotion will be unambiguous in the agonist assay using the nonswarming mutant rhlA.

Disaccharide hydrocarbons and rhamnolipids exhibit dual functions of activating and inhibiting swarming motility of Pseudomonas aeruginosa. FIG. 25 demonstrates swarming motilities of wild type PAO1 and rhlA mutant on a soft agar gel, in which disaccharide hydrocarbons and rhamnolipids were homogeneously introduced. Disaccharide hydrocarbons were introduced at 85 µM, except for DISC (4), for which results from 160 µM are shown here. For rhamnolipids, a commercially available agent that was extracted from PAO1, which consists of a 5:1 mole ratio of dirhamnolipid and monorhamnolipid, was used. Using an average molecular weight of 626 g/mole, we studied the swarming motility results of PAO1 and rhlA in the presence of a range of concentrations of (1-30 µM) rhamnolipids.

Four groups of behaviors of the swarming motilities in the presence of DSHs at the concentration of 85 µM in the soft agar plate was observed. First, two saccharide hydrocarbons, DβCDS (18) and UDβC (10), showed no significant effect on the swarming motility of both wild type PAO1 and rhlA mutants (FIG. 25A). Second, two DSHs, DeβC (2) and FβC (11), showed weak activation of rhlA swarming motility and weak promotion of swarming motility of wild type PAO1 (FIG. 25B). Here, results from 160 µM of DeβC (2) were included; at 85 µM, DeβC (2) did not show a noticeable effect on the swarming motility of both strains of the bacterium. Third, five DSHs, DβM (1), UβC (3), DβC (4), TβC (5), and DαC (6), impacted the swarming motility of wild type PAO1 by causing significant amount of tendril formation in the swarming pattern (FIG. 25C). Instead of swarming outward with a circular front, the swarming bacteria start to form protrusions radially extending from the center of the inoculation spot. DSHs (1) and (4) caused wild type PAO1 to swarm with tendrils containing only straight protrusion lines of swarming bacteria, whereas DSHs (3), (5) and (6) caused the tendril to branching from the main radial lines of the swarming bacteria, forming a self-similar, fractal-like pattern (FIG. 25C). Three DSHs amongst the third group (FIG. 25C) (1), (3) and (4) showed a strong reactivation of the swarming motility in rhlA mutant with a swarming ring of bacteria having a similar diameter as that by the control, wild type PAO1 without agents. Two DSHs in this group, DSHs 5 and 6 showed no apparent reactivation of rhlA swarming. Fourth, six DSHs, DβG (8), DαR (9), SFβC (12), SFαC (13), SFβM (14), and 2-ODβC (16), inhibited the swarming motility of wild type PAO1 and showed no apparent effect on rhlA (FIG. 2D). The rest of the 3 DSHs, DβL (7), SFβL (15) and 2-ODαC (17), have a poor water-solubility and were not tested for effect on swarming motilities. We note that when testing FβC (11) at higher concentration (160 μM) with both PAO1 and rhlA, there was complete abolition of bacterial growth on the soft-agar plate. In comparison, 160 μM of FβC (11) did not inhibit the planktonic growth PAO1 in LB media.

For the rhamnolipids extract (5:1 dirhamnolipid and monorhamnolipid), at 10 μM, an activation of 38% of the swarming motility was observed on rhlA; and at 30 μM, an inhibition of 51% of swarming motility was observed for wild type PAO1. These values were obtained by comparing to the swarming area to that of wild type PAO1 under the same conditions without any added agents in the soft agar plate (FIG. 25). In comparison, at a single concentration 85 μM, DSHs exhibited different activities: some DSHs (group 2) promoted and activated swarming of PAO1 and of rhlA mutant, respectively; some DSHs (group 3) inhibited swarming of PAO1 but activated rhlA mutant's swarming, while some DSHs (group 4) inhibited swarming motility of both strains. Because rhamnolipids and DSH DeβC (2) exhibited dual functions of activating and inhibiting the swarming motilities, we speculate that disaccharide hydrocarbons, in general, possess these dual-functions, and thus manifest different activities at a single concentration due to the different binding abilities.

Disaccharide hydrocarbons and rhamnolipids exhibit "activity reversal" that transition from swam-activating to swarm-inhibiting as concentration increases. The screening of the DSHs on their effect on swarming of wild type PAO1 and rhlA mutant indicated a range of two opposite bioactivities activation and inhibition of swarming motilities. One of the most striking observations is that DSHs in the third group (1), (3), (4), and rhamnolipids, activated the swarming of rhlA mutant while inducing tendril formation in the swarming pattern of wild type PAO1. The tendril formation appears to be caused by the development of two phenotypes, the hyperactive swarming phenotypes at the tip of the tendril, and the less swarming active one at the stems and in the center of the spot. Deziel and co-workers's screening showed the over-expression of 20 genes and down regulation of 121 genes by bacteria at tip of the tendril in comparison with bacteria in the swarm center of the swarming pattern. 43 In fact, measuring the swarming area of control wild type PAO1 (without any DSHs) gave an area of ~24 cm2, and that by DSH (4) which causes tendril formation, an area of and ~13 cm2, a value ~46% smaller than the control (FIG. 25C). This result indicated that while the DSHs can activate swarming motility, they can change the phenotype of the bacteria and cause an overall apparent inhibition. Furthermore, DSH DeβC (2) showed a concentration effect by which increasing from 85 to 160 μM caused an increase of 38% of the reactivated swarming ring of rhlA with respect to swarming ring of PAO1 without agents. These observations lead us to hypothesize that, DSHs, and also rhamnolipids, are both cell signaling molecules, for which different concentrations of these molecules can modulate or regulate different bacterial behavior and control different phenotypes. To explore this hypothesis, we studied different concentration ranges of the three groups of DSHs (not including the first group of DSHs, which had no effect of swarming motility).

The effect of rhamnolipids extract, which consisted of a mixture of dirhamnolipid and monorhamnolipid in 5:1 mole ratio, was first explored. It was found that when the concentration was adjusted to 5 μM, the rhamnolipids started to activated the swarming motility of rhlA mutant, and increases the size of the swarming ring of PAO1 (FIG. 26). This positive effect of swarming activation and promotion reached a maximum at 10 μM with an swarming area of about ~9 cm2, whereas the swarming area for the control PAO1 is ~24 cm2. Surprisingly, this activation/promotion effect started to decrease at higher concentration of rhamnolipids for both rhlA mutant and wild type PAO1. At 20 μM or higher, the swarming area of rhlA became a constant of about 1.1 cm2. At 30 μM, a clear inhibition effect on swarming was observed for wild type PAO1, with a swarming area of ~11 cm2. This observation indicated an apparent activity reversal as the concentration was increased. Such an activity reversal was also observed in the early discovery of quorum sensing molecules, in which acetylated homoserine lactones (AHLs) stimulated light production in *Photobacterium fischeri* and the amount of light produced increased over the range 0.003-3 μg/mL and then decreased at higher concentrations for both natural and synthetic AHLs.

The active DSHs (Group 2, 3 and 4 of FIG. 25) all exhibited a trend of swarming promotion at low concentration and swarming inhibition at high concentration. FIG. 26 shows the concentration ranges of DSHs, in which there is an impact on the swarming motility of wild type PAO1 and rhlA mutant. For any molecules, the transition concentrations were different for the two strains (from activating to non-activating for rhlA mutant, and from promotion to inhibition for PAO1). Furthermore, the transition concentrations were also different for different DSHs, and could be roughly categorize into two groups, early and late transition at relatively low and high concentrations (FIG. 27 & Table 1). Whereas rhamnolipids and DSHs (14) and (12) exhibited low transition concentrations at 10 μM, 10 μM and 8 μM for rhlA; 20-30 μM, 7.5 μM, 10-20 μM for PAO1, respectively; DSHs (4), (5) and (8) exhibited these transition at higher concentrations at 45-56 μM, 40 μM and 35 μM for rhlA; 20-30 μM, 20-30 μM and 35-50 μM for wild type PAO1, respectively. Table 1 shows the different transition concentrations of DSHs and rhamnolipids for rhlA mutant and wild type PAO1. In general, the transition concentrations for activating rhlA mutant were slightly lower than the transition concentrations for inhibiting wild type PAO1 swarming. The agents that exhibited low transition concentrations (12, 14, and rhamnolipids) activated smaller rings in the swarming pattern of the rhlA mutant than that by the agents with high transition concentrations (FIG. 27). This result suggest that the less potent swarming inhibitors, (4), (5) and (8), were more capable at activating the rhlA mutant in swarming motility. At these transition concentrations between the two opposite bioactivities, some DSHs induced tendril formation, some did not. For rhlA mutant, only DβC (4) induced tendril formation around ~56 μM; while for PAO1 tendrils were induced by DβC (4) at 20 μM, TβC (5) at 30 μM, and SFβM (14) at ~7.5 μM.

We also note that by measuring the swarming area of activated rhlA mutant, as the concentration increased, DSHs (4) and (5) appeared to cause another activation of swarming at about 160 µM after first inhibition at around 50 µM (FIG. 27). Swarming motilities at additional concentrations supported this observation. Together, these results indicate that both rhamnolipids and active DSHs have the dual function of acting as an agonist by activating the swarming motility at low concentrations, but as an antagonist by inhibiting the swarming motility at high concentrations.

TABLE 1

Concentrations of DSHs at which they exhibit activity reversal for swarming promotion of rhlA mutant and swarming inhibition of PAO1.

| Compound | rhlA | PAO1 |
| --- | --- | --- |
| Rhamnolipids | ~10 µM | ~20-30 µM |
| SFβM (14) | ~10 µM | ~7.5 µM |
| SFβC (12) | ~8 µM | ~10-20 µM |
| DβC (4) | $^a$~45-56 µM | ~20-30 µM |
| TβC (5) | ~40 µM | ~20-30 µM |
| DβG (8) | ~35-50 µM | ~50-60 µM |

Disaccharide hydrocarbons SFβC (12), SFβM (14) and DβC (4) dominated rhamnolipids at inhibiting the swarming motility of PAO1. Examining the result indicated that at 10 µM, (14) is more effective than rhamnolipids at activating rhlA swarming, a ~14 cm2 swarming ring was observed for (14), whereas only a ~9 cm2 ring was observed for rhamnolipids—about a ~20% reduction. Furthermore, at 20 µM, (12), (14), and (4) all exhibited stronger inhibition than rhamnolipids at inhibiting the swarming motility of wild type PAO1. Comparing (12) and rhamnolipids at 20 µM, swarming of wild type PAO1 was completely inhibited by (12) with swarm ring of ~1.2 cm2 (~5%) as compared to 24 cm2 (100%) for PAO1 without any DSHs. At concentration lower than 20 µM, all three DSHs also exhibited stronger inhibition of swarming motility of wild type PAO1 than rhamnolipids. Whereas (14) and (4) induced tendril formation in wild type PAO1, rhamnolipids were not able induce such a phenotypic bifurcation effect. These results indicated that (12), (14) and (4) not only suppressed the effect of rhamnolipids secreted in situ by wild type PAO1, but also had a stronger inhibition effect when compared to the externally added rhamnolipids in the same concentration range.

Competition assays suggests SFβC (12) is a stronger ligand than DβC (4). Presumably, both of the DSHs that activate and inhibit swarming motility of P. aeruginosa target the same putative receptor of rhamnolipids. To further explore this possibility, a competition assay was conducted by introducing both SFβC (12) and DβC (4) at different concentrations into the soft agar gel and observed the swarming motility of rhlA mutant. Both SFβC (12) and SFβM (14) had inhibited swarming of PAO1, which suggested that either SFβC (12) and SFβM (14) block the receptor site of the in situ produced rhamnolipids or they bound to an allosteric site of the receptor remotely, abolishing the receptor's binding ability to rhamnolipids. As rhlA mutant produces no rhamnolipids, this mutant provides an ideal platform for examining the competition between different synthetic DSHs for the putative receptor. At 40 µM, DβC (4) activated the swarming motility of rhlA mutant. At 20 µM, SFβC (12) did not activate the swarming motility of of rhlA mutant. It is not entirely clear if SFβC (12) is inhibiting the receptor in rhlA or SFβC (12) has no effect at this concentration on rhlA mutant, although SFβC (12) did inhibit the swarming activity of wild type PAO1 at 20 µM. Thus, in this competition assay, the concentration of DβC (4) was kept at 40 µM, and the concentration of SFβC (12) was increased incrementally to 0.5, 10, 20, and 40 µM (FIG. 28). The swarming motility showed that up to 10 µM, SFβC (12) did not interfere with the swarming reactivation of rhlA mutant by 40 µM of DβC (4). But when the concentration of SFβC (12) is increased to 20 µM, the swarming motility is completely inhibited while 40 µM of DβC (4) was still present. This result is consistent with the effect of SFβC (12) on wild type PAO1, for which 0.5 to 10 µM promoted swarming and higher concentrations inhibited swarming. This competition assay suggests that SFβC (12) is a stronger binding ligand (with antagonistic activity) than DβC (4), and that molecules showing early transition (at low concentration) of swarming activating to swarming inhibition are likely stronger binding ligands than "late" transition molecules.

DSHs showed a similar trend of structural-activity correlation for antiadhesion and antibiofilm (inhibition and dispersion) activities. As rhamnolipids are known to be critically important for building channeled biofilm by P. aeruginosa, and under conditions that cause over production of rhamnolipids, bacteria appears to be dispersed from the biofilm. These results suggest that the disaccharide hydrocarbons presented in this study may also have an impact on the biofilm formation. On the other hand, N-acetylated disaccharides hydrocarbons have been found to inhibit bacteria adhesions on stainless steel and on polystyrene surfaces. These findings suggest that disaccharide hydrocarbons may also have an impact on the adhesion and biofilm formation by P. aeruginosa.

The effect that DSHs have on the adhesion of PAO1-EGFP on polystyrene surface (microtiter plate) was also examined. PAO1-EGFP is a P. aeruginosa strain that constitutively expresses green fluorescent protein. In the adhesion assays, PAO1-EGFP was grown in microtiter plate for 24-hours in LB-media with (160 µM) or without DSHs. After 24-hours, the fluorescent signal obtained from surface adhered PAO1-EGFP was measured. Percent reduction in fluorescence was calculated by comparing fluorescent signal from PAO1-EGFP grown in LB-media with the signal from wells that had DSHs (FIG. 29A). To study the effect of DSHs on biofilm formation, Pseudomonas aeruginosa (PAO1) was grown in LB-media with (160 µM) or without DSHs at 37° C. under static conditions within wells of microtiter plates. After 24 hours, the surface attached biofilms adhering to the bottom of the wells were stained with crystal-violet dye and the biofilm was quantified by measuring absorbance at 600 nm (OD600). The percent inhibition was calculated by comparing biofilm content of wells with no added agents (control) with the biofilm content from wells that had 160 µM of DSHs (FIG. 29A). Similar to inhibition, the surface attached biofilm after dispersion with DSHs was quantified with crystal-violet staining and absorbance measurement at 600 nm, except that for dispersion, biofilm was first grown for 1 day in just LB-media without any DSHs after which DSHs were added and plates were incubated for additional 24 hours followed by quantification (FIG. 29B).

A screening of the structures shows that, at 160 SFβC (12), SFαC (13), DβC (4) and SFβM (14) exhibited more than 60% of inhibition of bacterial biofilm formation on the microtiter wells; DβM (1), DβG (8), TβC (5), UβC (3), DαR (9), 2-ODβC (16) and DαC (6) showed between 50 to 20% of biofilm inhibition, and DeβC (2), DβL (7), UDβC (10), FβC (11) and DβCDS (18) showed insignificant biofilm inhibition FIG. 29A. Interestingly, an overall similar trend was observed for bacterial adhesion inhibition assay at the same concentration, with the exceptions that (9) and (18) did not show significant biofilm inhibition, but showed 63% and 29% adhesion inhibition for *P. aeruginosa* (FIG. 29A). Additionally, the biofilm formed by PAO1-EGFP on stainless steel coupons grown in LB-media for 24-h supplemented with 5 DSHs, SFβC (12), SFαC (13), DβC (4), DeβC (2) and DβL (7) and with no added agents were viewed under confocal laser scanning microscope (CLSM). PAO1-EGFP constitutively produces green fluorescent proteins in culture that can be viewed under CLSM. CLSM micrographs show that 160 μM of SFβC (12), SFαC (13) and DβC (4) decreased the fluorescence signal significantly as compared to the steel coupon grown in just LB-media indicating that a lesser bacterial cell density (and hence lesser biofilm) on the steel coupons. Also, the fluorescence thickness as indicated on the Z-axis of these micrographs indicate a much thinner bacterial coverage on steel coupons that were placed in media containing potent DSHs. Contrary to this, steel coupons placed in LB-media with two DSHs, DeβC (2) and DβL (7) had bacterial surface coverage comparable to that of control. The findings of the CLSM-based assays were consistent with the results of CV-dye based assay for biofilm inhibition.

Dispersion of already formed biofilm is more challenging than inhibiting the formation of biofilm by introducing agents at the beginning of the assay. But dispersing pre-formed biofilm is more relevant to applications for which has already formed. The DSHs were also screened for their ability to disperse a 24 hour old biofilm. The activities for inhibition of biofilm formation and bacterial adhesion and for dispersion of biofilm were plotted with the same order of agents in FIG. 29A and FIG. 29B, respectively. With a few exceptions, an overall similar trend of structure-activity correlation was observed between biofilm inhibition, adhesion inhibition and biofilm dispersion. The percentages of biofilm remaining in dispersion assays were always higher than those in the biofilm inhibition assays. The potent DSHs, SFβC (12), SFαC (13), SFβM (14) and DβC (4) that exhibited strong inhibition of biofilm formation also were the most potent dispersing agents that dispersed more than 60% of the 24-h old biofilm. Other DSHs, except DβCDS (18), dispersed between 20-60% of 24-h biofilm. The DβCDS (18) appeared to have promoted biofilm formation instead of causing dispersion of 24-h biofilm. The exception that broke the trend of structure-activity correlation between inhibition and dispersion was 2-ODβC (16) with not a significant difference in the magnitude.

Structure-activity study reveals important structure features for strong bioactivities. Examining the structures of DSHs and their bioactivities revealed a set of important structural features that is common for influencing all three bacterial behaviors swarming activation, biofilm inhibition and adhesion inhibition. First, the size and stereochemistry is important for activity. Glucoside, DβG (8); mono-rhamnoside, DαR (9), and β-cyclodextrin, DβCDS (18)-based agents, all had weak anti-biofilm activity whereas disaccharide stereochemistry, maltose and cellobiose showed strong activities for all three processes. Second, for disaccharide hydrocarbons, cellobiose having a stereochemistry of Glcβ(1∝4)Glc appeared to be more active than maltose stereochemistry—Glcα(1→4)Glc. Lactose, Galβ(1→4)Glc, based molecule, DβL (7), exhibited low activities, but had a low solubility in water. Thus, a structural correlation conclusion cannot be drawn. Third, a chain length of twelve carbons appeared to be optimum for showing maximum activities for disaccharide hydrocarbons. For example at 160 μM, DeβC (2) and UβC (3) having 10 and 11 carbons in the aliphatic chain showed no and insignificant anti-biofilm activity, respectively, whereas DISC (4) having a 12-carbon aliphatic chain exhibited 62% inhibition of biofilm. Most importantly, bulky aliphatic chain (3,7,11-trimethyl-dodecane) enabled DSHs (SFβC (12) and SFβM (12) to be most potent at controlling all three bacterial activities. The structure also dominated over natural rhamnolipids that are produced in situ by *P. aeruginosa* during both inhibition and swarming activities of the bacteria. In comparison, DSHs FβC (11) and UDβC (10) having unsaturated hydrocarbons that were relatively smaller than the saturated version showed 12% and 17% inhibition at 160 μM. Interestingly, DSHs 2-ODβC (16) and 2-OdαC (17), having double aliphatic chains that were similar to rhamnolipids were not active for biofilm inhibition or dispersion (FIG. 29A) but 2-ODβC (16) did exhibit inhibition of PAO1 swarming.

Dose-dependent study revealed "activity reversal" of rhamnolipids on biofilm inhibition. Identifying the important common structures for all three bioactivities, dose-dependent studies on biofilm inhibition and biofilm dispersion with selected DSHs that exhibited high activities, SFβC (12), SFαC (13), SFβM (14) and DβC (4; only inhibition) were performed. These dose-dependence were compared to that by rhamnolipids extract. For biofilm inhibition assays, the rhamnolipids extract exhibited an increase in biofilm inhibition as the concentration was increased, but surprisingly reaching a maximum of 65% inhibition at 42 μM, and the inhibition % drastically decreased as the concentration was increased further. For instance, at 85 μM, the inhibition by rhamnolipids extract decreased to 46%. Further increase in concentration actually promoted biofilm formation, at 160 μM, 114% of PAO1 biofilm was observed in comparison with biofilm without agents (100%). This activity reversal of rhamnolipids on biofilm inhibition was not observed for the other four DSHs studied (FIG. 30). All four DSHs, SFβC (12), SFαC (13), SFβM (14) and DβC (4) showed an increase of biofilm inhibition, followed by a plateau. DSH SFβC (12) showed a half maximal inhibitory concentration ($IC_{50}$) ~9.9 μM; SFαC (13) ~32 μM; DβC (4) ~72 μM; and SFβM (14) ~102 μM. Because of the activity reversal, $IC_{50}$ for the rhamnolipids was not calculated. These results also indicate that SFβC (12) was more potent than rhamnolipids at inhibiting biofilm formation, whereas as the other three DSHs were more effective than rhamnolipids only at higher concentrations. The lack of biofilm inhibition activity of rhamnolipids at higher concentration also appeared to be consistent with the results that disaccharide-based lipid, 2-ODβC (16) was not effective at inhibiting the biofilm formation, but inhibits the swarming activities of PAO1.

Active DSHs dominates rhamnolipids in dispersing pre-formed biofilm. For dispersion assays, rhamnolipids, however, were not effective for dispersing the 24-h biofilm. About 80% of the biofilm remained (~20% dispersion) after rhamnolipids were introduced to the already formed biofilm (24 -h old). As the concentration of rhamnolipids increased, the amount of biofilm actually increased (FIG. 31). In comparison, the three active DSHs, SFβC (12), SFαC (13) and SFβM (14), showed conventional biofilm dispersion activities, by which the percentage of dispersed biofilm reached a plateau as the concentration increased. This dose-dependence study showed that DSH SFβC (12) exhibited a half-maximal dispersion concentration ($DC_{50}$) of ~44 μM, SFαC (13) ~89 μM and SFβM (14) ~126 μM. These $DC_{50}$ were high in comparison with other known agents that also disperse biofilm formation.

Because the structures of these class of molecules are also surfactants, it is not clear before these results whether any activity from these molecules is due to a mere physical effect of the surfactant properties or a biological effect, by which a receptor on bacterial surface is being blocked by the molecules leading to either an antagonistic or an agonistic effect. The same question was also posted for rhamnolipids. Several aspects of the results in this work suggest that both rhamnolipids and DSHs likely are ligands for certain receptors on the bacteria. First, generic surfactants such as SDS and C12EG5OH did not incur any bioactivity for both swarming reactivation and biofilm inhibition. Second, only selected DSHs activated the swarming motility of the non-swarming mutant rhlA, while all the DSHs shared surfactant properties. Third, all the active DSHs and rhamnolipids exhibited "activity reversal" in controlling the swarming motility of mutant rhlA, and thus showed the dual bio-function of activating and inhibiting swarming motility at different concentrations. This "activity reversal" appears to be a recorded but overlooked phenomenon of the classical bacterial signaling molecule, N-(3-oxohexanoyl)-3-amino-dihydro-2(3H)-furanone, for which the receptor was later determined. 51-53 We note that the two important quorum sensing systems that control $P.$ $aeruginosa$ are las and rhl circuits. We conducted the antagonistic gene reporter assay to investigate the effect of two DSHs, SFβC (12) and SFαC (13) on las and rhl quorum sensing circuits of $Pseudomonas$ $aeruginosa$, by using two reporter strains, PAO1/plasI-LVAgfp and PAO1/prhlI-LVAgfp. The two reporter strains secrete natural autoinducers that bind receptor proteins, lasR and rhlR activating either lasI or rhlI genes respectively. The activation of either lasI or rhlI genes in turn expresses green fluorescent protein that is encoded by the plasmid. 57 The results indicated that neither SFβC (12) nor SFαC (13) caused a significant change in the fluorescence of two reporter strains, PAO1/plasI-LVAgfp and PAO1/prhlI-LVAgfp (see Supporting Information, S6), suggesting that DSHs do not interfere with the quorum sensing circuits of $Pseudomonas$ $aeruginosa$.

Addition of pili peptide reduces the biofilm inhibition by DSHs. Kohler and coworkers suggested that type IV pili are critically important for rhamnolipids-enabled swarming motility of $P.$ $aeruginosa$. On the other hand, Randall and coworkers also showed that the adhesion of $P.$ $aeruginosa$ to epithelial cell surface and polystyrene surfaces is mediated by pilus protein. While PA pili specifically recognize D-Gal-Nac(1→4)-β-D-Gal disaccharide ligand, the pili assisted epithelial cell binding domain is located between residues 128-144 on the C-terminal region of PilA, the pili structural protein. It has been demonstrated that among different strains of $P.$ $aeruginosa$, this 17 amino acids region of PilA is semi-conserved and usually has a di-sulfide loop formed by the two conserved cysteines. To explore a putative receptor for the DSHs, the minimal 17 amino acids residues sequence peptide that contained residues known to exist on C-terminal region of $P.$ $aeruginosa$ PAO strain pilus [N'—Ac-ACKSTQDPIVIFTPKGCDN—OH—C'] was synthesized. This synthetic peptide is known to recognize dis-aacharide GalNAc-Gal. The peptide was synthesized and the two cysteines at positions 129 and 142 were air oxidized to form an intra-molecular disulfide loop, resembling the natural cell binding domain. This looped sequence was named the pili peptide, although previously it had been described as PAO(128-144) oxidized. As a control, a scrambled pili peptide was synthesized by changing the cysteines at positions 129 and 142 position to alanines, [N—Ac-AAK-STQDPMFTPKGADN—OH—C'], which has been described previously as PAO(128-144) (C129A/C142). We found that SFαC (13) at 85 μM alone inhibited about 70% of PAO1 biofilm, presence of control scrambled pili peptide (85 μM) along with SFαC (13; 85 μM) caused an inhibition of 65% of the biofilm, whereas presence of the pili peptide (85 μM) and SFαC (13; 85 μM) reduced the inhibition to 30% (FIG. 32). These results suggest that the pili peptide likely interferes with the binding between the pili receptor and SFαC (13) whereas the control scrambled pili peptide had little inference, and that pili protein is a potential receptor for DSHs.

Comparing the effect of DSHs on swarming motility and biofilm inhibition reveals that inhibiting biofilm formation had a more stringent structure requirement than activating the swarming motility. For example, DeβC (2), UβC (3), DOG (8) and TβC (5) all activated the swarming motility of rhlA mutant, but did not show significant inhibition of PAO1 biofilm. DSHs that were potent PAO1 biofilm inhibitors, SFβC (12), SFαC (13) and SFβM (14) were also inhibitors for PAO1 swarming motility. But not all PAO1 swarming inhibitors, such as 2-ODβC (16) and DαR (9) exhibited good anti-biofilm activities. The DSHs that did not show anti-biofilm activities, including DβC (2), UDβC (10), FβC (11) and DβCDS (18) exhibited no apparent effect on PAO1 swarming. For these agents, either there is no binding between these agents and the putative receptor or the binding did not trigger a signaling effect. Several DSHs, including DβM (1), UβC (3), DβC (4), TβC (5), DαC (6) and SFβM (14) induced tendril formation in the swarming pattern of PAO1, which by itself did not form tendril. These DSHs are likely causing a bifurcation of PAO1 into two phenotypes at the same time; this phenomenon is an ongoing subject of our study.

Overall, different stereochemistries of disaccharides were effective for both biofilm and swarming inhibition, but large oligosaccharide groups such as β-cyclodextrin rendered the molecule inactive. In contrast, the structural details of the aliphatic chains incurred a relatively more significant impact for high activity on controlling the swarming motility and biofilm formation. In particular, bulky aliphatic chain involving 3,7,11-trimethyl-dodecane caused the highest activities among all the DSHs for both cellobiose and maltose stereochemistry.

A class of disaccharide hydrocarbons with different stereochemistries and aliphatic chain structures were studied for their ability to activate and inhibit the swarming motility of $P.$ $aeruginosa$ and its nonswarming mutant rhlA, and to inhibit the bacterial adhesion and biofilm formation on polystyrene surfaces. Among the eighteen DSHs, a common set of structures was found to be active for controlling all these bioactivities of $P.$ $aeruginosa$. These DSHs included both cellobiose and maltose stereochemistries, along with a bulky hydrocarbon chains comprised of 3,7,11-trimethyl-dodecane a structural moiety obtained by hydrogenation of farnesol molecules. For the influence on swarming motility, all active DSHs exhibited dual functions that transition from swarm-activating to swarm-inhibiting as the concentration was increased in the soft agar plate. The DSHs with low transition concentrations were also strong anti-adhesion and anti-biofilm agents. This "activity reversal" in controlling swarming motility was also observed for rhamnolipids extracts that consist of dirhamnolipid and monorhamnolipid in 5:1 mole ratio. In contrast, whereas active DSHs showed a plateau behavior in dose dependent study on biofilm inhibition, rhamnolipids showed "activity reversal", for which the biofilm inhibition activity decreased as the concentration is increased. Three DSHs, saturated farnesyl-β-cellobioside SFβC, (12) saturated farnesyl-α-cellobioside SFαC (13) and saturated farnesyl-β-cellobioside SFβM, (14), exhibited dominating effect over rhamnolipids at inhibiting the swarming motility of wild type $P.$ $aeruginosa$.

Furthermore, while active DSHs were effective at dispersing 24-h old biofilm, rhamnolipids did not have a significant influence on the preformed biofilm. Because this class of DSHs do not inhibit the growth of the bacteria, their activities at inhibiting and dispersing the biofilm formation have the potential for further application development that does not invoke drug resistance.

Standard solvents, and media were purchased from commercial sources (Sigma-Aldrich, Fisher, Acros) and used as received. Column chromatography was performed using Silicycle, Silia-P Flash Silica Gel with 40-6µ mesh size.

The synthesis of all saccharide-hydrocarbons was done according to Scheme 1 using a literature reported synthetic route with some modifications. Briefly, disaccharides (cellobiose, maltose, lactose) and monosaccharide (rhamnose) were per-O-acetylated using a binary mixture of AcBr/AcOH with simultaneous mono-bromination at anomeric position. Glycosidation of aceto-bromo sugars with aliphatic alcohols was done using acid catalysts (FeCl3 or Hg(CN)2 and in either MeCN (for β-anomer as major product) or MeNO2 (for α-anomer) as solvent. The α/β anomers were resolved by column chromatography and further deacetylated by methanolic MeONa followed by neutralization by H+ amberlite resins to pH 6.5 (Zemplem deacetylation). Synthesis of cyclic-hepta-saccharide hydrocarbon was done according to Scheme 2.

R95 (5:1 di-rhamnolipids:mono-rhamnolipids, 95% pure, avg molecular weight 626 g/mole) was obtained from Agae technologies and used as purchased. Water was purified using a Millipore Analyzer Feed System. Flat-bottomed polystyrene 96-well microtiter plates (untreated) (Costar 3370) were used to perform all biological assays (except assays that required fluorescence measurements). For measuring fluoresecence, flat-bottomed 96-well microtiter plates with black walls (Xlear, Greiner-One 655096) were used. Measurement of absorbance (at 600 m, OD600) was usual performed with 2004 of culture-media in microtiter plates on a Biotek ELx800 ™ absorbance microplate reader and data was analyzed with Gen5™ data analysis software. Quantification of biofilm was done using standard crystal violet (CV) dye based static-biofilm assay. The quantified biofilm reported is the surface attached (SA) biofilm at the well bottoms, for each assay, total biofilm was also quantified (not reported here) and the trend of percent biofilm inhibition for SA and total were the same. For quantifying fluorescence, Synergy 2 multi-mode microplate reader with Gen5 data analysis software was used to detect GFP signal at an excitation wavelength of 500 nm and emission wavelength of 540 nm. For positive controls, wells with no-agents were used. For each biological assay, at least 3 repeats (with similar results) were done and data represented here for each agent is the average of readings from 4-replicates wells from one single experiment. Graphs were plotted using Microsoft Excel (2007) and half maximal inhibitory concentration for both biofilm inhibition and dispersion ($IC_{50}$ and $DC_{50}$) were calculated by fitting linear values into a logarithmic equation, $y = \min(x)$.

*Pseudomonas aeruginosa* strains PAO1 and PAO1-EGFP were obtained from Dr. Guirong Wang (Upstate Medical University). *Pseudomonas aeruginosa* transposon mutant strain PW6886 (rhlA-E08:ISphoA/hah) was obtained from two-allele library. PAO1 (plasI-LVAgfp), PAO1 (prhlI-LVAgfp) strains were prepared in lab using previously reported protocol. The plasmid plasI-LVAgfp and prhlI-LVAgfp were obtained from Dr. Hiroaki Suga (The University of Tokyo) and were maintained by adding 300 µg/mL of carbenicillin in culture media. Freezer stocks of all strains were stored at −80° C. in LB media with 20% glycerol. All strains were grown at 37° C. in a rotary-shaker (at 250 rpm) in Luria Bertaini (LB) media (composition of LB media, 10 g/L tryptone, 5 g/L yeast extract, and 10 g/L NaCl). All biofilm inhibition, dispersion and adhesion assays were performed in LB-media and plates were incubated at 37° C. for 24 hours (except for adhesion assay, 3 hours) under static conditions.

Stock solution of disaccharide hydrocarbons (DSHs). Stock solution (~11.5 mM) of all synthesized and commercially available DSHs were prepared in autoclaved water and further sterilized by filtering through cellulose acetate syringe filter (0.2 µm pore size, GVS filter technology) into sterilized vials. The vials containing sterilized DSHs stocks were capped and stored at −20° C. and thawed prior to each use. Appropriate volume of sterile water was added to positive controls (no agents) in all assays to eliminate the effect of water. Stock solution of DβL (7), SFβL (15) and 2-ODαC (17) were prepared in sterile water and 200 proof EtOH in 90:10 ratio. For positive controls involving DβL (7), SFβL (15) and 2-ODαC (17) appropriate volumes of 90:10, H2O:EtOH was added.

Swarm agar plates were based on M8 medium supplemented with 0.2% glucose, 0.5% casamino acid, 1 mM MgSO4 and 0.5 Bacto agar. 17 For each set of experiment all the swarm plates were poured from same batch of agar and allowed to dry for 1 h before inoculation of bacteria. Bacterial culture (3 µl) (wild type PAO1 or rhlA mutant) with OD600 between 0.5 was inoculated on the solidified agar plates. Swarm agar plates were incubated at 37° C. for 12 h and then incubated for additional 12 h at room temp. Chronological images of swarm plates were taken using a camera. To measure swarming area, sizes of the petridish in all swarming images were adjusted to a pre-assigned diameter and images were printed on copying paper (Xerox-business 4200). Weight of a 1 $cm^2$ copy paper square was roughly ~8.0 mg. swarming images on the copy paper were cut and weighed, the swarm area was calculated by dividing the weight of image by weight of 1 $cm^2$ square (8 mg).

Antimicrobial activities of disaccharide hydrocarbons against planktonic growth. Overnight inoculum of PAO1 was sub-cultured to an OD600~0.1 and then aliquoted (200 µL) into the wells of a micro-titer plate and DSHs (~160 µM) were then added to assigned wells. Wells with no-agents were created as a positive control. The micro-titer plate was then placed in a rotary shaker (250 rpm at 37° C.) and optical density was measured after regular intervals of time using Biotek ELx800 ™ absorbance microplate reader (BioTek Instruments, Inc., Winooski, Vt.) using Gen5™ data analysis software. The OD600 values were taken in sterile conditions over 24 h. The OD600 values were plotted against time to obtain a growth curve for planktonic growth with or without agents.

Crystal violet (CV) based-biofilm inhibition assay. Inhibitory effect of all synthesized disaccharide hydrocarbons on biofilm formation of *Pseudomonas aeruginosa* (wild type PAO1) was determined by static biofilm inhibition assay using crystal violet staining. Overnight culture of PAO1 were sub cultured in LB media to OD600 of 0.01 and further the OD600 was allowed to reach ~0.1. The bacterial subculture (200 µL) was then added into the wells of a micro-titer plate. Predetermined concentrations of DSHs were added to respective wells containing sub culture by pipetting out fixed volume of sterile aqueous stock solutions (except DβL (7), SPOT, (15) and 2-ODαC (17), which were introduced as stocks prepared in H2O 2O and EtOH (90:10) solutions). The microtiter plates were then wrapped in GLAD Press n' Seal® (saran wrap) and further incubated under stationary conditions for 24 h at 37° C. After 24 h incubation, the culture media was discarded by pipetting carefully (without disrupting biofilm), the plate was then washed once with sterile water (200 µL) and allowed to dry at 37° C. for ~30 mins. Microtiter plates were then stained with 0.1% aqueous solution of crystal violet (CV) (200 µL) at rt for ~30 mins. Following this, the CV stain was removed and plate was again washed with sterile water (200 µL). Resultant CV stain in the well was then solubilized by adding 100 µL of 30% AcOH solution (in water) and mixing gently by pipetting. The surface attached (SA) biofilm was quantified by measuring OD600. Following this, additional 1154 of CV solution was added to each well to quantify total biofilm. Negative control lane, wherein no biofilm was formed was also stained with CV and its OD600 reading was subtracted from each well that contained culture media with DSH or without DSH. The percent inhibition was calculated by the comparing of the OD600 for biofilm grown in the absence of compound (No agent) versus biofilm grown in the presence of DSH under identical conditions.

Overnight culture of PAO1-GFP (supplemented with 300 µg/mL of carbenicillin) was subcultured at 250 rpm and 37° C. to an OD600 of 0.01 in LB medium. When the OD600 of subculture reached ~0.1, aliquot of the subculture (200 µL) was transferred to the wells of black microtiter plate and DSH (resultant conc. 160 µM) were added to assigned wells. Positive control were created that had no DSHs but appropriate volume of sterile water. The black well 96-well plate was wrapped in GLAD Press n' Seal® and then incubated at 37° C. for 2 h. Following incubation for 2 h, the bacterial culture from the wells was discarded and each well was washed once with saline water (0.85 w/v % aqueous NaCl solution). Aliquot of fresh LB medium (200 µL) was then added into the wells and fluorescence was measured at an excitation wavelength of 500 nm and an emission wavelength of 540 nm by using a Synergy 2 multi-mode microplate reader with Gen5 data analysis software. Signal from wells containing just LB medium was subtracted from all the wells.

Confocal laser scanning microscopy (CLSM) based biofilm inhibition assay. Steel coupons (~1×1 cm) were washed with EtOH, dried under a stream of nitrogen and then sterilized in an autoclave. Overnight culture of PAO1/EGFP (OD600 ~1.0) grown in LB media (supplemented with 300 µg/mL of carbenicillin), was sub-cultured to OD600~0.01 and then the OD600 was allowed to reach ~0.1. Aliquot (600 µL) of PAO1/EGFP subculture OD600~0.1 was then added into the wells of a 24-well micro titer plate. DSHs were then introduced into the assigned wells to reach a resultant concentration of 160 µM. Bacterial sub-culture with no agent served as positive control. Sterile steel coupons were then placed into the wells and the plates were wrapped with saran wrap and incubated for 24 h at 37° C. under static conditions. After 24 hours, the steel coupons were removed and washed by dipping in PBS buffer (2 washes) and the dried by holding with a forcep and gently dabbing the edge on a bleached paper (KIM wipes). The dried steel coupons were viewed under confocal laser scanning microscope (CLSM). Images were taken at 4 random locations on each steel coupons. Z-stacked images were also taken to determine the relative thickness of the biofilm.

Crystal violet based assay for quantifying dispersion of 1-day old PAO1 biofilms were Plate for set up similar to inhibition assay with a slight modification. Wells of the micro-titer plate was inoculated with (200 µL) bacterial subculture (PAO1 subculture OD600 ~0.1). The plates were incubated at 37° C. for 24 hours to allow biofilm formation. After 24 hours, bacterial culture was gently pipetted out and appropriate volume of DSH were added followed by addition of fresh LB medium (200 µL). The microtiter plate was incubated for an additional 24 hours at 37° C., following which, similar to work up of inhibition assay, culture was removed, wells were washed and CV-dye was introduced, followed by washing and destaining with 30% AcOH solution in water and quantification at 600 nm. Here again, only the surface attached biofilm dispersed was reported by comparing wells with DSHs with wells with no agent.

Dose dependence assays for biofilm inhibition and dispersion. DSHs that were most potent at 160 µM (exhibiting >60% biofilm inhibition and dispersion) were selected for determining the dose dependence. Both for biofilm inhibition and dispersion, predetermined volumes of DSH stocks were added to the assigned wells to span a concentration range between 0.5 µM-170 µM. Percent biofilm inhibition of dispersion was calculated by comparing to wells with no agent. The percent biofilm inhibition or dispersion was plotted versus concentration of DSHs. The linear values were logarithmically curve fitted using equation y=min (x). The half maximal inhibitory concentration for both biofilm inhibition and dispersion ($IC_{50}$ and $DC_{50}$) were thus obtained.

Strains PAO1/plasI-LVAgfp and PAO1/prhlI-LVAgfp were grown overnight in LB-media that was supplemented with 300 µg/mL carbenicillin and after 16 hours, the bacteria were sub cultured in LB media (supplemented with 300 µg/mL carbenicillin) to OD600 as 0.01. The OD600 was allowed to reach 0.1 and then 200 µL of culture was aliquoted into the wells of 96-well microtiter plate. DSHs were then added to assigned wells at two different concentrations (85 µM and 160 µM). No agent was added to the well for positive control. The plates then incubated at 37° C. for 24 h in a rotary shaking incubator (250 rpm). The culture from each well was then transferred to corresponding wells of a black walled flat-bottom, 96-well plate (µClear, Greiner-One 655096). The fluorescence and OD absorbance in each well was measured by Synergy 2 multi-mode microplate reader with aGen5 data analysis software. Background signals from LB medium were deducted from all samples. Fluorescence was measured at an excitation wavelength of 500 nm and an emission wavelength of 540 nm.

Synthesis of oxidized pili peptide PAO(128-144)ox and scrambled pili peptide PAO(C129A/C142A) Scrambled. Synthesis of the peptides were done according to previously reported procedure. Fmoc-based solid phase peptide synthesis was used and the purification was done by reversed-phase high performance liquid chromatography (HPLC). Air oxidation was employed to oxidize the two cysteines residues in PAO(128-144) sequence to generate a di-sulfide linkage. For this a dilute solution (6 mg/4 mL) of unoxidized pili peptide was made PBS buffer (pH 7.8) containing 10% DMSO, and solution was stirred in air and monitored by reversed phase HPLC and MALDI-TOF. Following the oxidation of pili peptide, purification was done over reverse phase HPLC. PAO(128-144)ox sequence is N'Ac-A-C—K-S-T-Q-D-P-M-F-T-P-K-G-C-D-N—OH—C'. While for generating scrambled pili peptide, cysteines at positions 129 and 142 were replaced with alanines to generate the following sequence; PAO (C129A/C142) Scrambled; N' Ac-A-A-K-S-T-Q-D-P-M-F-T-P-K-G-A-D-N—OH—C'.

EXAMPLE 5

As seen in FIG. 34 and FIGS. 35A and 35B, several compounds falling within a general structure were testing according to the present invention as follows.

Plasmids plasI-LVAgfp and prhlI-LVAgfp were provided by Dr. Hiroaki Suga (The University of Tokyo). Strains PAO-JP2 (plasI-LVAgfp) and PAO-JP2 (prhlI-LVAgfp) were obtained from Dr. Helen Blackwell. PAO1-GFP strain was provided by Dr. Guirong Wang (Upstate Medical University). Non-swarming mutant of *P. aeruginosa*, rhlA (PW6886) was obtained from PA two-allele library. 300 µg/mL of carbenicillin was added to maintain the plasmids of strains PAO1-GFP, PAO1 (plasI-LVAgfp), PAO1 (prhlI-LVAgfp). All the bacterial strains were grown in Luria-Bertani (LB) medium containing 10 g/L tryptone, 5 g/L yeast extract, and 10 g/L NaCl at 37° C. For biofilm inhibition and dispersion assays 95% M9+ medium with 5% of LB broth was used unless otherwise stated. M9+ medium contained 47.7 mM $Na_2HPO_4$, 21.7 mM $KH_2PO_4$, 8.6 mMNaCl, 18.7 mM NH4Cl, 1 mM $MgSO_4$, 0.1 mM CaCl2, 0.4% L-Arg, 0.5% CAA, 0.2% anhydrous α-D(+)-glucose, 0.2% sodium succinate dibasic hexahydrate, 0.2% citric acid monohydrate, and 0.2% L-glutamic acid monopotassium salt monohydrate.

Stock solution of all the agents (11.5 mM) were prepared in autoclaved water, sterilized by filtering through 0.2 µm syringe filter, and stored at −20° C. in sealed vials. Appropriate amount of sterile water was added to controls in all assays to eliminate solvent effect.

Swarm agar plates were made using M8 medium supplemented with 0.2% glucose, 0.5% casamino acid, 1 mM MgSO4 and solidified with 0.5% Bacto agar. 24 Bacterial culture with $OD_{600}$ between 0.4 to 0.6 was inoculated as 3 µl aliquots. Swarm agar plates were incubated at 37° C. for 12 h and then incubated for additional 12 h at rt. For each set of experiment all the swarm plates were poured from same batch of agar and allowed to dry for 1 h before inoculation of bacteria.

Plasmids plasI-LVAgfp and prhlI-LVAgfp were transferred to wild type *P. aeruginosa* (PAO1) by electroporation method. Briefly, overnight culture of PAO1 was subcultured in 25 mL LB broth and was grown to reach the OD600 of 0.5 to 0.8 by shaking the culture at 37° C. Flask containing subculture was cooled on ice for 30 min. Cell pellet was obtained by centrifugation at 4500 rpm for 5 min. Supernatant was removed and cell pellet was resuspended in 20 mL ice-cold 300 mM sucrose solution. Cells were centrifuged at 4500 rpm for 5 min. Supernatant was discarded and cell pellet was resuspended in 1 mL ice-cold 300 mM sucrose solution. Cell suspension was transferred to a new 1.5 mL ice-cold microcentrifuge tube and spun down at 13,000 rpm for 30 sec. Supernatant was discarded and cell pellet was resuspended in 500 µL ice-cold 300 mM sucrose solution. For the last time cells were spun down at 13,000 rpm for 30 sec. After removal of the supernatant, cell pellet was resuspended in 100 ice-cold 300 mM sucrose solution. 50 µL of the competent cell suspension along with 5 µL of plasmid DNA in TE buffer was transferred to the cold 0.1 cm electroporation cuvette. Electroporator was set to Ec1 and pulse was passed through the cells. LB medium (1 mL) was immediately added to the electroporator cuvette and cell suspension was transferred to a sterile microcentrifuge tube and incubated for 1 h at 37° C. with shaking at 180 rpm. Cells were then spread on the LB agar (1.5%) plates supplemented with 300 µg/mL carbenicillin (antibiotic) and incubated over night at 37° C. to get the microcolonies of PAO1 (plasI-LVAgfp) or PAO1 (prhlI-LVAgfp).

Inhibitory effect of all the maltose hydrocarbons on *P. aeruginosa* biofilm formation was determined by crystal violet dye based biofilm inhibition assays. Overnight culture of wild type *P. aeruginosa* (PAO1) was sub cultured to an OD600 of 0.01 into the 95:5 M9+:Lb medium. 200 µL of the sub culture was aliquoted into the wells of 96 well polystyrene microtiter plate when it reached the $OD_{600}$ of 0.1. Predetermined concentrations of the test compounds were then added to the respective wells containing sub culture. Sample plates were wrapped in GLAD Press n' Seal® followed by incubation under stationary conditions for 24 h at 37° C. After incubation the media was discarded and the plates were washed with water and dried for 1 h at 37° C. The sample plates were stained with 200 µL of 0.1% aqueous solution of crystal violet (CV) and followed by incubation at ambient temperature for 20 min. The CV stain was then discarded and the plates were washed with water. The remaining biofilm adhered stain was re-solubilized with 200 µL of 30% acetic acid. After the stain was dissolved (15 minutes), 100 µL of the solubilized CV was transferred from each well into the corresponding wells of a new polystyrene microtiter dish. Biofilm inhibition was quantified by measuring the OD600 of each well in which a negative control lane wherein no biofilm was formed served as a background and was subtracted out. The percent inhibition was calculated by the comparison of the OD600 for biofilm grown in the absence of compound (control) versus biofilm grown in the presence of compound under identical conditions.

Overnight culture of PAO1-GFP was subcultured to an $OD_{600}$ of 0.01 into the 95:5 M9+:Lb medium. Subculture was allowed to reach the $OD_{600}$ of 0.1 in a rotary shaker at 250 rpm and 37° C. 200 µL of the subculture was then transferred to the wells of black microtiter plate with and without (control) maltose derivatives. This black 96 well plate was then incubated in a shaker at 37° C. for 2 h. After 2 h, bacterial culture from the plate was discarded and each well was washed once with saline water (0.85 w/v % aqueous NaCl solution). Fresh 95:5 M9+:Lb medium was added to the black 96 well plate and fluorescence of the surface adhered bacteria was measured by Synergy 2 multimode microplate reader with Gen5 data analysis software at an excitation wavelength of 500 nm and an emission wavelength of 540 nm. Background signal from 95:5 M9+:Lb medium was eliminated from all the samples.

Plate for biofilm dispersion assay was set up similar to crystal-violet based-biofilm inhibition assay but without adding any maltose derivative at the time of inoculation of bacteria in the 96 well plate. PAO1 was allowed to grow for 24 h at 37° C. After 24 h, bacterial culture was pipetted out and replaced with 200 µL of 110 µM maltose hydrocarbons and sterile water (control). After 1 h treatment with maltose hydrocarbons, biofilm was fixed and quantified using crystal violet dye as described above. The amount of dispersed biofilm was determined via comparison of the amount of biofilm at 24 h in the presence of maltose hydrocarbons versus the amount of biofilm in the "no compound" positive control at 24 h (wells with water treatment).

Five maltose derivatives with highest activity for biofilm inhibition and dispersion were selected for plotting dose response curve. Predetermined amounts maltose derivatives stock solution was added to the 200 µL bacterial culture in 96 well plate so that the final concentration of the agent reaches the desired values of 1, 5, 10, 20, 40, 85, 113, 140 µM. Biofilm inhibition and dispersion assay was carried as described previously.

Optical density was measured using Biotek ELx800 ™ absorbance microplate reader (BioTek Instruments, Inc., Winooski, Vt.) using Gen5™ data analysis software. The OD600 values were taken in sterile conditions at 0, 2, 4, 6, 8, 10, 12, and 24 h after bacterial culture inoculation in 96-well polystyrene plate with and without agents.

For an antagonist assay, overnight culture of *P. aeruginosa* PAO1/plasI-LVAgfp (las system) or PAO1/prhlI-LVAgfp (rhl system) in LB broth (supplemented with 300 μg/mL carbenicillin) was grown from a single colony on a LB agar plate supplemented with 300 μg/mL carbenicillin. The overnight culture was diluted and grown to OD600 of 0.1 in LB broth containing 300 μg/mL of carbenicillin. Bacterial culture (200 μL) was added to each well of a polystyrene 96-well microtiter plate containing an appropriate amount of maltose derivatives or sterile water as a control. The plate was incubated at 37° C. for 24 h in a rotary shaking incubator (250 rpm). The culture from each well was then transferred to a flat-bottom, 96-well plate with black wall (μClear, Greiner-One 655096). The fluorescence and OD absorbance in each well was measured by Synergy 2 multi-mode microplate reader with Gen5 data analysis software. Background signals from LB broth were eliminated from all samples. Fluorescence was measured at an excitation wavelength of 500 nm and an emission wavelength of 540 nm. Agonist assay was also done in a similar manner except PAO-JP2 (plasI-LVAgfp) and PAO-JP2 (prhlI-LVAgfP), double knockout strains were used instead of wt PAO1. Using the double knockout strains, agonist activities of the maltose derivatives were obtained (absence of natural autoinducers) and compared to the activities exhibited by adding natural autoinducers.

There is seen in FIGS. 36 and 37, the effect of compounds I-V on the swarming motility of rhlA mutants, where stock solution concentration was 11.7 mM, samples were prepared with 4 dilutions leading to 86 μM, 43 μM, 21.2 μM, 10.3 μM, and swarming was recorded at 14 h and 38 h after inoculation.

As seen in FIGS. 38 through 41, compounds IV and V were studied further with more concentrations. Compound IV was further studied as seen in FIGS. 42 and 43. As seen in FIGS. 44 and 45, certain compounds effectively inhibited and/or resulted in anti-adhesion of the biofilm of PAO1

Compounds according to the present invention may be used to treat infectious diseases in humans, such as bacterial infections common in cystic fibrosis. For example, the compounds may be administered via nebulizer. Nebulisation involves the conversion of a drug into a very fine aerosol or 'mist' so that it can be breathed straight into the lungs. Nebulizers are commonly used for the treatment of cystic fibrosis, asthma, COPD and other respiratory diseases. Nebulizers are particularly useful for those drugs which require high dose deposition to the lungs, or for distinct patient populations, such as those with severe disease, young children, the elderly, or mechanically-ventilated patients in a hospital intensive care unit. When treating various respiratory diseases, inhalation of aerosols to the lungs is the preferred route of administration of pharmaceutical compounds. Nebulizers are often preferred for this purpose to pressurized metered dose inhalers (pMDIs) and multidose dry powder inhalers (DPIs), and single-breath administration with pMDIs and DPIs. Nebulizers can be used across a wide dose range (g-up to gram-range) without loss of overall delivery performance, and patients can take treatment during multiple consecutive spontaneous breathing maneuvers. Some have higher delivery efficiency which allows for dramatically shorter inhalation times and a substantial reduction of drug volume and dose, as higher drug concentrations are feasible and less drug is wasted.

Any known nebulizers and nebulizer systems, and any nebulizer or nebulizer system developed in the future having the appropriate performance characteristics, can be used to deliver Dodecyl Maltoside, or the other compounds according to the present invention, to the lungs for the treatment of cystic fibrosis or any other disease in the lungs involving a bacterial biofilm. Nebulizer systems are used to deliver medications to control the symptoms and the progression of lung disease in people with cystic fibrosis. Nebulizers change a liquid medication into a mist so it can be breathed in. These systems decrease treatment time and deliver more medication into the lung than other conventional nebulizers which have slower air flows and larger medication droplets. Nebulizers using newer technologies, e.g. adaptive aerosol delivery or vibrating mesh technology, deliver the medication faster and may deliver more of the medication into the lung. These systems appear safe when used with the correct amount of medication, which may be different to that used in a conventional nebulizer system. Some studies suggest that people with cystic fibrosis may prefer these newer systems and may take more of their medication when using them.

There are several types of nebulizers currently in use for treating cystic fibrosis, although any new nebulizer developed will be of use in delivering the treatment of the present invention. These types of nebulizers are briefly summarized below, and then described individually in detail thereafter.

Conventional nebulizer systems—a machine sucks air in and pushes it out at high speed; a tube attaches the machine to a chamber holding the medication where the air breaks it up into a mist. The mist of medication is delivered constantly.

Adaptive aerosol delivery nebulizer systems—use conventional technology as described above, but also monitor breathing and deliver the mist of medication only while the person is breathing in.

Adaptive aerosol delivery nebulizer systems with vibrating mesh technology—monitor breathing and deliver the mist of medication only while the person is breathing in and use vibrating mesh technology, as described below, to change the liquid medication into a mist.

Vibrating mesh technology nebulizer systems—move the liquid medication through a metal mesh to break up the liquid into a mist where each drop is a similar size; they deliver the mist of medication constantly.

Ultrasonic nebulizer systems—use a crystal to vibrate the liquid medication at a high-frequency to break up the liquid medication into a mist; they deliver the mist of medication constantly.

Conventional nebulizer systems consist of a compressor coupled with a nebulizer chamber. The compressor entrains room air, compresses it to a higher pressure and emits the air at a given flow rate. The air enters the nebulizer chamber and passes through a small hole, a venturi, beyond which the air expands rapidly creating a negative pressure; this draws the medication up a feeding tube where it is atomised into particles. The particle sizes are variable, larger particles will impact on the baffle within the nebulizer chamber and onto the walls of the chamber and be returned back to the well of the chamber to be re-nebulized. The smaller particles will be continuously released from the nebulizer chamber during both inspiration and expiration of the person using the nebulizer system.

There are three main types of conventional nebulizer system: the jet nebulizer; the open-vent jet nebulizer; and the breath-assisted open-vent jet nebulizer. The jet nebulizer works continuously as described above. Open-vent jet nebulizers incorporate an open vent to allow extra air to be sucked into the chamber during inspiration. This results in greater air flow through the chamber and so greater densities of smaller respirable particles over a shorter period of time.

Breath-assisted open-vent jet systems use a valve system to allow air to be drawn in during inspiration as per the open-vent design. During expiration the valve closes and the flow of air through the chamber is decreased to that coming from the compressor only. This decreases the amount of particles released during expiration and therefore decreases medication wastage. One last adaptation of compressor and nebulizer systems is holding chambers. This is a chamber which is attached to the nebulizer and aerosol generated continuously by the nebulizer is held within the chamber. A negative pressure is created within the chamber during inspiration causing a valve to open and air to be entrained. This air picks up aerosol and delivers it to the person breathing in. An expiratory valve diverts expired air away from the chamber and the chamber continues to fill with aerosol. Holding chambers are designed to reduce medication wastage. A large number of conventional compressor and nebulizer combinations are available and these combinations have differing characteristics in terms of aerosol particle size, nebulization time and mass of medication delivered. Conventional nebulization systems tend to be cheaper than the alternatives and are less prone to reliability or delivery problems (or both) due to poor cleaning and maintenance. They are, however, noisy and bulky and therefore less portable; they also produce variable particle sizes and have a larger residual volume as compared to alternative systems, so leading to more wastage of medication.

Commonly used combinations of compressor and nebulizer are: a Porta-neb compressor with sidestream or ventstream nebuliser and a PARI TurboBOY with PARI LC SPRINT nebuliser.

Two nebulizer systems, the Halolite® and Prodose®, were the first and second generation of nebulizer systems to utilize AAD. These systems are no longer available as they have been superseded by an AAD nebulizer system incorporating vibrating mesh technology (VMT); the I-Neb AAD System®. With AAD, pressure changes relating to airflow are continuously analysed and timed pulses of aerosol (during the first 50% to 80% of inspiration only) are delivered based on the prior three breaths until the preset dose; an actuation, is delivered. This eliminates wastage of medication during exhalation which occurs with continuously delivering nebulizers and optimizes deposition. These systems were designed to give optimal efficiency and therefore require an alteration in the priming dose of medication used as compared to conventional nebulizer systems.

One nebulizer system, the I-Neb AADsystem®, utilizes VMT and AAD in combination in order to optimize deposition and treatment times. As detailed above, AAD occurs along with the use of VMT, as detailed below. Inhalation technique is assessed; the nebulizer system will not operate unless correctly set up and used at the appropriate angle. The system also stores adherence and delivery data such as treatment date, time, duration and completeness of dose which can be downloaded by the clinician or the person using the I-Neb using software supplied by Philips (Insight®). These nebulizer systems were designed to give optimal efficiency and therefore require an alteration in the priming dose of medication used as compared to conventional nebulizer systems. An example is the I-neb AAD System from Philips. Adaptive aerosol delivery (AAD) devices can also adapt to the patient's breathing pattern and stop drug delivery when a pre-set dose has been delivered.

VMT nebulizer systems aerosolize medication utilizing a vibrating, perforated mesh to generate particles. This is achieved by using a piezoelectric element which either vibrates a transducer horn or which is annular and encircles the mesh causing it to vibrate. Both methods result in medication being pumped through the perforated mesh creating homogenous particles. Some meshes are created with an electroplating technique which forms tapered holes and others by precision laser-drilling. Vibrating mesh systems are silent, portable (being small and battery powered), fast and produce more homogenously-sized particles as compared to conventional systems. There are a number of systems available. The Omron MicroAir®, the Aerogen Aeroneb Go®, and the Pan eFlow Rapid® were designed to be similar in efficiency to conventional breath-enhanced nebulizers by using larger particle sizes, a system housing which causes a high residual dose within the nebulizer system, or a medication reservoir with a larger residual volume. Other nebulizer systems were designed to give optimal efficiency and may therefore require an alteration in the priming dose of medication used. The AerogenOnQ®, Aerodose®, Aeroneb Pro® and Solo®, Pan eFlow® and Philips I-Neb® aim to deliver medication more efficiently and quicker. Some VMT systems are currently available for clinical use while others have only been utilized in research. A number of VMT systems use the piezoelectric crystal technology associated with ultrasonic nebulizers (see below) to create the vibration necessary to pump medication through a mesh. An example is a e-Flow® rapid nebulizer system from PARI GmbH.

Ultrasonic nebulizers utilize a piezoelectric crystal which vibrates creating standing waves within the surface of the medication, droplets move away from the crests of these waves becoming an aerosol. Large particles impact on a baffle to be re-nebulized in the same way as jet nebulizers. Ultrasonic nebulizers may be smaller and are quieter and quicker than conventional systems. There is controversy, however, as to whether they are suitable to nebulize certain medications.

Dodecyl Maltoside can be administered alone or in combination with other medications such as antibiotics. It is recommended that nebulized antibiotics be inhaled once or twice a day as prescribed by a doctor, and that they should be inhaled after chest physiotherapy. When nebulizing antibiotics, a filter should be used to prevent possible environmental contamination. The filters will have a disposable pad, which should be changed after every treatment. Antibiotics can take longer to nebulize (15-20 mins) but the new mesh nebulizers are much quicker. In one embodiment of the present invention, Dodecyl Maltoside is administered using a nebulizer system first and then an antibiotic is administered to the patient using a nebulizer system. In another embodiment, the order of administering Dodecyl Maltoside and the antibiotic are reversed. In one embodiment, the patient waits a specified period of time between the administration of the Dodecyl Maltoside, such as 1, 2, 3, 4, 5, 10, 15, 20, 30, 45, or 60 minutes, or any time period in between. In another embodiment, the Dodecyl Maltoside and an antibiotic are mixed prior to nebulizing and the nebulized mixture is administered to the patient using a nebulizing system.

In one embodiment of the present invention, other therapeutic substances are also administered to the patient, either before or after administration of the Dodecyl Maltoside dose. These other therapeutic substances can include hypertonic saline, bronchodilators, corticosteroids, antibiotics, mucolytics (e.g., DNase [Pulmozyme]), osmotics and antifungals, including specific substances such as tobramycin, colistin; dornase alfa, hypertonic sodium chloride, and other aerosolised medications. Mucolytics like Pulmozyme or hypertonic saline can make sputum thinner and therefore easier for the patient to clear, and administering a mucolytic before, with or after administering Dodecyl Maltoside may improve patient outcomes. In general, substances administered using nebulizing systems should be allowed to warm to room temperature before inhaling.

An inhaler or puffer can also be used for delivering medication into the body via the lungs. It is mainly used in the treatment of asthma and Chronic Obstructive Pulmonary Disease (COPD), although Zanamivir (Relenza), used to treat influenza, must be administered via inhaler. To reduce deposition in the mouth and throat, and to reduce the need for precise synchronization of the start of inhalation with actuation of the device, MDIs are sometimes used with a complementary spacer or holding chamber device. The most common type of inhaler is the pressurized metered-dose inhaler (MDI). In MDIs, medication is most commonly stored in solution in a pressurized canister that contains a propellant, although it may also be a suspension. The MDI canister is attached to a plastic, hand-operated actuator. On activation, the metered-dose inhaler releases a fixed dose of medication in aerosol form. The correct procedure for using an MDI is to first fully exhale, place the mouth-piece of the device into the mouth, and having just started to inhale at a moderate rate, depress the canister to release the medicine. The aerosolized medication is drawn into the lungs by continuing to inhale deeply before holding the breath for 10 seconds to allow the aerosol to settle onto the walls of the bronchial and other airways of the lung. Dodecyl Maltoside could be delivered, alone or with one or more of the therapeutic compounds discussed above or other appropriate substance, to a patient's lungs using an inhaler. A solution or suspension containing the Dodecyl Maltoside and any substance to be co-administered with it can be stored in a pressurized canister, which may contain a propellant as well. As with nebulizers, particles and droplets should be around less than 5 µm in diameter to deposit more frequently in the lower airways and greater than 0.5 µm in diameter to reduce the likelihood of their being exhaled.

Treatment dose administered using an inhaler or nebulizing system can be controlled using time, amount of medicine delivered (e.g., continue inhaling until the container holding the medicine is empty), or by the number of breaths. Depending upon the nebulizer or inhaler used and their settings, treatment times can vary from a minute or two up to an hour or two, with many treatment times having a duration of about 1, 2, 3, 4, 5, 10, 15, 20, 30, 45, 60, 75, 90 and 180 minutes. The appropriate number of breaths to complete a treatment will vary based upon the nebulizer or inhaler used and their settings, and the patient's condition, as well as the medication or medications being delivered. Appropriate breath counts can be 1, 3, 5, 10, 20, 30, 40, 50, 75, 100, 150, 200, 300, 400, 500, 600 or more, and any number in between. Some devices will precisely meter the amount of medication administered. When Dodecyl Maltoside is delivered in combination with another therapy, the dose of the other therapy can be a full dose or a partial dose, ranging from 0.1, 0.25, 0.5 to 0.75 dose. Appropriate doses of Dodecyl Maltoside for treating cystic fibrosis can be various ranges of doses, such as mg per kg, and should be apparent to those of skill in the art. These can be delivered as necessary once a month, once every two weeks, once a week, twice a week, three times a week, every other day, once a day, twice a day, three times a day, or more or less frequently.

The compounds of the present invention may also be used to treat any medical condition involving a bacterial pathogen that forms a biofilm. This includes chronic wounds, *C. difficile*, cholera, and Crohn's disease among others. The treatments may consist of applying the disaccharide hydrocarbons and other compounds of the present invention (e.g., dodecyl maltoside) either alone, to break up the biofilm and allow the immune system of a patient to act more effectively, or in combination with an appropriate anti-bacterial compound/treatment, either simultaneously administered as a mixture or in sequence (first the disaccharide hydrocarbons, then the anti-bacterial, or vice versa). Application could be in the form of a topical formulation (cream, solution, spray), a support matrix (hydrogel, collagen sponge, polymer or cotton gauze or bandage), or, for the treatment of intestinal biofilms, as an ingestible fluid or in a capsule or pill that releases the compounds in the gut. Alternatively, compounds of the present invention may be sprayed onto unwanted biofilms using an endoscope approach, such as when pathogenic biofilms in the intestines can be identified morphologically, visually, chemically, or fluorescently and directly targeted.

What is claimed is:

1. A method of treating an infection involving an amount of *Pseudomonas aeruginosa* bacteria forming a biofilm, comprising the step of administering an amount of dodecyl-β-maltoside (DβM) sufficient to disrupt any rhamnolipids produced by the amount of *Pseudomonas aeruginosa* bacteria and disburse the biofilm.

2. The method of claim 1, wherein the bacterial infection is a complication of cystic fibrosis.

3. The method of claim 2, wherein the step of administering an effective amount of dodecyl-β-maltoside (DβM) comprises the step of administering the effective amount of dodecyl-β-maltoside (DβM) via a nebulizer.

4. The method of claim 3, further comprising the step of administering an effective amount of an antibiotic.

5. The method of claim 3, wherein the step of administering an effective amount of an antibiotic comprises the step of administering the effective amount of an antibiotic via a nebulizer.

6. The method of claim 5, wherein the steps of administering an effective amount of dodecyl-β-maltoside (DβM) and administering an effective amount of an antibiotic are performed sequentially.

7. The method of claim 6, wherein the steps of administering an effective amount of dodecyl-β-maltoside (DβM) and administering an effective amount of an antibiotic are performed at the same time.

* * * * *